United States Patent
Qin et al.

(10) Patent No.: US 10,544,435 B2
(45) Date of Patent: Jan. 28, 2020

(54) L-ORNITHINE PRODUCTION IN EUKARYOTIC CELLS

(71) Applicant: BIOPETROLIA AB, Gothenburg (SE)

(72) Inventors: Jiufu Qin, Gothenburg (SE); Anastasia Krivoruchko, Gothenburg (SE); Florian David, Gothenburg (SE); Bo Jiang, Jiangsu (CN); Jens Nielsen, Gothenburg (SE)

(73) Assignee: CHRYSEA LIMITED, Dublin (IE)

( * ) Notice: Subject to any disclaimer, the term of this patent is extended or adjusted under 35 U.S.C. 154(b) by 0 days.

(21) Appl. No.: 15/556,737

(22) PCT Filed: Mar. 10, 2016

(86) PCT No.: PCT/SE2016/050193
§ 371 (c)(1),
(2) Date: Sep. 8, 2017

(87) PCT Pub. No.: WO2016/144247
PCT Pub. Date: Sep. 15, 2016

(65) Prior Publication Data
US 2018/0105850 A1     Apr. 19, 2018

Related U.S. Application Data

(60) Provisional application No. 62/166,050, filed on May 25, 2015, provisional application No. 62/132,349, filed on Mar. 12, 2015.

(51) Int. Cl.
| | |
|---|---|
| *C12P 13/10* | (2006.01) |
| *C12N 9/02* | (2006.01) |
| *C12N 9/10* | (2006.01) |
| *C12N 9/12* | (2006.01) |
| *C12N 9/78* | (2006.01) |
| *C12N 9/88* | (2006.01) |
| *C12N 13/00* | (2006.01) |
| *C12N 15/52* | (2006.01) |
| *C12P 13/00* | (2006.01) |

(52) U.S. Cl.
CPC ............ *C12P 13/10* (2013.01); *C12N 9/0008* (2013.01); *C12N 9/1018* (2013.01); *C12N 9/1096* (2013.01); *C12N 9/1217* (2013.01); *C12N 9/78* (2013.01); *C12N 9/88* (2013.01); *C12P 13/001* (2013.01); *C12Y 102/01038* (2013.01); *C12Y 201/03003* (2013.01); *C12Y 206/01011* (2013.01); *C12Y 207/02008* (2013.01); *C12Y 305/03001* (2013.01); *C12Y 401/01017* (2013.01); *C12Y 403/02001* (2013.01)

(58) Field of Classification Search
CPC .... C12Y 201/03003; C12Y 206/01011; C12Y 102/01038; C12Y 403/02001; C12Y 401/01017; C12Y 305/03001; C12Y 207/02008; C12N 9/1096; C12N 15/52; C12N 9/88; C12N 9/78; C12N 9/1217; C12N 9/0008; C12N 9/1018; C12P 13/001; C12P 13/10
See application file for complete search history.

(56) References Cited

U.S. PATENT DOCUMENTS

| | | | | |
|---|---|---|---|---|
| 7,629,142 | B2 * | 12/2009 | Ueda | C07K 14/245 435/106 |
| 7,751,981 | B2 * | 7/2010 | Famili | G06F 19/12 702/19 |
| 8,080,396 | B2 * | 12/2011 | Shiraga | C12N 9/0008 435/107 |
| 8,741,608 | B2 * | 6/2014 | Claes | C12N 15/77 435/114 |

FOREIGN PATENT DOCUMENTS

EP     2650358     10/2013

OTHER PUBLICATIONS

Hanfrey et al., Alternative spermidine biosynthetic route is critical for growth of Campylobacter jejuni and its dominant polyamine pathway in human gut microbiota. The J. Biol. Chem., 2011, vol. 286(50): 43301-43312. (Year: 2011).*

Kim et al., Enhanced tolerance of *Saccharomyces cerevisiae* to multiple lignocellulose-derived inhibitors through modulation of spermidine contents. Metabol. Eng., 2015, vol. 29: 46-55. (Year: 2015).*

(Continued)

*Primary Examiner* — Ganapathirama Raghu
(74) *Attorney, Agent, or Firm* — Myers Bigel, P.A.

(57) ABSTRACT

The present invention relates to the provision of genetically modified microbial cells, such as yeast cells with an improved ability for producing L-ornithine and its derivatives. Overproduction of L-ornithine is obtained in the first place by the down-regulation or attenuation of specially selected genes, wherein said genes encode enzymes involved in the L-ornithine consumption and/or degradation pathways. Further L-ornithine production ability is improved by down-regulation, attenuation, deletion or overexpression of specially selected genes, wherein said genes encode enzymes and/or proteins involved in the L-ornithine 'acetylated derivatives cycle', L-glutamate synthesis pathways, subcellular trafficking, TCA cycle, pyruvate carboxylation pathway, respiratory electron-transport chain, and the carbon substrates' assimilation machinery. The invention additionally provides a method to produce L-ornithine with said modified eukaryotic cells.

24 Claims, 26 Drawing Sheets
Specification includes a Sequence Listing.

(56) References Cited

OTHER PUBLICATIONS

Palani Murugan R., Rgulation of polyamine biosynthesis in *Saccharomyces cerevisiae*. 2005, Dissertation thesis, Univ. of Koln, pp. 1-126. (Year: 2005).*

Xu et al., Surprising arginine biosynthesis: a reappraisal of the enzymology and evolution of the pathway in microorganisms. Microbiol. Mol. Biol. Rev., 2007, vol. 71(1): 36-47. (Year: 2007).*

Davis R.H., Compartmental and regulatory mechanisms in the arginine pathways of Nerurospors crassa and *Saccharomyces cerevisiae*. Microbiol. Rev., 1986, vol. 50(3): 280-313. (Year: 1986).*

Jauniaux et al., Arginine metabolism in *Saccharomyces cerevisiae*: subcellular localization of the enzymes. J. Bacteriol., 1978, vol. 133(3): 1096-1107. (Year: 1978).*

Cooper, S.J. et al, "High-throughput profiling of amino acids in strains of the *Saccharomyces cerevisiae* deletion collection", Genome Research, vol. 20, No. 9, pp. 1288-1296 (Jul. 2010).

Jae Ho Shin et al, "Metabolic engineering of microorganisms for the production of L-arginine and its derivatives", *Microbial Cell Factories; Biomed Central*, vol. 13, p. 166. (Dec. 2014).

Qin J G et al., "Multiplex amino acid metabolism engineering for increased production of L-ornithine in yeast", Proceedings Metabolic Engineering X, (Jun. 15-19, 2014). Westin Bayshore, Vancouver, BC.

Qin, Jiufu et al, "Modular pathway rewiring of *Saccharomyces cerevisiae* enables high-level production of L-ornithine", *Nature Communications*, , vol. 6, p. 8224, (Sep. 2015)

Written Opinion and International Search Report corresponding to International Application No. PCT/SE2016/050193, dated Aug. 30, 2016, 15 pages.

* cited by examiner

SEQUENCE LISTING

```
<160> NUMBER OF SEQ ID NOS: 51

<210> SEQ ID NO 1
<211> LENGTH: 333
<212> TYPE: PRT
<213> ORGANISM: Saccharomyces cerevisiae

<400> SEQUENCE: 1

Met Glu Thr Gly Pro His Tyr Asn Tyr Lys Asn Arg Glu Leu Ser
1               5                   10                  15

Ile Val Leu Ala Pro Phe Ser Gly Gly Gln Gly Lys Leu Gly Val Glu
            20                  25                  30

Lys Gly Pro Lys Tyr Met Leu Lys His Gly Leu Gln Thr Ser Ile Glu
        35                  40                  45

Asp Leu Gly Trp Ser Thr Glu Leu Glu Pro Ser Met Asp Glu Ala Gln
    50                  55                  60
```

Phe Val Gly Lys Leu Lys Met Glu Lys Asp Ser Thr Thr Gly Gly Ser
65                  70                  75                  80

Ser Val Met Ile Asp Gly Val Lys Ala Lys Arg Ala Asp Leu Val Gly
                85                  90                  95

Glu Ala Thr Lys Leu Val Tyr Asn Ser Val Ser Lys Val Gln Ala
            100                 105                 110

Asn Arg Phe Pro Leu Thr Leu Gly Gly Asp His Ser Ile Ala Ile Gly
        115                 120                 125

Thr Val Ser Ala Val Leu Asp Lys Tyr Pro Asp Ala Gly Leu Leu Trp
    130                 135                 140

Ile Asp Ala His Ala Asp Ile Asn Thr Ile Glu Ser Thr Pro Ser Gly
145                 150                 155                 160

Asn Leu His Gly Cys Pro Val Ser Phe Leu Met Gly Leu Asn Lys Asp
                165                 170                 175

Val Pro His Cys Pro Glu Ser Leu Lys Trp Val Pro Gly Asn Leu Ser
            180                 185                 190

Pro Lys Lys Ile Ala Tyr Ile Gly Leu Arg Asp Val Asp Ala Gly Glu
        195                 200                 205

Lys Lys Ile Leu Lys Asp Leu Gly Ile Ala Ala Phe Ser Met Tyr His
    210                 215                 220

Val Asp Lys Tyr Gly Ile Asn Ala Val Ile Glu Met Ala Met Lys Ala
225                 230                 235                 240

Val His Pro Glu Thr Asn Gly Glu Gly Pro Ile Met Cys Ser Tyr Asp
                245                 250                 255

Val Asp Gly Val Asp Pro Leu Tyr Ile Pro Ala Thr Gly Thr Pro Val
            260                 265                 270

Arg Gly Gly Leu Thr Leu Arg Glu Gly Leu Phe Leu Val Glu Arg Leu
        275                 280                 285

Ala Glu Ser Gly Asn Leu Ile Ala Leu Asp Val Val Glu Cys Asn Pro
    290                 295                 300

Asp Leu Ala Ile His Asp Ile His Val Ser Asn Thr Ile Ser Ala Gly
305                 310                 315                 320

Cys Ala Ile Ala Arg Cys Ala Leu Gly Glu Thr Leu Leu
                325                 330

<210> SEQ ID NO 2
<211> LENGTH: 1725
<212> TYPE: DNA
<213> ORGANISM: Saccharomyces cerevisiae

<400> SEQUENCE: 2
atgtggagga gaatattcgc gcatgaactc aagtatgatc aacccaatgc atcttcaaaa      60
aacttgatcc tttcagttct gaatacaacc gctacaaaac gagaggctaa ggattatctc     120
tcaaaatata caaatgatag tgggcagcat aatcattgtt tgttttttat cagggacctg     180
cataaagtcg caccagcgat tttgtcccag ttttcaagtg tcataaagag actaggaatg     240
ctaggtttgc gacctatgtt tgtaattccg ccgtcgccaa ctcatgtaaa tatacaggca     300
gagttacttg acagtatcgt tacagaagca gatttaaagc cacttcacct taaggagggt     360
cttactaaat cccgcactgg gttatatcat tctgtttttt cgcaagagag tcgtttcttt     420
gatattggaa attccaattt tataccaatt gtgaaacctt atgtgtataa tgaagagact     480
gcttcagaat tcatgacaaa ggatgttgta aaatttatgg attgcctgtg ccaagggaat     540
attccacaca ttgacaaaatt cttcattcta ataatgccg gaggtatacc ttcgggagag     600

| | |
|---|---|
| agaaatgata acgctcatgt attcatcaat ctttctcagg aactcgagca tttgtcctcg | 660 |
| tcattatctc acaatataag cactctaacc aaacgagagc cacgctccca aaacctgtta | 720 |
| cacagaatgg aggtgtacgt taaaaaagat gagatatctt ccttagaatg tgaataccat | 780 |
| gatcatttag aaaacctgtt attgatggac aaagttttat caaatctagc ggctacagca | 840 |
| acgggactga ttacaactgt caaagctgcc gcactatcat cagataggaa aaatcctta | 900 |
| gtatataatt tattgacaga ccgatcgcta atttcttctt ctttaccaag gtttaaaaaa | 960 |
| aaggacggcg agatagactc accagccaac atgtttgatg atcacgcatg gtatgaattg | 1020 |
| ccttcccaac aggtaaatgc agctccttct aactcagatg cagttttagt gacaactgtt | 1080 |
| ctcaaaaagg gcgtccatat caaaacttat gactataaga cgctgactca attcaactca | 1140 |
| attgggcttc caagaagtt tcacgtacct gagaaaggag caaaccctc gagcaatagt | 1200 |
| ccaaaactag atatcaacaa atttaaatcc atcatcgatc agagctttaa aagatctttg | 1260 |
| gatttgcatg actacataaa aaggattaat ggaaaaatag ctacaattat tgtgataggt | 1320 |
| gattatgaag gcattgcaat tcttacctat gaaggctcgg aggaaaattc ctttgtttat | 1380 |
| ctcgataagt tcgccgttct accacacttg aaaggctcgc tgggtatatc tgatataatc | 1440 |
| ttcaatttga tgttcaaaaa atttcctaat gagatacttt ggagaagcag aaaagacaat | 1500 |
| gtggtgaaca gtggtatttt tcaacgtagc gttgctgtgc tagatttgtc gattgactta | 1560 |
| gaccccgaac actgtgatga aaagcaaagc caatttaaac tattttacta cggtaaccct | 1620 |
| caatacgcta agagggcact acgtgacaag aaacgtttaa gagaattcat gaggtctgtc | 1680 |
| agggacatca agccaagttg ggaaaatgaa aaaaatattt catga | 1725 |

<210> SEQ ID NO 3
<211> LENGTH: 2592
<212> TYPE: DNA
<213> ORGANISM: Saccharomyces cerevisiae

<400> SEQUENCE: 3

| | |
|---|---|
| atgccatctg ctagcttact cgtctcgaca aagagactta acgcttccaa attccaaaaa | 60 |
| tttgtgtctt cattaaacaa atccaccata gcaggatttg catctgtacc cttgagagct | 120 |
| ccaccatccg ttgcatttac gagaaagaaa gtcggatact caagaggta tgtttcatct | 180 |
| actaacggct tttcagctac tagatccact gtgatccaac tgttgaacaa tatcagcaca | 240 |
| aaaagagagg ttgaacaata tttgaaatat ttcacttccg tctcacaaca acaatttgct | 300 |
| gtgatcaagt gggtggtgc cattatcagc gacaatctac acgaactcgc ttcctgcttg | 360 |
| gcatttttgt atcatgttgg tctatatcca atagtttac atggtaccgg tcctcaggtt | 420 |
| aatgaaggc tagaagcgca gggaattgag ccagactata ttgatggtat tagaatcacg | 480 |
| gatgagcaca caatggccgt agttagaaaa tgttttttgg aacaaaatct taagctagtt | 540 |
| actgcattag aacagctagg ggtccgtgca agacccatta cttctggtgt ttttactgct | 600 |
| gactatttgg ataaggacaa atacaagcta gtgggcaata ttaaaagtgt cacaaaagag | 660 |
| ccaattgaag catctattaa ggcaggtgcc ctaccaatct tgacctcttt agccgaaact | 720 |
| gcttctggtc aaatgttgaa cgtcaacgcc gacgtagctg ctggtgaatt agcccgtgtt | 780 |
| tttgagcctt tgaagatcgt ttacctgaat gagaaagggg gtattatcaa tggctccacg | 840 |
| ggagaaaaaa tttcgatgat caatttggat gaagagtatg acgatttaat gaagcaaagt | 900 |
| tgggtgaagt atggtaccaa attaaaaatt agagaaatta aagagctttt ggactatctt | 960 |

-continued

```
cctcgttctt cttcagttgc aatcattaac gttcaagatc tacaaaaaga actgttcact    1020
gattctggtg cgggtactat gatcaggaga ggttacaaat tagtgaagag atcctccatt    1080
ggcgaatttc catccgctga tgctctaaga aaagctcttc aaagggacgc tggcattagt    1140
tccggtaaag aatctgttgc ttcttattta agatatttgg aaaactctga ttttgtctct    1200
tatgctgatg aacctcttga agcagtggcc attgtaaaga agatacgaa cgttcccaca    1260 ctagacaaat ttgtctgttc tgacgcagcc tggttgaata cgtcacaga taatgtattc    1320 aatgttttgc gccgtgattt tcctgcttta caatgggtag tcagtgaaaa tgatgctaac    1380
attgcatggc attttgataa gtctcaaggt tcatatctaa aaggcggaaa agttttgttc    1440
tggtatggta tcgatgatat aaatacaata tccgagctcg ttgaaaattt tgtgaagtcg    1500
tgtgacactg cttctaccct caactcatca gcaagtagtg gagtatttgc taacaaaaaa    1560
tcagctaggt cgtactcaac tagatccact cctcgtcccg agggagttaa caccaacccct   1620 ggtcgtgtcg cgcttattgg tgctagaggt tacacaggta aaaatttggt atctttgatc    1680
aacggccacc catatttaga agtggcccat gtttcttctc gtgaattgaa aggtcaaaag    1740
ttgcaagatt atacaaaatc cgaaattata tatgaaagtt tgcaaataca ggatattagg    1800
aaactggaag aacaaaatgc tgtggacttt tgggttatgg cattacccaa caaagtctgt    1860 gaaccttcg ttgagacaat ccaaagtgtt catggtaagt ctaaaattat tgatctgtcc    1920
gctgatcaca ggtttgtatc agaatcagac tgggcttacg gttgccaga attgaatgat    1980 agagcaaaaa ttgcaaacgc tgccaaaatt gctaatcccg ttgttatgc tactggttcg    2040 caattaacta tttctccgtt aacaaagtat atcaatggtc ttccaactgt gtttggtgtt    2100
tcagggtatt caggcgcggg gacgaagcct ctccaaaaa acgatcccaa attcttgaac    2160
aataacttaa ttccttacgc tttaagtgat catatacacg aacgcgaaat ctcagctcgc    2220
attgggcaca atgttgcatt catgccccat gttgggcagt ggtttcaagg tatctctttg    2280
accgtctcta ttccaataaa aaaaggttcc ttgtctattg atgagatcag gaaattatac    2340
agaaattttt acgaagacga aaagctagta catgtcatcg atgatatccc actggttaaa    2400
gatattgagg gcacccatgg tgtagttatt ggtggtttca agctgaatga tgctgaagat    2460
cgtgtagttg tttgcgcaac catcgataac ttacttaaag gcgccgctac tcaatgtctg    2520
caaaatatta atcttgctat gggttatgga gagtatgctg gtatccctga aaataaaatt    2580
attggtgtct ga                                                        2592
```

<210> SEQ ID NO 4
<211> LENGTH: 1272
<212> TYPE: DNA
<213> ORGANISM: Saccharomyces cerevisiae

<400> SEQUENCE: 4

```
atgtttaaaa gatatttatc cagtacgtca tcaagaagat ttacaagcat tttagaggaa      60
aaggcctttc aagtgaccac ttactctaga cctgaagatc tatgtataac tagaggtaaa    120
aatgcaaagc tgtatgatga cgtgaatggt aaagaatata tcgatttcac cgcaggtatt    180
gcggtgaccg cattaggcca tgcaaatcct aaagtggcag aaattctgca ccatcaggct    240
aacaaactgg ttcattcctc caacctttac ttcactaagg aatgtttgga tttaagtgaa    300
aagattgttg aaaagaccaa gcaattcggt ggtcaacacg acgcctcaag agtattttta    360
tgtaattctg gtacggaagc aaatgaagct gctttgaagt ttgcaaagaa acatggtata    420
atgaaaaatc ctagcaagca aggcattgtt gcatttgaga actctttca tggccgtact    480
```

```
atgggcgctt tatctgtcac ttggaatagt aaatatagaa ctccttttgg ggatttggtt      540
ccccatgtct cattcttaaa tttgaatgac gaaatgacca aactacaaag ttatatcgag      600
accaaaaagg acgagattgc tggtttaatt gtcgagccca tacaaggtga aggtggggtt      660
tttcccgtag aagttgaaaa gctaaccgga ttgaagaaaa tatgtcaaga taatgatgtg      720
attgtcattc atgatgaaat tcaatgcggt ttgggccgtt caggtaaact atgggctcat      780
gcttatttac caagtgaggc tcatccggat attttacat ctgccaaagc attgggaaat      840
ggcttcccca tcgctgccac catcgtcaat gaaaagtta ataatgcttt gagagttggt      900
gaccacggca ccacgtatgg tggtaatccg ctggcctgtt ctgtaagcaa ctatgttttg      960
gataccatag cagacgaagc ttttttgaaa caagtctcta agaagagtga tatcttacaa     1020
aagcgcttgc gcgaaattca agccaaatat ccaaatcaaa taaagactat cagaggaaaa     1080
ggtttgatgc ttggtgctga gttcgtcgaa ccacccaccg aggtcatcaa aaaggccaga     1140
gaattgggac ttttgatcat taccgctggt aagagtaccg ttagatttgt tcccgcatta     1200
acgattgaag acgaactaat cgaagaaggg atggatgctt tgaaaaggc tattgaagcg     1260 gtttacgctt aa                                                        1272

<210> SEQ ID NO 5
<211> LENGTH: 1326
<212> TYPE: DNA
<213> ORGANISM: Saccharomyces cerevisiae

<400> SEQUENCE: 5
atgagaatat catcaacatt gcttcaacgc tcgaagcagc ttatagataa gtatgcatta       60
tacgtgccca agacgggctc ttttcctaaa ggatttgaag taggctacac tgcatctgga      120
gtcaaaaaaa acgggagcct ggacctgggt gtaatcttga ataccaataa atctcgtcct      180
tcaaccgcag cagctgtttt cacgaccaat aaattcaaag ctgcgccagt tttgacatcg      240
aaaaaagtcc ttgaaactgc tcgtggtaaa aacatcaacg ctattgtagt caattccggt      300
tgtgctaact cggtcacagg tgatcttggt atgaaagatg cccaagtaat gattgatttg      360
gttaacgata aaattggtca aaaaaattct accctagtca tgtctacagg cgttattgga      420
caacgactac agatggacaa gatcagcact ggtatcaata aaattttttgg agaagaaaag      480 ttcggcagtg attttaactc ttggttgaac gtagccaaat caatctgtac tactgatact      540
ttcccaaaat tagttacatc tagattcaaa ttacctagtg gtactgagta ctctttgaca      600
ggtatggcaa agggcgcggg tatgatttgt ccgaatatgg ctaccttatt aggtttcata      660
gttacagatc ttcctattga aagcaaggcg ttgcagaaga tgctgacttt cgctactacc      720
cgttcattta ttgtatatc ggtggacggt gatatgagca ccaatgacac aatttgcatg      780
ttggccaacg gtgctattga caccaaagaa attaacgaag actctaaaga ttttgaacaa      840
gtaaaattgc aggtcacaga atttgctcag cgcttggccc agttagtcgt tcgcgatggt      900
gaaggttcga caagtttgt tactgttaac gttaaaaatg cttctgcattt tgaagacgcc      960 aaaataattg ctgaatcaat ctcaaactct atgttggtca aaaccgcact atatgggcaa     1020
gatgccaatt ggggaagaat attgtgcgcg atcgggtatg caaagctgaa tgacttaaaa     1080
tctctagatg tcaacaaaat taatgttagc tttattgcta ccgacaattc agaacctcgt     1140
gagctgaagc ttgtcgctaa tggtgtgcca caattggaga tcgatgaaac aagggcttct     1200
gaaatattgg ctttgaatga tttggaagtg tctgtcgact tgggaaccgg tgatcaggca     1260
```

```
gcacaatttt ggacttgtga tttatcacat gaatatgtaa caattaacgg tgattaccgt    1320
tcataa                                                              1326

<210> SEQ ID NO 6
<211> LENGTH: 1365
<212> TYPE: DNA
<213> ORGANISM: Saccharomyces cerevisiae

<400> SEQUENCE: 6
atgtcagagc cagaatttca acaagcttac gaagaagttg tctcctcttt ggaagactct     60
actcttttcg aacaacaccc agaatacaga aaggttttgc caattgtttc tgttccagaa    120
agaatcatac aattcagagt cacctgggaa aatgacaagg gtgaacaaga agttgctcaa    180
ggttacagag tgcaatataa ctccgccaag ggtccataca agggtggtct acgtttccat    240
ccttccgtga acttgtctat cttgaaattc ttgggtttcg aacaaatctt caagaactcc    300
ttgaccggcc tagacatggg tggtggtaaa ggtggtctat gtgtggactt gaagggaaga    360
tctaataacg aaatcagaag aatctgttat gctttcatga gagaattgag cagacacatt    420
ggtcaagaca ctgacgtgcc agctggtgat atcggtgttg gtggtcgtga aattggttac    480
ctgttcggtg cttacagatc atacaagaac tcctgggaag gtgtcttaac cggtaagggt    540
ttgaactggg gtggttcttt gatcagacca gaagccactg gttacggttt agtttactat    600
actcaagcta tgatcgacta tgccacaaac ggtaaggaat ctttcgaagg taagcgcgtc    660
accatctctg gtagtggtaa cgttgctcaa tacgctgcct tgaaggttat tgagctaggt    720
ggtactgtcg tttccctatc tgactccaag ggttgtatca tctctgaaac tggtatcacc    780
tccgaacaag tcgctgatat ttccagtgct aaggtcaact tcaagtcctt ggaacaaatc    840
gtcaacgaat actctacttt ctccgaaaac aaagtgcaat acattgctgg tgctcgtcca    900
tggacccacg tccaaaaggt cgacattgct tgccatgtgc cacccaaaa tgaagtcagc    960 ggtgaagaag ccaaggcctt ggttgctcaa gtgtcaagt ttattgccga aggttccaac   1020
atgggttcca ctccagaagc tattgccgtc tttgaaactg ctcgttccac cgccactgga   1080
ccaagcgaag ctgtttggta cggtccacca aaggctgcta acttgggtgg tgttgctgtt   1140
tctggtttag aaatggcaca aaactctcaa gaatcacat ggactagcga aagagttgac   1200
caagagttga gagaattat gatcaactgt tcaatgaat gtatcgacta tgccaagaag   1260
tacactaagg acggtaaggt cttgccatct ttggtcaaag gtgctaatat cgcaagtttc   1320
atcaaggtct ctgatgctat gtttgaccaa ggtgatgtat tttaa                 1365

<210> SEQ ID NO 7
<211> LENGTH: 1374
<212> TYPE: DNA
<213> ORGANISM: Saccharomyces cerevisiae

<400> SEQUENCE: 7
atgacaagcg aaccagagtt tcagcaggct tacgatgaga tcgtttcttc tgtggaggat     60
tccaaaattt ttgaaaaatt cccacagtat aaaaaagtgt tacctattgt ttctgtcccg    120
gagaggatca ttcaattcag ggtcacgtgg gaaaatgata tggcgagcag agaagtggct    180
caaggataca gggtgcagtt caattcagcc aagggcccct acaagggtgg cctacgcttc    240
cacccatcag tgaacctgtc tatcctaaaa ttttgggtt ttgaacagat cttcaagaat    300
gcgctcactg ggctagatat gggcggtggt aagggtggcc tgtgtgtgga cttgaaaggc    360
aagtctgaca acgagatcag aaggatttgt tatgcgttca tgagagaact gagcaggcat    420
```

```
attggtaagg acacagacgt gcccgcagga gatattggtg tcggtggccg tgaaattggc      480
tacctattcg gcgcttacag atcatacaag aactcctggg aaggtgtgtt gactggtaag      540
ggtttaaact ggggtggctc acttatcagg ccggaggcca ccgggttcgg cttagtttac      600
tatacgcaag caatgatcga ttatgcaaca aacggcaagg agtcgtttga gggcaaacgt      660
gtgacaatct ccggaagtgg caatgttgcg caatatgcag ctttgaaagt gatcgagctg      720
ggtggtattg tggtgtcttt atccgattcg aaggggtgca tcatctctga cgggcatt       780 acttctgagc aaattcacga tatcgcttcc gccaagatcc gtttcaagtc gttagaggaa      840
atcgttgatg aatactctac tttcagcgaa agtaagatga gtacgttgc aggagcacgc      900 ccatggacgc atgtgagcaa cgtcgacatt gccttgccct gtgccaccca aaacgaggtc      960 agtggtgacaa agccaaggc cctagtggca tctggcgtta agttcgttgc cgaaggtgct      1020
aacatgggtt ctacacccga ggctatttct gttttcgaaa cagcgcgtag cactgcaacc      1080
aatgcaaagg atgcagtttg gtttgggcca ccaaaggcag ctaacctggg cggcgtggca      1140
gtatccggtc tggaaatggc tcagaattct caaaaagtaa cttggactgc cgagcgggtc      1200
gatcaagaac taagaagat aatgatcaac tgcttcaacg actgcataca ggccgcacaa      1260
gagtactcta cggaaaaaaa tacaaacacc ttgccatcat tggtcaaggg ggccaacatt      1320
gccagcttcg tcatggtggc tgacgcaatg cttgaccagg gagacgtttt ttag           1374
```

<210> SEQ ID NO 8
<211> LENGTH: 1113
<212> TYPE: DNA
<213> ORGANISM: Saccharomyces cerevisiae
<400> SEQUENCE: 8

```
atggctgaag caagcatcga aaagactcaa attttacaaa aatatctaga actggaccaa       60
agaggtagaa taattgccga atacgtttgg atcgatggta ctggtaactt acgttccaaa      120
ggtagaactt tgaagaagag aatcacatcc attgaccaat gccagaatg gaacttcgac      180 ggttcttcta ccaaccaagc gccaggccac gactctgaca tctatttgaa acccgttgct      240
tactacccag atcccttcag gagaggtgac aacattgttg tcttggccgc atgttacaac      300
aatgacggta ctccaaacaa gttcaaccac agacgaag ctgccaagct atttgctgct      360
cataaggatg aagaaatctg gtttggtcta gaacaagaat acactctatt tgacatgtat      420
gacgatgttt acggatggcc aaagggtggg tacccagctc acaaggtcc ttactactgt      480 ggtgttggtc ccgtaaggt ttatgccaga gacatgatcg aagctcacta cagagcttgt      540
ttgtatgccg gattagaaat ttctggtatt aacgctgaag tcatgccatc tcaatgggaa      600
ttccaagtcg gtccatgtac cggtattgac atgggtgacc aattatggat ggccagatac      660
tttttgcaca gagtggcaga agagtttggt atcaagatct cattccatcc aaagccattg      720
aagggtgact ggaacggtgc cggttgtcac actaacgttt ccaccaagga atgagacaa      780 ccaggtggta tgaaatacat cgaacaagcc atcgagaagt tatccaagag acacgctgaa      840
cacattaagt tgtacggtag cgataacgac atgagattaa ctggtagaca tgaaaccgct      900
tccatgactg ccttttcttc tggtgtcgcc aacagaggta gctcaattag aatccccaaga      960 tccgtcgcca aggaaggtta cggttacttt gaagaccgta gaccagcttc caacatcgac      1020
ccatacttgg ttcaggtat catgtgtgaa actgtttgcg gtgctattga caatgctgac      1080
atgacgaagg aatttgaaag agaatcttca taa                                   1113
```

<210> SEQ ID NO 9
<211> LENGTH: 6438
<212> TYPE: DNA
<213> ORGANISM: Saccharomyces cerevisiae

<400> SEQUENCE: 9

| | | | | | | |
|---|---|---|---|---|---|---|
| atgccagtgt | tgaaatcaga | caatttcgat | ccattggaag | aagcttacga | aggtgggaca | 60 |
| attcaaaact | ataacgatga | acaccatctt | cataaatctt | gggcaaatgt | gattccggac | 120 |
| aaacgaggac | tttacgaccc | tgattatgaa | catgacgctt | gtggtgtcgg | tttcgtagca | 180 |
| aataagcatg | gtgaacagtc | tcacaagatt | gttactgacg | ctagatatct | tttagtgaat | 240 |
| atgacacatc | gtggtgccgt | ctcatctgat | gggaacggtg | acggtgccgg | tattctgcta | 300 |
| ggtattcctc | acgaatttat | gaaaagagaa | ttcaagttag | atcttgatct | agacatacct | 360 |
| gagatgggca | aatacgccgt | aggtaacgtc | ttcttcaaga | agaacgaaaa | aaataacaag | 420 |
| aaaaatttaa | ttaagtgtca | gaagattttc | gaggatttag | ctgcatcctt | caacttatcc | 480 |
| gtattaggtt | ggagaaacgt | ccccgtagat | tctactattt | taggagacgt | tgcattatct | 540 |
| cgtgaaccta | ctattctaca | gccattattg | gttccattgt | atgatgaaaa | acaaccggag | 600 |
| tttaatgaaa | ctaaatttag | aactcaattg | tatcttttaa | ggaaggaggc | ctctcttcaa | 660 |
| ataggactgg | aaaactggtt | ctatgtttgt | tccctaaaca | ataccaccat | tgtttacaag | 720 |
| ggtcaattga | cgccagctca | agtgtataac | tactatcccg | acttgactaa | tgcgcatttc | 780 |
| aaatcccaca | tggcgttggt | ccattcaaga | ttttccacta | atactttccc | ctcttgggat | 840 |
| agagctcaac | tttacgttg | gctagctcat | aatggtgaaa | ttaacacctt | aagaggtaac | 900 |
| aagaattgga | tgcgctccag | agaaggtgtg | atgaattcag | caactttcaa | agatgagtta | 960 |
| gacaaactat | acccaattat | cgaagaaggt | ggttctgatt | cagctgcatt | ggataacgtt | 1020 |
| ttagaactat | tgactattaa | tggcacatta | tctctacctg | aagctgttat | gatgatggtt | 1080 |
| cctgaagcgt | atcataagga | tatggattct | gacctaaaag | catggtacga | ctgggctgca | 1140 |
| tgtctgatgg | aaccttggga | tggtccagct | tgttaactt | tcactgatgg | acgttactgt | 1200 |
| ggtgctatat | tggatagaaa | tggtttaaga | ccttgtcgtt | attacatcac | tagtgatgac | 1260 |
| agagttatct | gtgcttcaga | ggtaggtgtc | attcctatcg | aaaattcatt | ggttgttcaa | 1320 |
| aaaggtaaac | tgaagccagg | tgatttattc | ctagtggata | tcaattggg | tgaaatggtc | 1380 |
| gatactaaaa | agttaaaatc | tcaaatctca | aaaagacaag | attttaagtc | ttggttatcc | 1440 |
| aaagtcatca | gttagacga | cttgttatca | aaaccgcta | atttggttcc | taaagaattt | 1500 |
| atatcacagg | attcattgtc | tttgaaagtt | caaagtgacc | cacgtctatt | ggccaatggt | 1560 |
| tataccttcg | aacaagtcac | atttctgtta | actccaatgg | ctttaacagg | taaagaagct | 1620 |
| ttaggttcga | tgggtaacga | tgcgccactg | gcttgtttaa | atgaaaatcc | tgtcttactt | 1680 |
| tatgattatt | tcagacaatt | gtttgctcaa | gtgaccaatc | ctccaattga | cccaattcgt | 1740 |
| gaagcaaatg | ttatgtcgtt | agaatgttat | gtcggacctc | aaggcaacct | tttggaaatg | 1800 |
| cattcatctc | aatgtgatcg | tttattattg | aaatctccta | ttttgcattg | gaatgagttc | 1860 |
| caagctttga | aaacattga | agctgcttac | ccatcatggt | ctgtagcaga | aattgatatc | 1920 |
| acattcgaca | gagtgaggg | tctattgggc | tataccgaca | caattgataa | aatcactaag | 1980 |
| ttagcgagcg | aagcaattga | tgatggtaaa | aagatcttaa | taattactga | caggaaaatg | 2040 |
| ggtgccaacc | gtgtttccat | ctcctctttg | attgcaattt | catgtattca | tcatcaccta | 2100 |
| atcagaaaca | agcagcgttc | ccaagttgct | ttgattttgg | aaacaggtga | agccagagaa | 2160 |

```
attcaccatt tctgtgtcct actaggttat ggttgtgatg gtgtttatcc atacttagcc   2220
atggaaactt tggtcagaat gaatagagaa ggtctacttc gtaatgtcaa caatgacaat   2280
gatacacttg aggaagggca aatactagaa aattacaagc acgctattga tgcaggtatc   2340
ttgaaggtta tgtctaaaat gggtatctcc actctagcat cctacaaagg tgctcaaatt   2400
tttgaagccc taggtttaga taactctatt gttgatttgt gtttcacagg tacttcttcc   2460
agaattagag gtgtaacttt cgagtatttg gctcaagatg ccttttcttt acatgagcgt   2520
ggttatccat ccagacaaac cattagtaaa tctgttaact taccagaaag tggtgaatac   2580
cactttaggg atggtggtta caaacacgtc aacgaaccaa ccgcaattgc ttcgttacaa   2640
gatactgtca gaaacaaaaa tgatgtctct tggcaattat atgtaaagaa ggaaatggaa   2700
gcaattagag actgtacact aagaggactg ttagaattag attttgaaaa ttctgtcagt   2760
atccctctag aacaagttga accatggact gaaattgcca gaagatttgc gtcaggtgca   2820
atgtcttatg gttctatttc tatggaagct cactctacat ggctattgc catgaatcgt   2880 ttaggggcca aatccaattg tggtgaaggt ggtgaagacg cagaacgttc tgctgttcaa   2940
gaaaacggtg atactatgag atctgctatc aaacaagttg cttccgctag attcggtgta   3000
acttcatact acttgtcaga tgctgatgaa atccaaatta agattgctca gggtgctaag   3060
ccgggtgaag tggtgaact accagcccac aaagtgtcta aggatatcgc aaaaaccagg   3120
cactccaccc ctaatgttgg gttaatctct cctcctcctc atcacgatat ttattccatt   3180
gaagatttga acaactgat ttatgatttg aaatgtgcta atccaagagc gggaatttct   3240
gtaaagttgg tttccgaagt tggtgttggt attgttgcct ctggtgtagc taaggctaaa   3300
gccgatcata tcttagtttc tggtcatgat ggtggtacag gtgctgcaag atggacgagt   3360
gtcaaatatg cgggtttgcc atgggaatta ggtctagctg aaactcacca gactttagtc   3420
ttgaatgatt taagacgtaa tgttgttgtc caaaccgatg gtcaattgag aactgggttt   3480
gatattgctg ttgcagtttt attaggggca gaatctttta ccttggcaac agttccatta   3540
attgctatgg gttgtgttat gttaagaaga tgtcacttga actcttgtgc tgttggtatt   3600
gccacacaag atccatattt gagaagtaag tttaagggtc agcccgaaca tgttatcaac   3660
ttcttctatt acttgatcca agatttaaga caaatcatgg ccaagttagg attccgtacc   3720
attgacgaaa tggtgggtca ttctgaaaaa ttaaagaaaa gggacgacgt aaatgccaaa   3780 gccataaaata tcgatttatc tcctattttg accccagcac atgttattcg tccaggtgtt   3840
ccaaccaagt tcactaagaa acaagaccac aaactccaca cccgtctaga taataagtta   3900
atcgatgagg ctgaagttac tttggatcgt ggcttaccag tgaatattga cgcctctata   3960
atcaatactg atcgtgcact cggttctact ttatcttaca gagtctcgaa gaaatttggt   4020
gaagatggtt tgccaaagga caccgttgtc gttaacatag aaggttcagc gggtcaatct   4080 tttgtgctt tcctagcttc tggtatcact tttatcttga tggtgatgc taatgattat   4140 gttggtaaag gtttatccgg tggtattatt gtcattaaac caccaaagga ttctaaattc   4200
aagagtgatg aaaatgtaat tgttggtaac acttgtttct atggtgctac ttctggtact   4260
gcattcattt caggtagtgc cggtgagcgt ttcggtgtca gaaactctgg tgccaccatc   4320
gttgttgaga gaattaaggg taacaatgcc tttgagtata tgactggtgg tcgtgccatt   4380
gtcttatcac aaatgaatc cctaaacgcc ttctctggtg ctactggtgg tattgcatac   4440
tgtttaactt ccgattacga cgattttgtt ggaaagatta caaagatac tgttgagtta   4500
```

```
gaatcattat gtgacccggt cgagattgcg tttgttaaga atttgatcca ggagcattgg      4560
aactacacac aatctgatct agcagccagg attctcggta atttcaacca ttatttgaaa      4620
gatttcgtta aagtcattcc aactgattat aagaaagttt tgttgaagga gaaagcagaa      4680
gctgccaagg caaaggctaa ggcaacttca gaatacttaa agaagtttag atcgaaccaa      4740
gaagttgatg acgaagtcaa tactctattg attgctaatc aaaaagctaa agagcaagaa      4800
aaaaagaaga gtattactat ttcaaataag gccactttga aggagcctaa ggttgttgat      4860
ttagaagatg cagttccaga ttccaaacag ctagagaaga atagcgaaag gattgaaaaa      4920
acacgtggtt ttatgatcca caaacgtcgt catgagacac acagagatcc aagaaccaga      4980
gttaatgact ggaaagaatt tactaaccct attaccaaga aggatgccaa atatcaaact      5040
gcgagatgta tggattgtgg tacaccattc tgtttatctg ataccggttg tcccctatct      5100
aacattatcc ccaagtttaa tgaattgtta ttcaagaacc aatggaagtt ggcactggac      5160
aaattgctag agacaaacaa tttcccagaa ttcactggaa gagtatgtcc agcaccctgt      5220
gagggagctt gtacactagg tattattgaa gacccagtcg gcataaaatc ggttgaaaga      5280
attatcattg acaatgcttt caaggaagga tggattaagc cttgtccacc aagtacacgc      5340
actggcttta cagtgggtgt cattggttct ggtccagcag gtttagcgtg tgctgatatg      5400
ttgaaccgtg ccggacatac ggtcactgtt tatgaaagat ccgaccgttg tggtgggtta      5460
ttgatgtatg gtattccaaa catgaagttg ataaggcta tagtgcaacg tcgtattgat      5520
ctattgagtg ccgaaggtat tgactttgtt accaacaccg aaattggtaa aaccataagc      5580
atggatgagc taaagaacaa gcacaatgca gtagtgtatg ctatcggttc taccattcca      5640
cgtgacttac ctattaaggg tcgtgaattg aagaatattg atttgccat gcagttgttg      5700 gaatctaaca caaaagcttt attgaacaaa gatctggaaa tcattcgtga aaagatccaa      5760
ggtaagaaag taattgttgt cggtggtggt gacacaggta acgattgttt aggtacatct      5820 gtaagcacg tgtcagcatc agttttgaat ttcgaattgt tgcctgagcc accagtggaa      5880
cgtgccaaag acaatccatg gcctcaatgg ccgcgtgtca tgagagtgga ctacggtcat      5940
gctgaagtga aagagcatta tggtagagac cctcgtgaat actgcatctt gtccaaggaa      6000
tttatcggta acgatgaggg tgaagtcact gccatcagaa ctgtgcgcgt agaatggaag      6060
aagtcacaaa gtggcgtatg gcaaatggta gaaattccca acagtgaaga gatctttgaa      6120
gccgatatca ttttgttgtc tatgggtttc gtgggtcctg aattgatcaa tggcaacgat      6180
aacgaagtta agaagacaag acgtggtacg attgccacac tcgacgactc ctcatactct      6240
attgatggag gaaagacttt tgcatgtggt gactgtagaa gagggcaatc tttgattgtc      6300
tgggccatcc aagaaggtag aaaatgtgct gcctctgtcg ataagttcct aatggacggc      6360
actacgtatc taccaagtaa tggtggtatc gttcaacgtg attacaaact attgaaagaa      6420
ttagctagtc aagtctaa                                                   6438
```

<210> SEQ ID NO 10
<211> LENGTH: 879
<212> TYPE: DNA
<213> ORGANISM: Saccharomyces cerevisiae

<400> SEQUENCE: 10

```
atggaggaca gtaaaaagaa aggattaata gaaggcgcta tactcgatat aataaacggt        60
tccattgcag gcgcctgtgg taaggtgatc gagtttcctt tcgatactgt gaaagtcagg       120
ttgcaaacac aagcatccaa cgtgttccca acaacatggt cttgtataaa atttacttac       180
```

| | |
|---|---:|
| caaaatgaag gaatagcacg agggttttt caaggcattg cttcacctt agttggagca | 240 |
| tgtctggaga acgcgacatt atttgtgtct tataaccaat gttctaaatt tttagaaaaa | 300 |
| catacaaacg tttccccgtt ggggcaaatc ctgatctctg gtggagtagc gggttcatgt | 360 |
| gctagtttag ttttgacacc cgtggagctg gtgaagtgta agttgcaggt tgcgaactta | 420 |
| caagttgcat cagctaaaac gaaacataca aaggtgttgc ctacaataaa agcaattata | 480 |
| actgagagag gattggcagg attgtggcaa gggcaatcgg gcacttttat tcgagaaagc | 540 |
| ttcggtggtg ttgcctggtt tgcaacctac gaaatagtta agaagtcgtt gaaagatagg | 600 |
| cactcccttg atgacccaaa aagagatgaa agtaagatat gggaactact tattagtgga | 660 |
| gggagcgctg gattggcatt caacgccagt attttttcctg cggatactgt gaaatcagta | 720 |
| atgcaaactg aacatataag cctcaccaat gcgtgaaga agatatttgg caaatttgga | 780 |
| ctaaagggtt tttatcgagg actgggtata acccttttta gggcagtacc agcaaacgct | 840 |
| gcagttttt acatctttga gactctttct gcactttaa | 879 |

<210> SEQ ID NO 11
<211> LENGTH: 2709
<212> TYPE: DNA
<213> ORGANISM: Saccharomyces cerevisiae

<400> SEQUENCE: 11

| | |
|---|---:|
| atggagcaaa tcaattcgaa cagtagaaaa aagaagcaac aattggaagt attcaaatat | 60 |
| tttgcaagtg tccttacaaa agaggacaag cctattagta tcagtaatgg tatgttagat | 120 |
| atgccgacag tgaactccag taaactcaca gcaggaaatg ggaaacctga cacggagaag | 180 |
| cttacaggag aactaatttt aacatacgac gatttcattg aactgatatc tagctcaaag | 240 |
| actatttatt cgaagtttac ggaccattcg ttcaatttga accagatacc caagaacgtt | 300 |
| ttcgggtgta ttttcttcgc tattgatgaa caaaacaagg gatatctgac gcttaatgat | 360 |
| tggtttttatt ttaataattt attagaatat gataattatc atctcattat tctatatgag | 420 |
| ttctttagga aatttgatgt agagaatttg aaggcaaaac aaaaaaaaga gcttggtagt | 480 |
| tcgtcgttta atttaaaggc tgcagatgat cgaattaagt caattaatta tggtaacaga | 540 |
| tttctaagct tgatgatct tctttttgaat ctgaaccaat tcaaagatac tatccgcctg | 600 |
| ttgcacgaat ctattgatga taattttgtt aaagataaca aattactact tgattggaat | 660 |
| gactttcgat ttctgaaatt ttacaaatgt tatcatgaaa atgaagagta tttgagttta | 720 |
| aactctctgg tcacgatttt acaaaatgat cttaagaatg aaaaaatatt tataggtttt | 780 |
| gataggttgg cacagatgga ctcacaaggg catcgtttag ccctaagcaa aaatcaactc | 840 |
| acctatcttc taaggttatt ttactctcac agggtgtctg cagatatatt ttcctccttg | 900 |
| aatctatcaa acaccgaatt actaaaagcg acaataatt ccattccgta caatgtattc | 960 |
| aaggatatat tttatttatt tcaaaatttt gacctactga accaaatatt tcacaagtat | 1020 |
| gttactgaaa ataatttgaa tgagcaggat attagggaac aaatagttac taaaaatgac | 1080 |
| tttatgacag ttttaaacgc ccagtataac aaagtaaaca atatcattga gttctctcct | 1140 |
| tcccaaatca acctactatt ttctatcgtc gcaaattcaa aggaaacag aagattaaga | 1200 |
| aagagaaatc aagatcgaga tgacgagcta ttaaatgatc accattatga ttcagatatt | 1260 |
| gatttttta tccataatga gtatttgcat ggagtaagca gatccagaaa aaatttagaa | 1320 |
| agttttaatg actattatca tgatctctcg gatggatttg accaagactc tggtgttaaa | 1380 |

```
aaagcttcaa aagcgagtac tggcttgttt gaatctgtat ttggaggtaa aaagataaa      1440 gcaacgatgc gttctgactt aacaattgaa gatttcatga aaattttgaa cccaaattac    1500
ctgaacgact tagttcacca aatggaattg caaaaaaatc aaaatgagtc attgtatatt    1560
aattactact tttatccaat tttcgattcg ttgtacaatt tctccttggg ttctattgcg    1620
ggttgtattg gtgcaactgt agtatacccca atagacttta taaaaacaag gatgcaagcc   1680
caaagatctt tagcccaata caaaaactca attgattgtt tgttgaagat tatatcccgc    1740
gaaggaataa aaggtctcta ctctggctta gggccacaat aataggagt tgctcctgaa     1800 aaggcgataa aattgactgt caatgatttt atgagaaaca ggttgactga taaaaacggc    1860
aagctaagcc ttttttcctga aattatttct ggcgcttcag ctggtgcatg tcaagttata   1920
tttactaatc cgttagagat tgtaaaaatt aggctacagg tccaatccga ctatgttggt    1980
gaaaacatac aacaagccaa tgaaactgcc actcaaatag tcaaaaaatt aggactgagg    2040
ggcttgtaca atggtgtagc cgcatgttta atgagagatg ttccattctc tgctatttat    2100
tttcccactt atgcacattt aaaaaaagat ctctttgatt ttgatccaaa tgataaaaca    2160
aagaggaatc gattaaaaac atgggagctt ttaactgccg gtgccattgc tggtatgcca    2220 gctgcctctct tgactactcc ttttgatgtt ataaaaacaa ggctccagat agatcctcga    2280
aaaggtgaga caaagtataa cggtatattt catgctatcc gaactatctt aaaggaagag    2340
agctttagaa gcttttttcaa aggtggtgga gcccgtgtcc taagaagttc tccccaattt   2400
gggttcactc tggccgccta tgaattattc aagggcttta ttccctcccc cgataacaaa    2460
ttaaaaagca gagagggtag gaagagattt tgtatcgatg acgacgcagg caatgaagag    2520
acagtagttc atagtaacgg tgaactccca cagcaaaagt tttactctga tgatagaaaa    2580
catgccaatt attactataa aagctgtcaa attgcgaaaa cattcattga tttggacaat    2640
aacttttcta ggtttgactc ttcagtttat aaaaacttcc aagagcacct aagaagcatt    2700
aacgggtga                                                             2709

<210> SEQ ID NO 12
<211> LENGTH: 1059
<212> TYPE: DNA
<213> ORGANISM: Saccharomyces cerevisiae

<400> SEQUENCE: 12
atgacatcta tagataatag acctttgccg ttcatatacc agttcacagc cggtgccatt      60
gccggcgtct cggagctatt ggtgatgtat ccattggacg tggtgaagac aagaatgcaa    120
ttacaagtga caaccaaagg tcatcccgct gttgttgcag cgaaagcagc agtagatcac    180
tacacgggcg tgatggattg tcttacaaaa attgtgaaga aggaaggatt ttcgcatctt    240
tacaagggta tcacatcgcc tatattaatg gaggctccga aaagagcaat taagttctcc    300
ggaaacgata cattccaaac gttttataaa aagattttcc ccacgcccaa tggggagatg    360
actcaaaaaa tcgccatata cagtggtgcg tccgctggcg ccgtggaagc ctttgtcgtc    420
gcgccttttg aactagtgaa gattagatta caggatgtga attcacagtt caagacaccc    480
attgaagttg taagaatag tgttgtgaaa ggtggtgttt tgtcacttt caatgggttg       540 gaagccacta tctggagaca cgttctttgg aatgccggtt atttcggtat aatattccaa    600
attcggaagc ttttgccggc ggctaaaaca agcacggaaa agaccagaaa tgatttgatc    660
gcaggtgcta ttggtggcac tgtcgggtgc ttgttgaata caccatttga cgtggtaaaa    720
tctaggatcc aaagaagttc cgggccgctg aggaagtaca actggtccct gccttcagtg    780
```

```
ctgttagttt accgtgagga agggtttaaa gcattgtata agggatttgc gccaaaggtc    840
atgagacttg cccccggtgg tgggttattg ttggtagttt tcacgaacgt catggatttt    900
ttcagagaag tcaagtatgg taaaaaacaa tgatcctgac gctctttatt tcattttgtt    960
gtagcccgcc catacatgta tacgtatata tatatatata tttattggaa gtaaaagtaa   1020
aaaactcgct taactagcac atgtttaaac aagcgttga                          1059
```

<210> SEQ ID NO 13
<211> LENGTH: 3543
<212> TYPE: DNA
<213> ORGANISM: Saccharomyces cerevisiae

<400> SEQUENCE: 13

```
atgagcagta gcaagaaatt ggccggtctt agggacaatt tcagtttgct cggcgaaaag     60
aataagatct tggtcgccaa tagaggtgaa attccgatta gaattttttag atctgctcat   120 gagctgtcta tgagaaccat cgccatatac tcccatgagg accgtctttc aatgcacagg   180
ttgaaggcgg acgaagcgta tgttatcggg gaggagggcc agtatacacc tgtgggtgct   240
tacttggcaa tggacgagat catcgaaatt gcaagaagc ataaggtgga tttcatccat   300
ccaggttatg ggttcttgtc tgaaaattcg gaatttgccg acaaagtagt gaaggccggt   360
atcacttgga tcggccctcc agctgaagtt attgactctg tgggtgacaa agtctctgcc   420
agacacttgg cagcaagagc taacgttcct accgttcccg gtactccagg acctatcgaa   480
actgtgcaag aggcacttga cttcgttaat gaatacggct accggtgat cattaaggcc   540 gcctttggtg gtggtggtag aggtatgaga gtcgttagag aaggtgacga cgtggcagat   600
gcctttcaac gtgctacctc cgaagcccgt actgccttcg gtaatggtac ctgctttgtg   660
gaaagattct tggacaagcc aaagcatatt gaagttcaat tgttggctga taaccacgga   720
aacgtggttc atcttttcga aagagactgt tctgtgcaaa gaagacacca aaaagttgtc   780
gaagtcgctc cagcaaagac tttgccccgt gaagttcgtg acgctatttt gacagatgct   840
gttaaattag ctaaggtatg tggttacaga aacgcaggta ccgccgaatt cttggttgac   900
aaccaaaaca gacactattt cattgaaatt aatccaagaa ttcaagtgga gcataccatc   960
actgaagaaa tcaccggtat tgacattgtt tctgcccaaa tccagattgc cgcaggtgcc  1020
actttgactc aactaggtct attacaggat aaaatcacca cccgtgggtt ttccatccaa  1080
tgtcgtatta ccactgaaga tccctctaag aatttccaac cggataccgg tcgcctggag  1140
gtctatcgtt ctgccggtgg taatggtgtg agattggacg tggtaacgc ttatgcaggt  1200 gctactatct cgcctcacta cgactcaatg ctggtcaaat gttcatgctc tggttctact  1260
tatgaaatcg tccgtaggaa gatgattcgt gccctgatcg aattcagaat cagaggtgtt  1320
aagaccaaca ttcccttcct attgactctt ttgaccaatc cagttttttat tgagggtaca  1380 tactggacga cttttattga cgacacccca caactgttcc aaatggtatc gtcacaaaac  1440
agagcgcaaa aactgttaca ctatttggca gacttggcag ttaacggttc ttctattaag  1500
ggtcaaattg gcttgccaaa actaaaatca aatccaagtg tcccccatt gcacgatgct  1560 cagggcaatg tcatcaacgt tacaaagtct gcaccaccat ccggatggag acaagtgcta  1620
ctgaaaaagg gaccatctga atttgccaag caagtcagac agttcaatgg tactctactg  1680
atggacacca cctggagaga cgctcatcaa tctctacttg caacaagagt cagaaccccac  1740 gatttggcta caatcgctcc aacaaccgca catgcccttg caggtgcttt cgctttagaa  1800
```

| | |
|---|---|
| tgttggggtg gtgctacatt cgacgttgca atgagattct tgcatgagga tccatgggaa | 1860 |
| cgtctgagaa aattaagatc tctggtgcct aatattccat tccaaatgtt attacgtggt | 1920 |
| gccaacggtg tggcttactc ttcattacct gacaatgcta ttgaccattt tgtcaagcaa | 1980 |
| gccaaggata atggtgttga tatatttaga gtttttgatg ccttgaatga tttagaacaa | 2040 |
| ttaaaagttg gtgtgaatgc tgtcaagaag gccggtggtg ttgtcgaagc tactgtttgt | 2100 |
| tactctggtg acatgcttca gccaggtaag aaatacaact tagactacta cctagaagtt | 2160 |
| gttgaaaaaa tagttcaaat gggtacacat atcttgggta ttaaggatat ggcaggtact | 2220 |
| atgaaaccgg ccgctgccaa attattaatt ggctccctaa gaaccagata tccggattta | 2280 |
| ccaattcatg ttcacagtca tgactccgca ggtactgctg ttgcgtctat gactgcatgt | 2340 |
| gccctagcag gtgctgatgt tgtcgatgta gctatcaatt caatgtcggg cttaacttcc | 2400 |
| caaccatcaa ttaatgcact gttggcttca ttagaaggta acattgatac tgggattaac | 2460 |
| gttgagcatg ttcgtgaatt agatgcatac tgggccgaaa tgagactgtt gtattcttgt | 2520 |
| ttcgaggccg acttgaaggg accagatcca gaagtttacc aacatgaaat cccaggtggt | 2580 |
| caattgacta acttgttatt ccaagctcaa caactgggtc ttggtgaaca atgggctgaa | 2640 |
| actaaaagag cttacagaga agccaattac ctactgggag atattgttaa agttacccca | 2700 |
| acttctaagg ttgtcggtga tttagctcaa ttcatggttt ctaacaaact gacttccgac | 2760 |
| gatattagac gtttagctaa ttcttttgga ctttcctgact ctgttatgga cttttttgaa | 2820 |
| ggtttaattg gtcaaccata cggtgggttc ccagaaccat taagatctga tgtattgaga | 2880 |
| aacaagagaa gaaagttgac gtgccgtcca ggtttagaat tagaaccatt tgatctcgaa | 2940 |
| aaaattagag aagacttgca gaacagattc ggtgatattg atgaatgcga tgttgcttct | 3000 |
| tacaatatgt atccaagggt ctatgaagat ttccaaaaga tcagagaaac atacggtgat | 3060 |
| ttatcagttc taccaaccaa aaatttccta gcaccagcag aacctgatga agaaatcgaa | 3120 |
| gtcaccatcg aacaaggtaa gactttgatt atcaaattgc aagctgttgg tgacttaaat | 3180 |
| aagaaaactg gcaaagaga agtgtatttt gaattgaacg gtgaattaag aaagatcaga | 3240 |
| gttgcagaca gtcacaaaaa catacaatct gttgctaaac caaaggctga tgtccacgat | 3300 |
| actcaccaaa tcggtgcacc aatggctggt gttatcatag aagttaaagt acataaaggg | 3360 |
| tctttggtga aaaagggcga atcgattgct gttttgagtg ccatgaaaat ggaaatggtt | 3420 |
| gtctcttcac cagcagatgg tcaagttaaa gacgttttca ttaaggatgg tgaaagtgtt | 3480 |
| gacgcatcag atttgttggt tgtcctagaa gaagaaaccc taccccatc ccaaaaaaag | 3540 |
| taa | 3543 |

```
<210> SEQ ID NO 14
<211> LENGTH: 1440
<212> TYPE: DNA
<213> ORGANISM: Saccharomyces cerevisiae

<400> SEQUENCE: 14
```

| | |
|---|---|
| atgtcagcga tattatcaac aactagcaaa agtttcttat caaggggctc cacaagacaa | 60 |
| tgtcaaaata tgcaaaaggc tcttttttgca ctattgaatg ctcgccacta tagtagcgcc | 120 |
| tccgaacaaa cgttgaagga gagatttgct gaaattatcc cagcaaaggc agaagaaatt | 180 |
| aaaaaattca agaagaaaca cggtaaaacc gttattggtg aagttctttt ggagcaagct | 240 |
| tatggtggta tgagaggtat taaaggcctt gtttgggaag ttccgtgtt agaccccgaa | 300 |
| gaaggtatta gatttagggg tcgtactatt ccagaaattc aaagggaact accaaaggct | 360 |

-continued

```
gagggtagta cagaaccttt gccagaagct ttattttggt tgcttttgac tggtgaaata      420
cctactgacg ctcaagttaa agccctttct gctgatttag ctgccagatc agaaattcca      480
gagcacgtta tccaactttt agatagcctc ccaaaagatc tacatccaat ggcgcaattt      540
tctattgccg tgactgcttt agaaagcgag tctaagtttg ccaaagcata tgctcaaggt      600
gtatccaaga aagaatattg gagctataca tttgaagatt cgttagatct gctgggtaaa      660
ttacctgtta ttgcttccaa aatttatcgt aatgtgttca aggatggtaa aattacttca      720
accgatccta tgctgactac tggtaaaaat ttgcccaacttttgggcta cgaaaacaag        780 gattttattg acttaatgag actatatttta actattcatt ctgatcatga aggtggtaac     840
gtttctgccc atactacaca tttagtgggt tctgccttat cttcgccata cttatctttg      900
gccgctggtt tgaatggttt agctggccca ttacatggtc gtgccaatca agaagtttta      960
gaatggctat ttaaattgag agaagaagtg aaaggtgact attcaaaaga aacaattgaa     1020
aagtacttgt gggatacttt gaacgcaggg agagttgttc ctggttatgg ccatgcggtt     1080
ttgagaaaaa ctgatcctcg ttatacggct caacgtgaat tcgcattgaa acatttccca     1140
gattacgagt tatttaagtt ggtctccacc atttatgaag ttgccccagg ggttttaact     1200
aagcatggta aaactaagaa cccatggcca aatgttgatt cacattccgg tgttttattg     1260
caatactatg gtctaactga ggcttcgttc tacactgtat tgtttggtgt tgccagagct     1320
attggtgtgt taccccaatt aatcatcgat agggctgttg gtgctccaat cgaaaggcca     1380
aaatcattct ccaccgaaaa atacaaggag ttggtaaaga aaatcgaaag taagaactaa     1440
```

<210> SEQ ID NO 15
<211> LENGTH: 1263
<212> TYPE: DNA
<213> ORGANISM: Saccharomyces cerevisiae

<400> SEQUENCE: 15

```
atgcttgctg cttcattcaa acgccaacca tcacaattgg tccgcgggtt aggagctgtt       60
cttcgcactc ccaccaggat aggtcatgtt cgtaccatgg caactttaaa aacaactgat      120
aagaaggccc ctgaggacat cgagggctcg gacacagtgc aaattgagtt gcctgaatct      180
tccttcgagt cgtatatgct agagcctcca gacttgtctt atgagacttc gaaagccacc     240
ttgttacaga tgtataaaga tatggtcatc atcagaagaa tggagatggc ttgtgacgcc     300
ttgtacaagg ccaagaaaat cagaggtttt tgccatctat ctgttggtca ggaggccatt     360
gctgtcggta tcgagaatgc catcacaaaa ttggattcca tcatcacatc ttacagatgt     420
cacggtttca cttttatgag aggtgcctca gtgaaagccg ttctggctga attgatgggt     480
agaagagccg tgtctctta tggtaagggt ggttccatgc acctttacgc tccaggcttc     540
tatggtggta atggtatcgt gggtgcccag gttcctttag gtgcaggttt agcttttgct     600
caccaataca gaacgagga cgcctgctct ttcactttgt atggtgatgg tgcctctaat     660
caaggtcaag ttttttgaatc tttcaacatg gccaaattat ggaatttgcc cgtcgtgttt     720
tgctgtgaga caacaagta cggtatgggt accgccgctt caagatcctc cgcgatgact     780
gaatatttca agcgtggtca atatattcca ggtttaaaag ttaacggtat ggatattcta     840
gctgtctacc aagcatccaa gtttgctaag gactggtgtc tatccggcaa aggtcctctc     900
gttctagaat atgaaaccta taggtacggt ggccattcta tgtctgatcc cggtactacc     960
tacagaacta gagacgagat tcagcatatg agatccaaga acgatccaat tgctggtctt    1020
```

| | |
|---|---|
| aagatgcatt tgattgatct aggtattgcc actgaagctg aagtcaaagc ttacgacaag | 1080 |
| tccgctagaa aatacgttga cgaacaagtt gaattagctg atgctgctcc tcctccagaa | 1140 |
| gccaaattat ccatcttgtt tgaagacgtc tacgtgaaag gtacagaaac tccaacccta | 1200 |
| agaggtagga tccctgaaga tacttgggac ttcaaaaagc aaggttttgc ctctagggat | 1260 |
| taa | 1263 |

<210> SEQ ID NO 16
<211> LENGTH: 2337
<212> TYPE: DNA
<213> ORGANISM: Saccharomyces cerevisiae

<400> SEQUENCE: 16

| | |
|---|---|
| atgctgtctg cacgttctgc catcaagaga cccattgttc gtggtcttgc gacagtctcc | 60 |
| aacttgacta gagattcaaa agtcaaccaa aacttattag aagatcattc ttttattaac | 120 |
| tacaagcaga atgtgaaaac gctggatatc gtaagaaaaa gattaaacag gccatttacc | 180 |
| tacgcggaaa agattttgta cggtcacttg gatgaccctc atggtcaaga tattcagaga | 240 |
| ggtgttcat acctaaaatt aagaccagat cgtgttgcct gtcaagatgc tactgctcaa | 300 |
| atggctattt acaatttat gtccgctggt ttaccacagg ttgctaagcc agtcactgtc | 360 |
| cactgtgacc atttgattca agcacaagtt ggtggtgaaa agatttgaa gagagctata | 420 |
| gatctaaaca aggaagttta tgatttcttg gcctctgcca ctgcgaaata taacatgggt | 480 |
| ttctggaagc caggttccgg tatcattcac caaattgttc tggaaaacta cgctttccca | 540 |
| ggtgctttga tcattggtac tgactccat acaccaaatg ctggtggttt aggtcaattg | 600 |
| gctattggtg ttggtggtgc tgatgccgtt gatgttatgg caggtcgtcc atgggaattg | 660 |
| aaggctccaa agatcttagg tgttaagttg actggtaaga tgaacggttg gacttctcca | 720 |
| aaggatatta ttttgaaatt ggctggtatc acaactgtca aaggtggtac tggtaaaatt | 780 |
| gttgaatatt tcggtgatgg tgttgacacc ttctccgcta ctggtatggg taccattgt | 840 |
| aatatgggtg ctgaaatcgg tgctaccaca tctgttttcc cattcaacaa atctatgatt | 900 |
| gaatatttgg aagcaactgg tcgtggtaag atcgctgact tgctaaattt ataccacaag | 960 |
| gacctattat ctgctgataa ggatgctgaa tacgatgagg tcgtcgaaat tgacttgaac | 1020 |
| actctggaac catacatcaa tgggccattt acccccgatt ggctactcc agttctaag | 1080 |
| atgaaggaag ttgctgttgc taataactgg ccattggatg tcagagtcgg tttgatcggt | 1140 |
| tcttgtacca attcctctta tgaagatatg tctcgttcag catccattgt caaggatgct | 1200 |
| gctgctcatg gttttgaaatc caagaccatt ttcactgtta ctccaggttc tgaacaaatc | 1260 |
| agagccacta ttgaacgtga tgccaattga gaaaccttca aagaatttgg tggtatcgtt | 1320 |
| ttggcaaacg cctgtggccc atgtattggt caatgggatc gtagagatat caagaaaggt | 1380 |
| gacaagaata ctatcgtttc ctcttacaac agaaatttca cttctagaaa tgatggtaac | 1440 |
| ccacaaactc atgcttttgt tgcatctcca gaattagtaa ctgcgttcgc cattgcgggt | 1500 |
| gatttgagat tcaaccctct aacagacaaa ttaaggaca aggatggtaa tgagttcatg | 1560 |
| ttgaaaccac cacatggtga tggttttgcct caaagaggtt atgatgctgg tgagaacact | 1620 |
| taccaagctc cacctgcaga ccgtagcacc gttgaagtta agtttctcc aacttcagac | 1680 |
| cgtctacaac tgttgaaacc attcaaacct tgggatggta aggatgctaa agacatgcca | 1740 |
| atcttgatta aggccgtcgg taagacaact actgatcata tttctatggc tggtccatgg | 1800 |
| ttgaaataca gaggtcattt agaaaacatt tctaataact atatgattgg tgctattaat | 1860 |

```
gctgaaaaca agaaggctaa ctgtgttaaa aatgtatata ctggtgaata caaaggtgtt    1920
ccagacactg ctagagatta cagagaccaa ggtatcaagt gggttgttat tggtgatgaa    1980
aactttggtg aaggttcctc tcgtgaacac gctgctttgg aaccaagatt cttgggcggt    2040
ttcgctatca tcacaaagtc tttcgctcgt atccatgaaa ctaacttgaa aaacaaggt     2100 ctattgccat tgaacttcaa gaacccagct gactatgaca agatcaaccc tgatgacaga    2160
atcgatattc tgggtctagc tgaattggct ccaggtaagc ctgtaacaat gagagttcat    2220
ccaaagaatg gtaagccatg ggatgctgtg ttgacccata ctttcaacga tgagcaaatt    2280
gaatggttca atatggttc tgccttaaat aaaattaagg ccgatgagaa gaaataa       2337
```

<210> SEQ ID NO 17
<211> LENGTH: 1287
<212> TYPE: DNA
<213> ORGANISM: Saccharomyces cerevisiae

<400> SEQUENCE: 17

```
atgagtatgt tatctagaag attattttcc acctctcgcc ttgctgcttt cagtaagatt      60
aaggtcaaac aacccgttgt cgagttggac ggtgatgaaa tgacccgtat catttgggat     120
aagatcaaga agaaattgat tctaccctac ttggacgtag atttgaagta ctacgactta     180
tctgtcgaat ctcgtgacgc cacctccgac aagattactc aggatgctgc tgaggcgatc     240
aagaagtatg gtgttggtat caaatgtgcc accatcactc tgatgaagc tcgtgtgaag     300 gaattcaacc tgcacaagat gtggaaatct cctaatggta ccatcagaaa cattctcggc     360
ggtacagtgt tcagagagcc cattgtgatt cctagaattc ctagactggt cccacgttgg     420
gaaaaaccaa tcattattgg aagacacgcc cacggtgatc aatataaagc tacgacaca     480 ctgatcccag gcccaggatc tttggaactg gtctacaagc catccgaccc tacgactgct     540
caaccacaaa ctttgaaagt gtatgactac aagggcagtg gtgtggccat ggccatgtac     600
aatactgacg aatccatcga agggtttgct cattcgtctt tcaagctggc cattgacaaa     660
aagctaaatc ttttcttgtc aaccaagaac actattttga agaaatatga cggtcggttc     720
aaagacattt tccaagaagt ttatgaagct caatataaat ccaaattcga caactaggg     780 atccactatg aacaccgttt aattgatgat atggtcgctc aaatgataaa atctaaaggt     840
ggctttatca tggcgctaaa gaactatgac ggtgatgtcc aatctgacat cgtcgctcaa     900
ggatttggct ccttaggttt gatgacttct atcttagtta caccagacgg taaaactttc     960
gaaagtgaag ctgctcatgg taccgtgaca agacattata gaaagtacca aaagggtgaa    1020
gaaacttcta caaactccat tgcatccatt ttcgcgtggt cgagaggtct attgaagaga    1080
ggtgaattgg acaatactcc tgctttgtgt aaatttgcca atattttgga atccgccact    1140
ttgaacacag ttcagcaaga cggtatcatg acgaaggact tggctttggc ttgcggtaac    1200
aacgaaagat ctgcttatgt taccacagaa gaatttttgg atgccgttga aaaagacta    1260 caaaagaaa tcaagtcgat cgagtaa                                         1287
```

<210> SEQ ID NO 18
<211> LENGTH: 393
<212> TYPE: DNA
<213> ORGANISM: Saccharomyces cerevisiae

<400> SEQUENCE: 18

```
atgtctcaac cggttcaacg cgctgcagca cgctcattcc ttcaaaaata catcaataaa     60
```

```
gaaactttga aatatatttt cacaacacac ttctggggtc ccgtatcaaa tttcggtatc    120
ccaattgctg ctatatatga tctgaaaaaa gaccctacac taatctctgg cccaatgact    180
tttgctttag ttacctattc aggtgttttc atgaagtatg ctctttcagt atcacccaaa    240
aactacttac tgtttggatg ccaccttatt aatgaaactg cgcaattagc tcaaggctat    300
aggtttctca atacacgta tttcacaaca gatgaggaga agaaagctct agataaggaa     360
tggaaagaga agaaaaaac tggtaaacag taa                                  393

<210> SEQ ID NO 19
<211> LENGTH: 390
<212> TYPE: DNA
<213> ORGANISM: Saccharomyces cerevisiae

<400> SEQUENCE: 19
atgtctacat catccgtacg ttttgcattt aggcggttct ggcaaagtga gacaggcccc    60
aagacggtgc atttctgggc tcctactttg aaatggggtc tggttttcgc tggattcagc    120
gatatgaaga gaccggtgga aaaaatttct ggtgctcaaa atttgtcgct gctatctact    180
gcgctgattt ggactcgttg gtcctttgtc atcaagccaa gaaacatctt gttggcttct    240
gtcaactcgt ttctttgtct gaccgctggc tatcaattgg gtagaattgc caactacagg    300
atacggaatg gcgactctat atcgcaattg tgtagctata ttctcagcgg cgccgacgaa    360
agcaaaaagg aaattactac gggcagataa                                     390

<210> SEQ ID NO 20
<211> LENGTH: 441
<212> TYPE: DNA
<213> ORGANISM: Saccharomyces cerevisiae

<400> SEQUENCE: 20
atgtcagcat cagcttttaa ttttgccttt agaagatttt ggaatagtga acaggccct     60 aaaacagtac acttctgggc cccaactttg aagtgggggc tggtcttcgc agggctaaat    120
gatattaaga ggcctgttga aaggtatca ggagcacaaa atttatcttt attagcgacg     180
gcactgattt ggacgcgttg gtcgtttgtc atcaagccca agaactatct gttagcttcc    240
gtcaattttt tcctggggttg cactgcaggc taccatctaa caagaattgc taactttagg    300
atacggaacg gtgattcttt taaacaggtt attcactaca taataaaagg ggagactcct    360
gcagccgtcg cagcaaagca aactgcatcc acatcgatga caaaggtgt gatcggtact     420 aatccgccaa taacgcactg a                                              441

<210> SEQ ID NO 21
<211> LENGTH: 1542
<212> TYPE: DNA
<213> ORGANISM: Saccharomyces cerevisiae

<400> SEQUENCE: 21
atgctatcga agaatttgta tagtaacaag aggttgctca cctcgacgaa tacgctagtc    60
agattcgctt ccaccagatc cacagggtg gaaaactccg gagcaggtcc tacatctttt    120
aagaccatga agtcattga ccctcagcac agcgacaaac caaacgtgct gatactgggt    180
tcggggtggg gagctatttc gttttaaag cacattgaca ccaagaagta caacgtttcc    240
atcatctctc ctagaagcta tttcttattt acgcctttgt taccttctgc accagttggg    300
acagtagacg aaaagtcaat tattgagccc atcgttaatt ttgctctcaa gaaaagggg    360 aacgttacct actatgaggc agaagccacc tctatcaatc ccgacaggaa taccgttacc    420
```

```
ataaaatcat tatctgccgt tagccagcta taccaacctg aaaaccatct agggctgcat      480
caagcagaac ctgctgaaat taagtacgat tatttaatca gtgctgtagg tgcggaacct      540
aacacatttg gtattcctgg ggtcactgat tacggtcatt tcctgaagga aattcccaac      600
tctttggaaa taagaagaac ttttgccgcc aatctagaga aggctaactt attgccaaag      660
ggtgatcccg aaagaagaag actactgtcc attgtcgtgg ttggtggtgg gcctactggt      720
gtagaggccg ctggtgaact acaggattat gttcaccagg acctgagaaa gtttctccct      780
gcattggccg aagaagtcca aattcacttg gtcgaagctc tgcccatcgt tttgaatatg      840
tttgagaaaa agctttcatc atacgcgcaa tcacatttag aaaacacttc gatcaaagta      900
catctgagaa cggctgtcgc caaagttgaa gaaaagcaat tgttggcaaa gaccaaacac      960
gaagacggta aataaccga agaaactatt ccatacggta ctttgatttg gccacgggt      1020 aacaaggcaa gaccggtaat cactgacctt tcaagaaaaa ttcctgagca aaactcgtcc     1080
aagagaggat tggcagtgaa tgactttttg caggtgaaag gcagcaacaa catttttcgcc    1140 attggtgaca atgcatttgc tgggttgcca ccaaccgccc aagtagcgca ccaagaggcc     1200
gaatatttgg ccaagaattt tgataaaatg gctcaaatac caaatttcca aaagaatcta     1260
tcttcaagaa aggataaaat tgatctcttg ttcgaggaga caactttaa acctttcaaa     1320 tacaacgatt taggtgcctt agcatacctg ggatccgaaa gggccattgc aaccatacgt    1380
tccggtaaga gaacatttta caccggtggt ggcttaatga ccttctactt atggagaatt    1440
ttgtacttgt ccatgattct atctgcaaga tcgagattaa aggtcttttt cgactggatt    1500
aaattagcat ttttcaaaag agacttttt aaaggattat ag                        1542
```

<210> SEQ ID NO 22
<211> LENGTH: 1302
<212> TYPE: DNA
<213> ORGANISM: Saccharomyces cerevisiae

<400> SEQUENCE: 22

```
atgtttgttt caccaccacc agcaacttcg aaaaaccaag ttttacaacg acgtccatta       60
gaatcgacta acagtaatca tgggtttgca agctccctac aggccattcc ggaaaacacg     120
atgagtggca gtgataatgc ttcttttcaa agtttgccac tatcaatgag tagctctcaa     180
tccacgactt cttcgagaag agagaacttt gtgaatgctc ctccggagta cactgataga    240
gctagagatg agattaaaaa aagattattg gcctcctcac ctagcagaag gtcacatcat    300
tcaagcagta tgcattcagc gagcaggaga tcaagcgtgg ctgaaagtgg gagtttactt    360
tcggataatg cctcgtctta tcaatcaagt atattttctg ccccctctac tgtgcacacg    420
caactaacta atgactcttc gttctccgaa tttcctaacc acaagttaat cacgagagtg    480
agcctggatg aagcattacc caaaacgttt tatgacatgt attcgccaga tattctatta    540
gcagacccat ccaacattct ctgtaacggg cgtcccaagt ttaccaagag agagttattg    600
gattgggatt taaacgatat aagatcgtta ttgatagtcg agaagttaag gcccgaatgg    660
ggtaatcaac taccggaagt aataacggtg ggtgataata tgccccagtt taggttacaa    720
ttattaccac tatattctag cgatgagacc ataatcgcaa cgttagtcca ttcggatctg    780
tacatggagg ctaacttaga ttatgaattc aaactaacca gcgccaaata tacagtagcg    840
accgctagaa aaagacatga gcatataact ggtagaaatg aagccgtcat gaatttgtcg    900
aaaccggaat ggagaaatat catcgaaaat tacctcttaa atatagcagt agaggcacaa    960
```

| | |
|---|---|
| tgcaggtttg atttcaaaca aagatgctcc gaatataaga aatggaagtt acaacagtcc | 1020 |
| aacttaaaaa gaccggacat gccccccacca agcataatac cgcggaaaaa cagcacagaa | 1080 |
| acaaaatcgc ttctgaaaaa ggctttattg aagaacattc agttgaaaaa ccccaataat | 1140 |
| aaccttgatg aattgatgat gagatcaagc gccgcaacaa atcaacaggg aaaaaacaaa | 1200 |
| gtcagcttat ctaaagaaga aaaggctacg atatggtcgc aatgtcaggc acaagtttac | 1260 |
| caaagattag gattggattg gcagccggat tcagtatcct ga | 1302 |

```
<210> SEQ ID NO 23
<211> LENGTH: 1332
<212> TYPE: DNA
<213> ORGANISM: Escherichia coli

<400> SEQUENCE: 23
```

| | |
|---|---|
| atggtaaagg aacgtaaaac cgagttggtc gagggattcc gctattcggt tccctatatc | 60 |
| aatacccacc ggggaaaaac gtttgtcatc atgctcggcg gtgaagccat tgagcatgag | 120 |
| aatttctcca gtatcgttaa tgatatcggg ttgttgcaca gcctcggcat ccgtctggtg | 180 |
| gtggtctatg gcgcacgtcc gcagatcgac gcaaatctgg ctgcgcatca ccacgaaccg | 240 |
| ctgtatcaca gaatatacg tgtgaccgac gccaaaacac tggaactggt gaagcaggct | 300 |
| gcgggaacat tgcaactgga tattactgct cgcctgtcga tgagtctcaa taacacgccg | 360 |
| ctgcagggcg cgcatatcaa cgtcgtcagt ggcaatttta ttattgccca gccgctgggc | 420 |
| gtcgatgacg gcgtggatta ctgccatagc gggcgtatcc ggcggattga tgaagacgcg | 480 |
| atccatcgtc aactgacag cggtgcaata gtgctaatgg ggccggtcgc tgtttcagtc | 540 |
| actggcgaga gctttaacct gacctcggaa gagattgcca ctcaactggc catcaaactg | 600 |
| aaagctgaaa agatgattgg ttttttgctct tcccagggcg tcactaatga cgacggtgat | 660 |
| attgtctccg aacttttccc taacgaagcg caagcgcggg tagaagccca ggaagagaaa | 720 |
| ggcgattaca actccggtac ggtgcgcttt ttgcgtggcg cagtgaaagc ctgccgcagc | 780 |
| ggcgtgcgtc gctgtcattt aatcagttat caggaagatg gcgcgctgtt gcaagagttg | 840 |
| ttctcacgcg acggtatcgg tacgcagatt gtgatgaaa cgccgagca gattcgtcgc | 900 |
| gcaacaatca acgatattgg cggtattctg gagttgattc gcccactgga gcagcaaggt | 960 |
| attctggtac gccgttctcg cgagcagctg gagatgaaa tcgacaaatt caccattatt | 1020 |
| cagcgcgata acacgactat tgcctgcgcc gcgctctatc cgttcccgga agagaagatt | 1080 |
| ggggaaatgg cctgtgtggc agttcacccg gattaccgca gttcatcaag gggtgaagtt | 1140 |
| ctgctggaac gcattgccgc tcaggcgaag cagagcggct taagcaaatt gtttgtgctg | 1200 |
| accacgcgca gtattcactg gttccaggaa cgtggattta ccccagtgga tattgattta | 1260 |
| ctgccccgaga gcaaaaagca gttgtacaac taccagcgta atccaaagt gttgatggcg | 1320 |
| gatttagggt aa | 1332 |

```
<210> SEQ ID NO 24
<211> LENGTH: 777
<212> TYPE: DNA
<213> ORGANISM: Escherichia coli

<400> SEQUENCE: 24
```

| | |
|---|---|
| atgatgaatc cattaattat caaactgggc ggcgtactgc tggatagtga agaggcgctg | 60 |
| gaacgtctgt ttagcgcact ggtgaattat cgtgagtcac atcagcgtcc gctggtgatt | 120 |
| gtgcacggcg gcggttgcgt ggtggatgag ctgatgaaag gctgaatct gccggtgaaa | 180 |

```
aagaaaaacg gcctgcgggt gacgcctgct gatcagatag acattatcac cggagcactg    240
gcgggaacgg caaataaaac cctgttggca tgggcgaaga acatcagat tgcggccgta     300 ggtttgtttc tcggtgacgg cgacagcgtc aaagtgaccc agcttgatga agagttaggt    360
catgttggac tggcgcagcc aggttcgcct aagcttatca actccttgct ggagaacggt    420
tatctgccgg tggtcagctc cattggcgta acagacgaag gcaactgat gaacgtcaat     480 gccgaccagg cggcaacggc gctggcggca acgctgggcg cggatctgat tttgctctcc    540
gacgtcagcg gcattctcga cggcaaaggg caacgcattg ccgaaatgac cgccgcgaaa    600
gcagaacaac tgattgagca gggcattatt actgacggca tgatagtgaa agtgaacgcg    660
gcgctggatg cggcccgcac gctgggccgt ccggtagata tcgcctcctg gcgtcatgcg    720
gagcagcttc cggcactgtt taacggtatg ccgatgggta cgcggatttt agcttaa      777
```

<210> SEQ ID NO 25
<211> LENGTH: 1074
<212> TYPE: DNA
<213> ORGANISM: Corynebacterium glucuronolyticum

<400> SEQUENCE: 25

```
atgataatgc acaatgtcta tggtgttaca atgactatta aggtcgcaat cgcaggtgcc    60
tcaggttacg caggtggtga aatcttgaga ttgttattgg gtcatccagc atatgcctct   120
ggtgaattag aaataggtgc attgaccgct gcatccactg ccggtagtac attgggtgaa   180
ttgatgccac atattcctca attagctgat agagttatac aagacactac agctgaaaca   240
ttggcaggtc atgatgttgt cttttaggt ttgccacacg gtttctcagc agaaatagcc    300
ttacaattgg gtcctgatgt cacagtaatc gattgtgccg ctgactttag attacaaaat   360
gcagccgact gggaaaaatt ctatggttcc gaacatcaag gtacctggcc atacggtatt   420
ccagaaatgc ctggtcacag agaagccttg agaggtgcta agagagttgc agtcccaggt   480
tgctttccta caggtgctac cttagcatta ttgccagccg ttcaagctgg tttgatcgaa   540
cctgatgtat ctgtagtttc aattaccggt gtttccggtg caggtaaaaa ggctagtgtt   600
gccttattgg gttctgaaac tatgggttca ttgaaggcat acaacacctc aggtaaacat   660
agacacactc cagaaatcgc tcaaaacttg ggtgaagttt ctgacaaacc agtaaaggtt   720
tcattcacac ctgtttttagc tccattgcct agaggtattt taaccactgc tacagcacct   780
ttgaaagaag gtgtcaccgc cgaacaagcc agagctgttt acgaagaatt ctacgctcaa   840
gaaactttcg tccatgtatt accagaaggt gcccaacctc aaacacaagc tgttttgggt   900
tccaacatgt gtcacgttca agtcgaaatt gatgaagaag ctggtaaagt attggttact   960
agtgcaatcg acaatttgac taagggtaca gcaggtgctg cagttcaatg catgaactta  1020
tctgtcggtt ttgatgaagc cgctggtttg ccacaagtcg gtgtagctcc ttaa        1074
```

<210> SEQ ID NO 26
<211> LENGTH: 1176
<212> TYPE: DNA
<213> ORGANISM: Corynebacterium glucuronolyticum

<400> SEQUENCE: 26

```
atgtctacat tggaaacctg gcctcaagtc atcatcaaca catacggtac tcctcctgtc    60
gaattggtct ctggtaaagg tgctacagta accgatgacc agggtaacgt ttacatcgat   120
ttgttggctg gtatagcagt taacgccttg ggtcatgctc acccagcaat aatcgaagct   180
```

```
gtaactaacc aaataggtca attgggtcat gtttctaact tatttgcatc aagacctgtt       240
gtcgaagttg ccgaagaatt aattaagaga ttctcttgg atgacgcaac attagctgca        300
caaaccagag ttttcttttg taattcaggt gcagaagcca acgaagccgc ttttaaaatc       360
gctagattga caggtagatc cagaattta gcagccgttc atggtttcca cggtagaacc        420
atgggtagtt tggcattaac tggtcaacca gataagagag aagcatttt gccaatgcct        480 tccggtgttg aattctatcc ttacggtgac actgactatt tgagaaaaat ggtcgaaacc       540
aatccaactg atgtagctgc aatctttta gaacctattc aaggtgaaac aggtgtagtt       600
ccagcccctg aaggtttctt gaaggctgtt agagaattgt gtgatgaata cggtatcttg      660
atgatcactg acgaagtaca aacaggtgtt ggtagaaccg gtgactttt cgcacatcaa       720 cacgatggtg tcgtaccaga cgttgtcact atggctaaag gtttgggtgg tggtttacct     780
attggtgcct gcttggctac aggtagagcc gctgaattaa tgaccccagg taaacatggt     840
actacatttg gtggtaaccc tgttgcttgt gcagccgcta agcagtctt gtcagtagtt      900 gatgacgcat tttgcgccga agttgctaga aagggtgaat tattcaagga attgttggct    960
aaggttgatg tgtcgtaga cgtcagaggt agaggtttga tgttaggtgt tgtcttggaa    1020
agagatgtcg caaagcaagc cgtattggac ggttttaaac acggtgttat tttaaatgct  1080
ccagcagata acatcattag attgactcca cctttagtca taacagatga agaaattgcc   1140
gacgctgtta aagcaattgc cgaaacaata gcttaa                             1176
```

<210> SEQ ID NO 27
<211> LENGTH: 1167
<212> TYPE: DNA
<213> ORGANISM: Corynebacterium glucuronolyticum

<400> SEQUENCE: 27

```
atggccgaaa aagtataac agctccaaaa ggtttcgttg cctctgctac tacagccggt         60
atcaaggctt caggtaatcc agatatggca ttggttgtca accaaggtcc tgaattttct       120
gctgcagccg tttttcactag aaatagagtc tttgctgcac ctgttaaagt ctctagagaa      180
aacgttgctg atggtcaaat tagagctgtc ttgtataatg ctggtaatgc aaacgcctgt      240
aacggtttac aaggtgaaaa ggatgcaaga gaatccgtaa gtcatttggc ccaaaatttg      300
ggtttagaag attccgacat cggtgtttgc agtacaggtt tgattggtga attgttgcca      360
atggataagt tgaacgctgg tatcgaccaa ttgaccgccg aaggtgcttt aggtgacaac      420
ggtgccgctg cagccaaagc tatcatgacc actgataccg ttgacaagga aactgtagtt     480
tttgcagatg gttggacagt aggtggtatg ggtaaaggtg ttggtatgat ggcaccttca     540
ttggccacca tgttagtatg tttaacaacc gatgcctccg ttactcaaga aatggctcaa    600
attgctttgg caaatgccac cgctgtcact ttcgacacat tagatataga cggttctaca    660
tcaaccaacg atactgtttt cttgttagca tctggtgcct caggtatcac tccaacacaa    720
gatgaattga atgacgctgt ttacgctgca tgctctgata ttgccgctaa attcaagca     780 gacgccgaag gtgttacaaa gagagtagca gttaccgtcg taggtactac aaataacgaa   840
caagctatta atgcagccag aacagttgca agagataact tgtttaaatg tgccatgttc   900
ggttctgacc caaattgggg tagagtctta gctgcagttg gtatggctga tgcagacatg   960
gaacctgaaa agatatccgt cttttcaac ggtcaagctg tatgcttgga tagtactggt   1020
gctcctggtg caagagaagt cgacttgtct ggtgctgata ttgacgttag aatagatttg   1080
ggtacttcag gtgaaggtca agcaacagtt agaaccactg atttgtcctt tagttacgtc   1140
```

```
gaaattaatt ccgcttactc ttcataa                                           1167
```

<210> SEQ ID NO 28
<211> LENGTH: 1071
<212> TYPE: DNA
<213> ORGANISM: Pichia anomala

<400> SEQUENCE: 28

```
atgtatccta cttctggttg tgctagagtt ttgatggctt gtcctgctcc tgctatgttg     60
agaggtcctt tgttgagacc ttccactact gctattagag gtttgagagg ttccccattg    120
ttatatcatt acgctgcaac ttccaatagt aacatgagat actttcttc aacatccaga     180
agatggatca agaattttt cgcaccacct aaggaaacag atcatatagt agaaagtgtt    240
actcatgga acaccctgt tttcaccgaa aaacaaatga aggaaattgc tatagcacat     300
agagaagcta agaattggtc tgattgggtt gcattaggta cagtcagatt tttgagatgg    360
gctacagact tagcaaccgg ttacagacac gccgctccag gtaaacaagg tgttgaagtc    420
cctgaacaat tccaaatgac cgaaagaaag tgggttatca gattcatttt cttggaaact    480
gtcgctggtg taccaggtat ggttggtggt atgttgagac attgagatc tttgagaaga    540
atgaagagag ataacggttg gattgaaacc ttgttagaag aagcatataa cgaaagaatg    600
cacttgttat cattttgaa attggcccaa ccaggttggt tcatgagatt aatggtattg     660
ggtgctcaag gtgttttctt taacggtttc tttatctctt acttgatctc acctagaaca    720
tgtcatagat ttgtcggtta tttggaagaa gaagcagtaa tgacctacac tcacgccata    780
aaagatttgg aatctggtaa attgccaaat tgggccaacc aaccagctcc tgacattgcc    840
gttgcttatt ggcaaatgcc tgaaggtaaa agaactatat ggatttgtt gtactacata    900
agagcagacg aagccaagca tagagaagtt aatcacacat tagcaaactt gaaacaaggt    960
gtcgatccaa atccttatgc agccaagtac gacaacccag aagcccctca tcctactaag   1020
tcagcagaaa ttgtcaagcc tacaggttgg gaaagagacg aagttatcta a            1071
```

<210> SEQ ID NO 29
<211> LENGTH: 1401
<212> TYPE: DNA
<213> ORGANISM: Saccharomyces cerevisiae

<400> SEQUENCE: 29

```
atgtctagta ctcaagtagg aaatgctcta tctagttcca ctactacttt agtggacttg     60
tctaattcta cggttacccca aaagaagcaa tattataaag atggcgagac gctgcacaat    120
cttttgcttg aactaaagaa taaccaagat ttggaacttt taccgcatga acaagcgcat    180
cctaaaatat ttcaagcgct caaggctcgt attggtagaa ttaataatga aacgtgcgac    240
cccggtgagg agaactcgtt tttcatatgc gatttgggag aagtcaagag attattcaac    300
aactgggtga aggagcttcc tagaattaag ccatttttatg ccgtcaaatg taatcctgat    360
accaaggttt tgtcattatt agcagagttg ggcgttaatt tcgattgcgc ttccaaagtg    420
gaaattgaca gagtattatc gatgaacatc tcgccggata gaattgttta cgctaatcct    480
tgtaaagtag catctttcat tagatatgca gcttcaaaaa atgtaatgaa gtctactttt    540
gacaatgtag aagaattgca taaaatcaaa aagtttcatc ctgagtctca gttgttatta    600
agaatcgcta ccgatgactc taccgctcaa tgtcgacttt ccaccaaata tggctgtgaa    660
atggaaaacg tagacgtttt attaaaggct ataaaggaac taggtttaaa cctggctggt    720
```

```
gtttctttcc acgtcggttc aggcgcttct gattttacaa gcttatacaa agccgttaga    780
gatgcaagaa cggtatttga caaagctgct aacgaatacg ggttgccccc tttgaagatt    840
ttggatgtag gtggtggatt tcaatttgaa tccttcaaag aatcaactgc tgttttgcgt    900
ctagcgctag aggaattttt ccctgtaggt tgtggtgttg atataattgc agagcctggc    960
agatactttg tagctacagc gttcactttg gcatctcatg tgattgcgaa gagaaaactg   1020
tctgagaatg aagcaatgat ttacactaac gatggtgtat acgggaacat gaattgtatt   1080
ttattcgatc atcaagagcc ccatccaaga acccttatc ataatttgga atttcattac    1140
gacgattttg aatccactac tgcggtcctc gactctatca acaaaacaag atctgagtat   1200
ccatataaag tttccatctg ggacccaca tgtgatggtt tggattgtat tgccaaagag    1260
tattacatga agcatgatgt tatagtcggt gattggtttt attttcctgc cctgggtgcc   1320
tacacatcat cggcggctac tcaattcaac ggctttgagc agactgcgga tatagtatac   1380
atagactctg aactcgattg a                                             1401
```

<210> SEQ ID NO 30
<211> LENGTH: 1191
<212> TYPE: DNA
<213> ORGANISM: Saccharomyces cerevisiae

<400> SEQUENCE: 30

```
atgactgtca ccataaaaga attgactaac cacaactaca ttgaccacga actatcagcc     60
actttagact caacggatgc gttcgagggt cccgagaagt tgctggaaat ctggttcttc    120
cctcacaaga agtccatcac gaccgaaaag acattaagaa atattggcat ggatagatgg    180
atcgagattt tgaaattagt gaaatgcgaa gttctttcca tgaagaagac taagaactg     240 gatgcctttt tgttgagtga gtcttccctc ttcgtcttcg atcacaaatt gacgatgaag    300
acgtgcggta ctacaaccac attgttctgt ctcgaaaagc ttttccagat cgttgagcaa    360
gagttatcgt gggctttccg cacaacacaa gggggcaagt acaaaccatt taaagtgttt    420
tattctagac gatgtttcct tttcccctgt aagcaagccg ctatccatca aaactgggct    480
gacgaagtcg actatttgaa caaatttttc gacaatggta aaagttattc cgtgggaaga    540
aatgacaaga gcaaccactg gaacctgtac gtcaccgaga cggaccgctc cacacctaag    600
ggaaaggagt acatcgagga tgacgacgaa actttcgaag tactgatgac ggagctggac    660
ccagaatgcg ctagtaagtt tgtttgcggg cctgaggcat ccacaaccgc tctcgtggag    720
ccaaacgaag ataagggcca caacctcggc taccaaatga ctaaaaatac aaggcttgac    780
gaaatatatg tcaactcggc ccaagactcc gatttatcat ttcaccacga tgcatttgcg    840
ttcacgccat gtggatactc atccaatatg attctcgctg aaaaatacta ttacaccctg    900
cacgtgactc cggaaaaggg ttggtcttac gcctctttcg aaagtaacat accgtatt    960 gacatttccc aagggaagca agacaacttg gacgttcttc tacatattct gaacgttttt   1020
caaccaagag agttctcgat gaccttttt accaaaaatt atcagaacca atccttccaa    1080
aaactactaa gcatcaacga gtcactgccc gactacatca gttagacaa aattgtttat    1140 gatctggacg actaccacct tttctatatg aaattgcaga agaaaatatg a             1191
```

<210> SEQ ID NO 31
<211> LENGTH: 882
<212> TYPE: DNA
<213> ORGANISM: Saccharomyces cerevisiae

<400> SEQUENCE: 31

```
atggcacaag aaatcactca cccaactatt gtagacggct ggttcagaga aatttctgat      60
accatgtggc caggccaggc catgacttta aaagtggaga agttttaca ccatgagaag     120
tcaaaatatc aagacgtttt gatcttcaaa tccactacat atggtaatgt tctagtttta    180
gataatgtaa ttcaagccac cgaaagggat gaatttgcct accaagaaat gattgcccat   240
cttgccttga attcccatcc aaatcctaag aaggttcttg ttattggtgg gggtgatggt   300
ggtgttttga gagaggttgt caagcatgat tccgttgagg aagcctggtt atgtgacatt   360
gatgaagctg ttattagact atcaaaggag tacctaccag aaatggctgc ctcttattct   420
cacccaaagg ttaagaccca cattggtgat ggttttccaat tttaagaga ttaccaaaac   480
acatttgacg taatcattac tgactcttct gacccagaag gtccagctga aaccctttc    540
caaaaggaat atttccaatt gttgaacagt gcgttgacga aaaagggtgt aatcactaca   600
caagcagaaa gtatgtggat tcacttgcca atcattaagg acttaaagaa agcctgttct   660
gaagttttcc cagttgcaga atactctttc gttactattc caacttaccc aactggtacg   720
attggtttta tggtttgctc caaagataaa acttgcaatg tcaagaagcc actacgtgaa   780
atctctgatg agaaggaggc tgaattatac agatactata caagaaaat tcacgaagct    840
tcctttgttc taccaacctg ggcagccaag gaattaaatt ag                      882
```

<210> SEQ ID NO 32
<211> LENGTH: 1761
<212> TYPE: DNA
<213> ORGANISM: Saccharomyces cerevisiae

<400> SEQUENCE: 32

```
atgtcggatc attctcccat ttctaataag gaaaatcatc tgctgccatc agactcgtca    60
agaagctcat ccagcgatat gcattcgacg ggcaccacgg gaaccacagg cgtcgaacct   120
gtagatttca ccggtgaagg tgccaaatac acaactgcta cggagggcaa tggtggtgca   180
gatttagcga ttcaaagaac gacgactatg aattctgctg cagaatcaga ggttaatatc   240
acgagaagat taactaaaat ccttactggg tctgttaacg agcctgaccg tgtagaggtt   300
gattataccaa attgtcgcc catgggtggt gacagacctt accctccatc gttgccgagc   360
agagacctgt acgaggttac ttttgatggt cctaacgacc cactacatcc atttaactgg   420
cccatgaaga gaaagtgct gctatgtctg gtcttatgtc tggattctat tgccattgct   480
atgtgttctt ccattttgc ctctgcagtg ccgcaaatct gcgagatata ccacgtcatc   540
gaagttgtcg ccattttggg tatcacgctt tttgttcttg ggtttgcggc ctcaccggtt   600
atctatgctc ctctttctga attgtacggt agaaagggtg ttctggtttt atctgcgttt   660
ggatttgccc ttttccaatt tgctgtcgct actgctgaga acctgcaaac tatttcata    720
tgtagattct tggtggtttt atcggggca gcacccatgg ccgtcgtccc cgccgcgttt   780
gccgacatgt tgatactaa tgttagaggt aaagccattg cgctattttc tctaggtgtt   840
tttgtaggcc ccatttttatc gcctgtcatg ggttcttata tcgcacaaag aactacctgg   900
agatggttag aatatgttgt cggttgtttc gcttccgcag ttttcgttgc catcgtattg   960
ttctttgaag aaacacatca ccctaccatt ttggttaaca aggccaaaca gatgagaaag   1020
caaagtaata actggggtat tcatgctgct catgaagacg tggagctatc catcaaagac   1080
attgtccaaa aaactgtgac gaggcctatc attatgcttt tcgtggaacc attgctacta   1140
ttcgtgacta tttacaactc ttttgtctac ggtatcttgt atttgttact ggaagcctac   1200
```

```
ccacttgtct tgtgtggaggg ttatgggttt actgaaaacg gtgagttgcc atacatcgcc    1260
ttgattatcg gtatgatggt gtgtgctgct ttcatttggt atatggacaa cgattatttg    1320
aaaagatgta gagccaaggg gaaattagtg cccgaggcca gattgtacgc aatggtcatt    1380
gcaggtaccg ttttccctat tggtatctta tggttctgtt ggacgggcta ctatcctcac    1440
aagattcatt ggatggtccc cacagtagga ggggccttca tcgggttcgg tttaatgggt    1500
attttcttgc catgttttaaa ctatatcatt gaatcgtatc tattgttggc agcttctgcc    1560
gtcgcagcaa acactttcat gaggtctgca tttggtgcat gcttcccatt gtttgcagga    1620
tatatgttcc gtggcatggg tatcggttgg gctggtttgt tattaggtct atttgccgct    1680
gcgatgattc ccgtgccttt actattctta aaatatggtg aatctatcag aaagaaatcc    1740
aagtatgctt acgccgctta a                                              1761

<210> SEQ ID NO 33
<211> LENGTH: 1857
<212> TYPE: DNA
<213> ORGANISM: Saccharomyces cerevisiae

<400> SEQUENCE: 33
atgccagagt atacgctact ggctgataat ataagggaga atatcgttca tttcgatccg      60
aatggtttgt ttgataactt gcacaccatt gttcatgaag atgacagtca agagaacgag    120
gaggccgagc atttcaatta tgatcaggtg ttggataaat cgttattgtc aagaggttct    180
attgtcggtc tcggtttagg actaatgagt cccgttttag gaatgtgcac tagtatggcc    240
attgggctaa ttaatggtgg tccgttaact ataatgctag ttttttaat cagtggagtg    300 tgtatatggt tttcgtcgct ttctcttggt gagattgttt caaaatttcc gatggaactg    360
catgttggga gtgccatgtt ggccccggag aaattgaaat tagtatgttc gtggtacact    420
ggctggttaa tgctcatagg gaattggact atgagtacca gtattacttt tgcaggcgct    480
caacttacca tttctttgat tctgatgacg aactccaacc taatatccga ggcacacttg    540
attttttaca cagtcattgt attttactta gttgtgactg ttgtaggcct cgtgaatttg    600
aaatttgcaa gatttattga aacaataaac aaagtctgtg tttattggat catatatgcc    660 attatatta ttgatattct tctactagta ttccacaaag gtaaatttcg atctttgaag    720
tacgcgctat ttcactttga taataatcta tcagggtata aaagcgcatt tctttccttc    780
atcattggat ccaacagtc taatttcacg ttacaaggtt tcagtatgtt acctgcttta    840
gctgacgaag tcaaagttcc tgagaaggat attccacgtg gtatgtcgaa tgcggtattg    900
ttatccgcgt tctctggagt cattttttctt ataccaataa tgttaatcct gccagataat    960
gatttgcttt ttaccaatca taaggttcta ccaatagtga acattttttac aaaatcgact   1020 gattcggtgg tcttgtcttt tttttagtg ctcctaattt taggaaactt actgttttcc   1080
ggaattggct cgattactac atcttctcgt gcggtatata gttttagtcg tgaccaggct   1140
ataccatact acgataaatg gacctacgtc gaaccggatt ctcagtcaaa agtccccaag   1200
aattctgttg tattgagtat gataatatca tacttttag gtctgctagc tttgattca   1260 acggccgcat ttaatgcttt tataggcgct gcagtgctct gtcttgttc tgcgactttc   1320 attccgttag tcttggtgct gtttacgaga agaagagcta tccgaagcgc gccagtaaaa   1380
atcaggtata agtttggttg gttcatcaac attgttcta ttgtgtggct cttgttatct   1440
atggtttctg ttttgcctacc aacgcaagtg cctgtaactt tcaaaacaat gaattatgct   1500
ttaatggtgt acgtattctg cattttagtt atcactggtc tttatttcaa atggggaag   1560
```

```
tataatttta gattacccct ggcagatgac atcaaggctc caattcccag tgatgcggaa    1620
gaaactgttt ttgaactaga ggatagcaat gttgaacata ctctaaactc gggaaccaca    1680
gtgaaagagt ctgtagaaaa taattctgaa gaaggtttca tcaaggtgca tcctaaaagt    1740
agtacagaaa atcccttttga ggaaaatgag gaaaacgtga taaccgatta tggtgatgag    1800
caccatacag cagaacaaga atttgatctt gccgatgatc gtagatatga tatatga      1857
```

<210> SEQ ID NO 34
<211> LENGTH: 1017
<212> TYPE: DNA
<213> ORGANISM: Saccharomyces cerevisiae

<400> SEQUENCE: 34

```
atgtcaacca cagcatccac gccttcatct ttacgtcatt tgatttctat aaaagatctt      60
tctgatgaag aattcagaat cttagtacaa agagctcaac atttcaagaa tgtttttaaa     120
gcaaataaaa cgaatgattt ccaatccaac catctgaaac tattgggtag aactatagcc     180
ttaatattta ctaaaagatc aactagaacg agaatttcga ccgaaggtgc agccaccttc     240
tttggtgccc aaccgatgtt tttaggtaaa gaggatattc agcttggtgt caatgaatca     300
ttttacgata ccaccaaggt tgtatcatct atggtttcat gtattttttgc ccgtgtgaac     360 aaacatgaag acatacttgc tttttgcaag gattcctctg taccgatcat caactctcta     420
tgtgacaaat tccaccccttt gcaagcaatt tgtgatcttt taacaataat cgaaaacttc     480
aatatatctc tagatgaagt aaataaggga atcaattcaa aattgaagat ggcatggatt     540
ggtgatgcca ataatgtcat aaatgatatg tgcatcgcat gtctgaaatt cggtataagt     600
gtcagtattt ccactccccc cggtattgaa atggattccg atattgtcga tgaagcaaag     660
aaagttgctg agagaaacgg tgcgacattt gaattaacac acgactcttt aaaggcctcc     720
accaatgcca atatattagt aaccgatact ttcgtttcca tgggtgaaga atttgcgaaa     780
caggccaagc tgaaacaatt caaaggtttt caaatcaatc aagaacttgt ctctgtggct     840
gatccaaact acaaatttat gcattgtctg ccaagacatc aagaagaagt tagtgatgat     900
gtcttttatg gagagcattc catagtcttt gaagaagcag aaaacagatt atatgcagct     960
atgtctgcca ttgatatctt tgttaataat aaaggtaatt tcaaggactt gaaataa      1017
```

<210> SEQ ID NO 35
<211> LENGTH: 1263
<212> TYPE: DNA
<213> ORGANISM: Saccharomyces cerevisiae

<400> SEQUENCE: 35

```
atgtctaagg gaaaagtttg tttggcttat tctggtggtt tagatacctc cgtcattttg      60
gcttggctac tagaccaagg ctacgaagtt gtagctttca tggctaatgt agggcaagaa     120
gaagatttcg atgccgccaa ggaaaaggcc ttgaagatcg tgcctgcaa gttcgtttgt     180 gtggattgtc gtgaagattt tgtcaaggat attctattcc cagctgtaca ggtcaacgct     240
gtgtacgaag acgtttatct gttgggtacc tctttggcaa gacctgttat tgccaaagcc     300
caaattgacg tcgctaaaca ggagggctgt ttcgcggtct ctcatggttg taccggtaaa     360
ggtaatgatc aaatcagatt cgaattgtca ttttacgctc tgaagccaga cgttaagtgt     420
attacaccat gggagaatgcc tgaattttc gaaagatttg ctggcagaaa ggatttgtta     480
gactatgctg cacaaaaggg tattcccgtc gcccaaacca aggccaagcc atggtctact     540
```

```
gacgaaaacc aagcccacat ttcttacgag gcaggtatct tggaagaccc agataccacc    600
ccaccaaagg acatgtggaa attgatcgtc gatccaatgg atgctccgga ccaaccacaa    660
gatttgacca ttgactttga acgtggtctt ccagtcaagt tgacctacac cgacaacaag    720
acttccaagg aagtttccgt taccaagcct ttggatgttt tcttggccgc atccaactta    780
gcaagggcca acggtgttgg tagaatcgat attgtagaag atcgttacat taacttgaaa    840
tccagaggtt gttacgaaca ggctccattg actgttttga gaaaagctca tgttgatttg    900
gaaggtttga ctttagacaa agaagtccgt caattgagag actcattcgt cacaccaaac    960
tactccagat tgatatataa cggttcctac ttcaccccag agtgtgagta catcagatct   1020
atgatccaac atcccaaaa tagcgttaac ggtactgtca gggttagact gtataagggt   1080
aacgtcatca ttctgggcag atctacaaag actgaaaagt tgtacgatcc gacagaatcc   1140
tctatggatg agttgaccgg tttcttacct accgatacca ccggtttcat tgccatccag   1200
gccattagaa ttaaaaaata cggtgaatcc aaaaaaacca aggtgaagaa gttgactttg   1260
taa                                                                 1263

<210> SEQ ID NO 36
<211> LENGTH: 1392
<212> TYPE: DNA
<213> ORGANISM: Saccharomyces cerevisiae

<400> SEQUENCE: 36
atgtcagacg gcactcaaaa actatggggt gggagattca ctggtgaaac cgatcctttg     60
atgcaccttt acaatgcgtc tcttccgtat gattataaga tgtataaggc agatttagaa    120
ggaactaaag tatacacagc gggcttgcag aagttgggtc ttctaacgga gacagaattg    180
gcaaagatcc atgaaggttt ggctgaaatc aaaaaagaat gggacgctga caaatttgtc    240
cgtcatccaa cgacgagga tatccatact gcgaatgaaa gacgtcttgg tgaactaatt    300
ggccgcgata ttgctggtaa agtccacacc ggtagatccc gtaatgatca agttgttacc    360
gatttgagaa tatactgtcg tgacattgtc aatgacaccc tctttccagc tttaaagggc    420
ttggttgaag ttctaattaa gagggccgaa ggtgagatag atgtcttaat gccaggctac    480
acacatttac aaagggcaca acctattaga tggtctcatt ggttgagctc ttatgcaaca    540
tacttcaccg aagattacaa gagactgggt caaatactac acagattgaa tcaatcacca    600
ctgggtgcag gcgctcttgc tggtcatcct tacggcattg atagagaatt tttggctgaa    660
ggtttgggtt tcaatagtgt aattggtaac tccttggttg ctgttttctga tagagatttc    720 atcgtggagt tgatgttttg gggaactttg ttcatgaacc atatttctcg ttttgctgaa    780
gatttgatta tatattgtac agcagaattt ggtttcatac agttgagcga cgcctattca    840
acaggttctt ctttaatgcc tcagaagaag aatgcagact cgttagagtt gttaagaggt    900
aaatccggta gagtatttgg tgatctgaca ggattcttga tgagtttgaa gggtatccca    960
tctacttatg ataaagacat gcaagaagac aaagagccac tattcgattg cttaacaact   1020
gtagagcact ccatgctgat tgccacaggt gttatttcta ccttaactgt aaataaggaa   1080
aagatggaag ctgctctcac gatggatatg ctagctaccg acttggcaga ttacttggtc   1140
agaaagggtg ttccattcag agagactcat cacatatctg gtgagtgtgt cgctactgct   1200
gaaagacttg gtctaagcgg tattgataaa ttaccttgg agcagtatca aaagatcgat   1260
tcgagattcg gacaagatct ttttgaaact tttaactttg aacaaagcgt tgaaagacga   1320
gatgctactg gtggaaccgc taaatctgct gtattgaagc aattggataa tttgaaatcc   1380
```
caattaaatt ag 1392

<210> SEQ ID NO 37
<211> LENGTH: 1977
<212> TYPE: DNA
<213> ORGANISM: Escherichia coli

<400> SEQUENCE: 37

| | | | | | |
|---|---|---|---|---|---|
| atgtctgacg | acatgtctat | gggtttgcct | tcgtcagcgg | gcgaacacgg | tgtactacgc | 60 |
| tccatgcagg | aggttgcaat | gagctcccag | gaagccagca | agatgctgcg | tacttacaat | 120 |
| attgcctggt | ggggcaataa | ctactatgac | gttaacgagc | tgggccacat | tagcgtgtgc | 180 |
| ccggacccgg | acgtcccgga | agctcgcgtc | gatctcgcgc | agttagtgaa | aactcgtgaa | 240 |
| gcacagggcc | agcgtctgcc | tgcactgttc | tgtttcccac | agatcctgca | gcaccgtttg | 300 |
| cgttccatta | acgccgcgtt | caaacgtgcg | agggaatcct | acggctataa | cggcgattac | 360 |
| ttccttgttt | atccgatcaa | agttaaccag | caccgccgcg | tgattgagtc | cctgattcat | 420 |
| tcgggcgaac | cgctgggtct | ggaagccggt | tccaaagccg | agttgatggc | agtactggca | 480 |
| catgctggca | tgacccgtag | cgtcatcgtc | tgcaacggtt | ataaagaccg | cgaatatatc | 540 |
| cgcctggcat | taattggcga | agatgtgggg | cacaaggtct | atctggtcat | tgagaagatg | 600 |
| tcagaaatcg | ccattgtgct | ggatgaagca | gaacgtctga | atgtcgttcc | tcgtctgggc | 660 |
| gtgcgtgcac | gtctggcttc | gcagggttcg | ggtaaatggc | agtcctccgg | cggggaaaaa | 720 |
| tcgaagttcg | gcctggctgc | gactcaggta | ctgcaactgg | ttgaaaccct | gcgtgaagcc | 780 |
| gggcgtctcg | acagcctgca | actactgcac | ttccacctcg | gttcgcagat | ggcgaatatt | 840 |
| cgcgatatcg | cgacaggcgt | tcgtgaatcc | gcgcgtttct | atgtggaact | gcacaagctg | 900 |
| ggcgtcaata | ttcagtgctt | cgacgtcggc | ggcggtctgg | gcgtggatta | tgaaggtact | 960 |
| cgttcgcagt | ccgactgttc | ggtgaactac | ggcctcaatg | aatacgccaa | caacattatc | 1020 |
| tgggcgattg | gcgatgcgtg | tgaagaaaac | ggtctgccgc | atccgacggt | aatcaccgaa | 1080 |
| tcgggtcgtg | cggtgactgc | gcatcacacc | gtgctggtgt | ctaatatcat | cggcgtggaa | 1140 |
| cgtaacgaat | acacggtgcc | gaccgcgcct | gcagaagatg | cgccgcgcgc | gctgcaaagc | 1200 |
| atgtgggaaa | cctggcagga | gatgcacgaa | ccgggaactc | gccgttctct | gcgtgaatgg | 1260 |
| ttacacgaca | gtcagatgga | tctgcacgac | attcatatcg | gctactcttc | cggcatcttt | 1320 |
| agcctgcaag | aacgtgcatg | ggctgagcag | ctttatttga | gcatgtgcca | tgaagtgcaa | 1380 |
| aagcagctgg | atccgcaaaa | ccgtgctcat | cgtccgatta | tcgacgagct | gcaggaacgt | 1440 |
| atggcggaca | aaatgtacgt | caacttctcg | ctgttccagt | cgatgccgga | cgcatggggg | 1500 |
| atcgaccagt | tgttcccggt | tctgccgctg | gaagggctgg | atcaagtgcc | ggaacgtcgc | 1560 |
| gctgtgctgc | tggatattac | ctgtgactct | gacggtgcta | tcgaccacta | tattgatggt | 1620 |
| gacggtattg | ccacgacaat | gccaatgccg | gagtacgatc | cagagaatcc | gccgatgctc | 1680 |
| ggtttcttta | tggtcggcgc | atatcaggag | atcctcggca | acatgcacaa | cctgttcggt | 1740 |
| gataccgaag | cggttgacgt | gttcgtcttc | cctgacggta | gcgtagaagt | agaactgtct | 1800 |
| gacgaaggcg | ataccgtggc | ggacatgctg | caatatgtac | agctcgatcc | gaaaacgctg | 1860 |
| ttaacccagt | tccgcgatca | agtgaagaaa | accgatcttg | atgctgaact | gcaacaacag | 1920 |
| ttccttgaag | agttcgaggc | aggtttgtac | ggttatactt | atcttgaaga | tgagtaa | 1977 |

<210> SEQ ID NO 38

<211> LENGTH: 921
<212> TYPE: DNA
<213> ORGANISM: Escherichia coli

<400> SEQUENCE: 38

```
atgagcacct aggtcatca atacgataac tcactggttt ccaatgcctt tggtttttta      60
cgcctgccga tgaacttcca gccgtatgac agcgatgcag actgggtgat tactggcgtg     120
ccgttcgata tggccacttc tggtcgtgcg ggtggtcgcc acggtccggc agcgatccgt     180
caggtttcga cgaatctggc ctgggaacac aaccgcttcc cgtggaattt cgacatgcgt     240
gagcgtctga cgtcgtgga ctgcggcgat ctggtatatg cctttggcga tgcccgtgag     300
atgagcgaaa agctgcaggc gcacgccgag aagctgctgg ctgccggtaa gcgtatgctc     360
tctttcggtg gtgaccactt tgttacgctg ccgctgctgc gtgctcatgc gaagcatttc     420
ggcaaaatgg cgctggtaca cttttgacgcc cacaccgata cctatgcgaa cggttgtgaa     480
tttgaccacg gcactatgtt ctataccgcg ccgaaagaag gtctgatcga cccgaatcat     540
tccgtgcaga ttggtattcg taccgagttt gataaagaca acggctttac cgtgctggac     600
gcctgccagg tgaacgatcg cagcgtggat gacgttatcg cccaagtgaa acagattgtg     660
ggtgatatgc cggtttacct gacttttgat atcgactgcc tggatcctgc ttttgcacca     720
ggcaccggta cgccagtgat tggcggcctg acctccgatc gcgctattaa actggtacgc     780
ggcctgaaag atctcaacat tgttgggatg acgtagtgg aagtggctcc ggcatacgat      840
cagtcggaaa tcactgctct ggcagcggca acgctggcgc tggaaatgct gtatattcag     900
gcggcgaaaa agggcgagta a                                              921
```

<210> SEQ ID NO 39
<211> LENGTH: 795
<212> TYPE: DNA
<213> ORGANISM: Escherichia coli

<400> SEQUENCE: 39

```
atgaaaaaac tgaaactgca tggctttaat aatctgacca aaagtctgag tttttgtatt      60
tacgatatct gctacgccaa aactgccgaa gagcgcgacg gttatattgc ttatatcgat     120
gaactctata atgccaaccg tctgaccgaa atcctgtcag aaacctgttc cattatcggg     180
gctaatattc ttaacatcgc ccgccaggat tacgaaccac agggtgccag cgtcactatt     240
ctggtgagtg aagaaccggt tgacccgaaa ctcatcgaca aaacagaaca ccccggccca     300
ctgccagaaa cggtcgttgc ccatctcgat aaaagtcata tttgcgtaca tacctacccg     360
gaaagtcatc ctgaaggcgg tttatgtacc ttccgcgccg atattgaagt ctctacctgc     420
ggcgtgattt ctccgctgaa ggcgctgaat tacctgatcc accagcttga gtccgatatc     480
gtaaccattg attatcgcgt gcgcggtttt acccgcgaca ttaacggtat gaagcacttt     540
atcgaccatg agattaattc gattcagaac tttatgtctg acgatatgaa ggcgctgtat     600
gacatggtgg atgtaaacgt ctatcaggaa atatcttcc ataccaagat gttgcttaaa      660
gagttcgacc ttaagcacta catgttccac accaaaccgg aagatttaac cgacagcgag     720
cgccaggaaa ttaccgctgc gctgtggaaa gaaatgcgcg agatttatta cgggcgcaat     780
atgccagctg tttaa                                                     795
```

<210> SEQ ID NO 40
<211> LENGTH: 366
<212> TYPE: DNA
<213> ORGANISM: Escherichia coli

<400> SEQUENCE: 40

```
atgtatattt attggatttt attaggtctg gctattgcta cagaaattac cggtacgctg      60
tcaatgaaat gggcgagcgt cagtgaggga aatggcggct ttatttaat gctggtgatg     120
atttctctgt cgtatatatt tctctctttc gccgttaaaa aaatcgcctt aggcgtagct    180
tatgcgctgt gggaaggtat cggtatttta tttattacct tgtttagcgt tttgttattc    240
gacgaaagtt tatcgctgat gaaaattgcc gggttaacca ccctggtcgc cgggattgtg    300
ttgataaaat caggtacccg taaagcgcgt aaacctgaac tggaggtgaa ccatggcgca    360
gtttga                                                                366
```

<210> SEQ ID NO 41
<211> LENGTH: 330
<212> TYPE: DNA
<213> ORGANISM: Escherichia coli

<400> SEQUENCE: 41

```
atggcgcagt ttgaatgggt tcacgccgcc tggctggcat ggcaatcgt gctggaaatc      60
gttgctaacg tctttttgaa attttctgac ggctttcgtc gcaaaatatt tggcttgctc    120
tccctggcgg cggtgctggc tgcctttagt gcgctttctc aagccgttaa agggatcgac    180
ttgtctgtcg cttatgcatt gtgggcggg tttggtattg ccgccacgtt agccgcaggt    240
tggatcttgt ttggtcaacg gttaaatcgt aaaggctgga ttggcctggt cttgctgttg    300
gctggaatga tcatggtgaa acttgcctga                                      330
```

<210> SEQ ID NO 42
<211> LENGTH: 1203
<212> TYPE: DNA
<213> ORGANISM: Bacillus subtilis

<400> SEQUENCE: 42

```
atgaaaaaat caataaatga gcaaaaaacg atattcatta tactattaag caacatcttc      60
gtagcatttc ttggtatcgg tttaatcatt ccagttatgc cttcttttat gaaaatcatg    120
catttatccg gcagcacaat gggttatctt gttgcggctt ttgccatttc tcagttaatt    180
acttcacctt ttgcaggtag gtgggttgac cgtttcggga gaaaaaaaat gattattctc    240
gggttgctta tattcagttt atctgagttg attttcggat tagggaccca tgtttcaata    300
tttatttct cgaggatatt gggtggtgta agtgcggctt ttatcatgcc gcggtaaca    360
gcatatgtag ctgatattac aaccctaaag gaaaggtcaa aggctatggg gtatgtttct    420
gctgcaatta gcaccggctt tattattgga cctggtgcgg gaggatttat tgccggcttt    480
ggtatccgca tgccgttttt cttcgcctcc gccatcgcgt taatagcagc tgtcacttcc    540
gttttttatac taaaagagtc attgtcgata gaagaacgcc atcaactctc atctcataca    600
aaggaatcaa atttcattaa agacttgaag agatccattc atcctgtcta tttcattgca    660
tttattatcg tctttgtaat ggcttttggt ttatcagctt atgaaacggt attcagcttg    720
ttttctgatc ataaaatttgg cttcacacca aaagatattg cagccattat tacgattagt    780
tccattgttg cggtagttat tcaagtttta ctattcggga aattggtcaa caaacttgga    840
gagaaaagaa tgattcagct gtgcttaata accggtgcga tcttggcttt cgtgtctact    900
gttatgtcag attttttaac tgttttgctt gtaacttgtt ttattttctt ggcgttcgat    960
ttgctacgtc cggccttaac cgctcatttta tccaatatgg ccggtaacca gcagggtttc   1020
```

| | |
|---|---|
| gtagcaggca tgaactccac atacaccagc ctgggaaata tatttggacc tgctctaggc | 1080 |
| ggtatactat ttgatcttaa cattcattat cctttccttt ttgcaggttt cgttatgatt | 1140 |
| gtcggccttg gtcttacaat ggtttggaaa gaaaaaaaga atgatgctgc agctttgaat | 1200 |
| taa | 1203 |

<210> SEQ ID NO 43
<211> LENGTH: 903
<212> TYPE: DNA
<213> ORGANISM: Saccharomyces cerevisiae

<400> SEQUENCE: 43

| | |
|---|---|
| atggttaata attcacagca tccttacatc aaagatggat ggtttagaga gattaatgat | 60 |
| aaaagttttc cgggccaggc ctttactatg accgtggact caatacttta tgaagcccgc | 120 |
| agtgaatttc aggacatctt aatcttccgt aacaaggtat acggtactgt tttggtcctc | 180 |
| gatggtattg tccaatgtac ggaatttgat gagtttgcct atcaagagat gatcacccac | 240 |
| attgccatgt ttgcgcattc taatcccaag cgtgtactta tcattggcgg tggggacgga | 300 |
| ggtgtcttaa gggaagtagc caagcacagc tgtgtagaag atatcactat ggtagaaatt | 360 |
| gactcatcag tgatcgaatt atcccgtaag ttcttgccca cattgagtaa tggtgctttc | 420 |
| gatgacgaaa ggttggactt gaaactttgc gatggcttca gttcttaca agatataggt | 480 |
| gcttccgacg tccataagaa atttgacgtc attattacag atagttctga tcctgaaggt | 540 |
| ccagctgaag cgttttttca agagaggtat ttcgaactat tgaaagatgc tttaaatcct | 600 |
| aatggcgttg ttattatgca aagctctgaa aattttggt taaatttaaa atacttacat | 660 |
| gatttgaaaa atacagccaa aaaggtattt cctaatacag aatattgcta taccatggtt | 720 |
| ccaacctata catctggcca attaggttta attgtttgca gtaataacgc caatataccg | 780 |
| ttgaacattc cgcaaagaaa gatatctgag caagaacaag ggaagctgaa gtactataat | 840 |
| cctcaaatac attctagtgc gtttgttttg cctacttggg cagacaaggt cattaatgaa | 900 |
| tga | 903 |

<210> SEQ ID NO 44
<211> LENGTH: 2136
<212> TYPE: DNA
<213> ORGANISM: Escherichia coli

<400> SEQUENCE: 44

| | |
|---|---|
| atgaaatcaa tgaatattgc cgccagtagt gaactggtat cccgactttc ttctcatcgt | 60 |
| cgcgtggtgg cgttgggaga tactgatttt acggacgtcg cggcagtcgt cattaccgct | 120 |
| gcggatagtc gcagtggcat tcttgcgttg cttaagcgca ccggttttca tctaccggtg | 180 |
| tttttgtatt ccgaacatgc tgttgaatta cctgcgggcg ttacggcggt aatcaacggc | 240 |
| aacgagcagc agtggctgga gctggaatcc gcagcctgtc agtatgaaga gaatttgctg | 300 |
| ccaccgtttt atgacacgct gacgcagtac gttgagatgg caacagcac ctttgcttgc | 360 |
| cctggacatc aacatggtgc gttttttaaa agcatcctg ccggacgcca ttttacgat | 420 |
| ttctttggtg agaacgtctt tcgcgccgat atgtgtaacg ctgacgtaaa attgggcgat | 480 |
| ctgcttattc atgaaggatc ggcgaaagat gcgcagaaat cgcagccaa agtctttcat | 540 |
| gccgataaaa cctattttgt gctgaacggc acatcggcag cgaataaagt ggtgacgaat | 600 |
| gcgctgttaa cgcgtggcga tctggtgctc ttcgaccgta caaccatag gtcgaatcat | 660 |
| cacggcgcgc tgattcaggc gggggcgacg ccggtctatc tggaagcttc acgcaacccg | 720 |

| | |
|---|---:|
| tttggtttca ttggcggtat tgatgcgcac tgttttaatg aagagtatct gcgccagcaa | 780 |
| attcgcgacg ttgcgccaga aaaagccgac ctgccgcgcc cgtatcgcct ggcgattatt | 840 |
| cagctgggaa cctatgacgg cactgtctat aacgcccgtc aggtgatcga taccgttggg | 900 |
| catctgtgtg attacattct gtttgattcc gcgtgggtcg gttatgaaca atttatcccg | 960 |
| atgatggcgg atagctcgcc gctgctgtta gaacttaacg aaaacgatcc ggggatcttt | 1020 |
| gtgactcagt cggtgcacaa acagcaggcg ggattctcac agacgtcgca gatccataaa | 1080 |
| aaagataacc atatccgcgg acaggcgcgt ttttgcccgc ataagcggtt gaataacgcc | 1140 |
| tttatgctcc atgcttctac cagcccttc tatccgctgt tgctgcact ggatgttaac | 1200 |
| gccaaaattc atgaagggga gagtgggcgt cggctgtggg ctgagtgtgt tgagataggg | 1260 |
| attgaagcgc gcaaggctat tcttgcgcgc tgtaagctgt tccgcccgtt tatcccgccc | 1320 |
| gttgttgatg gcaaattgtg gcaggattat ccgacatcag tgttagccag cgaccgccgt | 1380 |
| tttttcagtt ttgagccggg ggcgaagtgg cacggctttg aaggatatgc cgcggatcag | 1440 |
| tattttgttg atccgtgcaa gctgttactc actacaccag gtatcgatgc cgaaaccggc | 1500 |
| gaatatagcg actttggcgt tccggcgacg attctggcgc actatctgcg tgagaacggc | 1560 |
| attgtgccgg agaagtgcga tctcaactcc attctgtttt tattaactcc ggcggaaagc | 1620 |
| cacgagaagc tggcacaact ggtggcgatg ctggcgcaat ttgaacagca tattgaggat | 1680 |
| gactcgccgc tggttgaggt gttgccgagc gtttataaca agtatccggt gcgctatcgc | 1740 |
| gactacaccc tgcgccagtt gtgtcaggag atgcacgatc tgtatgtcag tttcgacgtc | 1800 |
| aaagacctac aaaaagcgat gttccgccag cagagtttcc cgtcagtggt gatgaacccc | 1860 |
| caggatgcgc atagcgctta tattcgcggt gacgtggagt tggtgcggat tcgtgatgcc | 1920 |
| gaagggcgaa ttgcggcaga agggcgttg cctatccac ctggcgtgct ttgcgtggta | 1980 |
| cccggggaag tctggggtgg ggcggttcaa cgttatttcc ttgcactgga agaaggggtg | 2040 |
| aatttgttgc cgggattttc gccggagctg caaggtgttt atagcgaaac cgatgcggat | 2100 |
| ggcgtgaaac ggttgtacgg ttatgtgttg aagtaa | 2136 |

<210> SEQ ID NO 45  
<211> LENGTH: 1542  
<212> TYPE: DNA  
<213> ORGANISM: Corynebacterium glucuronolyticum

<400> SEQUENCE: 45

| | |
|---|---:|
| atgtctgatt taggacccat ctggcgctgg ctgttattag tttccgtctc catttgtgcg | 60 |
| gcatcggggc tggtctatga gctagccctg gtatcgcttt ccaccagctt gaacggtggc | 120 |
| ggaattgtag aaacctccct catcgtcgca ggttatgtag ctgcccttgg acttggtgca | 180 |
| ctgctggtca agccgtttct caactggcct gcgcaaacct tcctcggtgt ggaaaccctc | 240 |
| cttggactta ttggtggttg ttccgcgctg gtgctgtatt tcaccttcgc gaccatcggc | 300 |
| caatccctgt ggattctggt gattgccacc gctgcaattg gcatcctggt cggcgctgaa | 360 |
| cttccactgc tgatgaccat gatccagcaa ggccgcctcg ccgacgccaa aaccacagga | 420 |
| tctctggttg ccaccttgaa tgctgctgat taccttggcg cacttttagg tggcctggcc | 480 |
| tggccttttg tgttgctgcc gtggcttggc atgatgcgcg gtgccgcagc agccggaatg | 540 |
| atcaaccctcg ttcagcacact attcgtgggc gtgtgctgc tgcgacattt gcttccgcgc | 600 |
| acccacttct tcgtatccgt ggtggcgctt cttctcgcga tcgcagcgct agccaccgtg | 660 |

```
ttggtgaaat ccgacgggat cgttgccacc gcccgcgcac agctctaccg cgaccccgtg      720
atctattcac accaatctga ctaccaagac atcgtagtga cagaacgagg caaagaccga      780
cgcctctacc tcaatggcgg tttgcagtat tccactcgtg accagcatag atatacagaa      840
tcactggtgt atccaagcct taatccagag gcagaatcgg tgttaatcat cggcggtggc      900
gatggcctcg cagcacggga actcctccga ttcccatcaa tgcagatcac ccaagttgaa      960
ttagacccag aagtcatcga agtagccaac acagtgctgc gctctgacaa tgggggagcg     1020
atggaagatc cccgcgtctc catcatcgtt gacgacgctt tcacctggct gcgctccggc     1080
ggaaataatg gcgaaactta cgattccatc atcatcgatc ttcccgaccc aaacaacgac     1140
accatggcca ggctgtattc agaagagttc tacaccttgg cccgagcacg actgaacgaa     1200
caaggccgca tggtggtgca atcctccagc gcctacacca ctccagatgt gttctggcga     1260
gttggagcaa ccttgaaatc ggcgggctgt gaacaagtca tcccatatca cgtgcatgtt     1320
cccacatttg gcgactgggg cttccaactg tgtggccctg ccgacatgga attagagctt     1380
cgggaagaca ccccgccact gactttcctt aatgatgaag ttctggtggc tgctggggtg     1440
tttgggttgg ataatcagcc tcgtgaattg gaaccttcca cgctggatca tccccgcgtg     1500
gtggaggatc tgcgcaaggg ataccgcgaa tcaggcgact ag                        1542
```

<210> SEQ ID NO 46
<211> LENGTH: 401
<212> TYPE: PRT
<213> ORGANISM: Campylobacter jejuni

<400> SEQUENCE: 46

```
Met Lys Asn Leu Leu Ile Ile Gly Ala Gly Val Ser Arg Val Ala
1               5                   10                  15

Thr Val Lys Cys Ala Met Asn Ser Asp Thr Phe Ser Lys Ile Thr Leu
            20                  25                  30

Ala Ser Arg Thr Lys Ser Lys Cys Asp Glu Ile Ala Ala Phe Ile Lys
        35                  40                  45

Glu Arg Leu Gly Val Gln Ile Glu Thr Ala Gln Ile Asp Ala Asp Asp
    50                  55                  60

Ser Asn Ala Val Val Glu Leu Ile Lys Lys Thr Gly Ala Gln Ile Leu
65                  70                  75                  80

Leu Asn Val Ala Leu Pro Tyr Gln Asp Leu Ser Leu Met Asp Ala Cys
                85                  90                  95

Ile Lys Ala Gly Ile Asp Tyr Val Asp Thr Ala Asn Tyr Glu His Pro
            100                 105                 110

Asp Leu Ala Lys Phe Glu Tyr Lys Glu Gln Trp Ala Arg Asn Asp Glu
        115                 120                 125

Phe Lys Gln Ala Gly Ile Leu Gly Leu Leu Gly Ser Gly Phe Asp Pro
    130                 135                 140

Gly Val Thr Asn Val Phe Cys Ala Tyr Ala Gln Gln Asn Leu Phe Asp
145                 150                 155                 160

Glu Ile Ser Tyr Ile Asp Ile Leu Asp Cys Asn Ala Gly Asp His Gly
                165                 170                 175

Tyr Ala Phe Ala Thr Asn Phe Asn Pro Glu Ile Asn Leu Arg Glu Val
            180                 185                 190

Ser Ala Lys Gly Arg Tyr Trp Glu Asn Gly Lys Trp Ile Glu Thr Gln
        195                 200                 205

Pro Met Glu Ile Lys Met Glu Trp Asp Tyr Pro Glu Val Gly Val Lys
    210                 215                 220
```

```
Asp Ser Tyr Leu Leu Tyr His Glu Glu Leu Glu Ser Leu Val Lys Asn
225                 230                 235                 240

Ile Lys Gly Leu Lys Arg Ile Arg Phe Phe Met Thr Phe Gly Gln Ser
            245                 250                 255

Tyr Leu Thr His Met Lys Cys Leu Glu Asn Val Gly Met Leu Gly Ile
                260                 265                 270

Lys Pro Val Met His Gln Gly Lys Glu Ile Ile Pro Ile Glu Phe Leu
            275                 280                 285

Lys Thr Leu Leu Pro Asp Pro Ala Ser Leu Gly Pro Arg Thr Lys Gly
        290                 295                 300

Tyr Thr Asn Ile Gly Cys Val Ile Arg Gly Lys Lys Asp Gly Lys Asp
305                 310                 315                 320

Lys Gln Val Tyr Ile Tyr Asn Val Cys Asn His Glu Glu Cys Tyr Lys
                325                 330                 335

Glu Thr Gly Ala Gln Ala Val Ser Tyr Thr Thr Gly Val Pro Ala Met
            340                 345                 350

Ile Gly Thr Lys Leu Ile Ala Lys Gly Ile Trp Gln Gly Lys Gly Val
        355                 360                 365

Phe Asn Met Glu Glu Phe Asp Ala Lys Pro Phe Met Glu Glu Leu Asn
370                 375                 380

Ser Gln Gly Leu Pro Trp Lys Ile Ile Glu Met Thr Pro Ser Leu Gly
385                 390                 395                 400

Glu

<210> SEQ ID NO 47
<211> LENGTH: 382
<212> TYPE: PRT
<213> ORGANISM: Campylobacter jejuni

<400> SEQUENCE: 47

Met Phe Tyr Glu Lys Ile Gln Thr Pro Ala Tyr Ile Leu Glu Glu Asp
1               5                   10                  15

Lys Leu Arg Lys Asn Cys Glu Leu Leu Ala Ser Ile Gly Glu Lys Ser
            20                  25                  30

Gly Ala Lys Val Leu Ala Leu Lys Gly Phe Ala Phe Ser Gly Ala
        35                  40                  45

Met Lys Ile Val Gly Glu Tyr Leu Lys Gly Cys Thr Cys Ser Gly Leu
    50                  55                  60

Trp Glu Ala Lys Phe Ala Lys Glu Tyr Met Asp Lys Glu Ile His Thr
65                  70                  75                  80

Tyr Ser Pro Ala Phe Lys Glu Asp Glu Ile Gly Glu Ile Ala Ser Leu
                85                  90                  95

Ser His His Ile Val Phe Asn Ser Leu Ala Gln Phe His Lys Phe Gln
                100                 105                 110

Ser Lys Thr Gln Lys Asn Ser Leu Gly Leu Arg Cys Asn Val Glu Phe
            115                 120                 125

Ser Leu Ala Pro Lys Glu Leu Tyr Asn Pro Cys Gly Arg Tyr Ser Arg
        130                 135                 140

Leu Gly Ile Arg Ala Lys Asp Phe Glu Asn Val Asp Leu Ser Thr Ile
145                 150                 155                 160

Glu Gly Leu His Phe His Ala Leu Cys Glu Glu Ser Ala Asp Ala Leu
                165                 170                 175

Glu Ala Val Leu Lys Val Phe Glu Glu Lys Phe Gly Lys Trp Ile Gly
                180                 185                 190
```

```
Gln Met Lys Trp Val Asn Phe Gly Gly Gly His His Ile Thr Lys Lys
            195                 200                 205

Gly Tyr Asp Val Glu Lys Leu Ile Ala Leu Cys Lys Asn Phe Ser Asp
    210                 215                 220

Lys Tyr Gly Val Gln Val Tyr Leu Glu Pro Gly Glu Ala Val Gly Trp
225                 230                 235                 240

Gln Thr Gly Asn Leu Val Ala Ser Val Val Asp Ile Ile Glu Asn Glu
                245                 250                 255

Lys Gln Ile Ala Ile Leu Asp Thr Ser Ser Glu Ala His Met Pro Asp
            260                 265                 270

Thr Ile Ile Met Pro Tyr Thr Ser Glu Val Leu Asn Ala Arg Ile Leu
        275                 280                 285

Ala Thr Arg Glu Asn Glu Lys Ile Ser Asp Leu Lys Glu Asn Glu Phe
    290                 295                 300

Ala Tyr Leu Leu Thr Gly Asn Thr Cys Leu Ala Gly Asp Val Met Gly
305                 310                 315                 320

Glu Tyr Ala Phe Asp Lys Lys Leu Lys Ile Gly Asp Lys Ile Ile Phe
                325                 330                 335

Leu Asp Gln Ile His Tyr Thr Ile Val Lys Asn Thr Thr Phe Asn Gly
            340                 345                 350

Ile Arg Leu Pro Asn Leu Met Leu Leu Asp His Lys Asn Glu Leu Gln
        355                 360                 365

Met Ile Arg Glu Phe Ser Tyr Lys Asp Tyr Ser Leu Arg Asn
    370                 375                 380

<210> SEQ ID NO 48
<211> LENGTH: 414
<212> TYPE: PRT
<213> ORGANISM: Vibrio cholerae

<400> SEQUENCE: 48

Met Ser Ile Leu Gln Ile Gly Ala Gly Val Gly Trp Val Val Ala
1               5                   10                  15

His Lys Ala Ala Gln Asn Asn Asp Val Leu Gly Asp Ile Thr Ile Ala
            20                  25                  30

Ser Arg Ser Ile Ala Lys Cys Glu Lys Ile Ile Glu Ser Ile Lys Gly
        35                  40                  45

Lys Asn Asn Leu Lys Asp Ser Ser Lys Leu Glu Ala Arg Gln Val
    50                  55                  60

Asn Ala Asp Asp Ile Glu Ser Leu Val Lys Leu Ile Asn Glu Val Lys
65                  70                  75                  80

Pro Asp Leu Val Ile Asn Ala Gly Pro Pro Trp Val Asn Val Ala Ile
                85                  90                  95

Met Glu Ala Cys Tyr Gln Ala Lys Val Ser Tyr Leu Asp Thr Ser Val
            100                 105                 110

Ser Val Asp Leu Cys Ser Lys Gly Gln Gln Val Pro Glu Ala Tyr Asp
        115                 120                 125

Ala Gln Trp Ala Phe Arg Asp Lys Phe Lys Gln Ala Gly Ile Thr Ala
    130                 135                 140

Ile Leu Ser Ala Gly Phe Asp Pro Gly Val Val Ser Val Phe Ala Ala
145                 150                 155                 160

Tyr Ala Ala Lys Tyr Leu Phe Asp Glu Ile Asp Thr Ile Asp Val Leu
                165                 170                 175

Asp Ile Asn Ala Gly Asp His Gly Lys Lys Phe Ala Thr Asn Phe Asp
```

```
                180             185             190
Pro Glu Thr Asn Leu Leu Glu Ile Gln Gly Asp Ser Ile Tyr Trp Asp
            195                 200             205

Ala Gly Glu Trp Lys Arg Val Pro Cys His Thr Arg Met Leu Glu Phe
    210                 215                 220

Asp Phe Pro Lys Cys Gly Lys Phe Lys Val Tyr Ser Met Ser His Asp
225                 230                 235                 240

Glu Leu Arg Ser Leu Lys Glu Phe Ile Pro Ala Lys Arg Ile Glu Phe
                245                 250                 255

Trp Met Gly Phe Gly Asp Arg Tyr Leu Asn Tyr Phe Asn Val Met Arg
            260                 265                 270

Asp Ile Gly Leu Leu Ser Pro Glu Pro Leu Thr Leu Gln Asp Gly Thr
        275                 280                 285

Val Val Lys Pro Leu Gln Val Leu Lys Ala Met Leu Pro Asp Pro Thr
    290                 295                 300

Ser Leu Ala Pro Gly Tyr Lys Gly Leu Thr Cys Ile Gly Thr Trp Val
305                 310                 315                 320

Gln Gly Lys Lys Asp Gly Lys Ala Arg Ser Val Phe Ile Tyr Asn His
                325                 330                 335

Ala Asp His Glu Val Ala Tyr His Asp Val Glu His Gln Ala Ile Ala
            340                 345                 350

Tyr Thr Thr Gly Val Pro Ala Ile Thr Ala Ala Leu Gln Phe Phe Arg
        355                 360                 365

Gly Glu Trp Ala Glu Pro Gly Val Phe Asn Met Glu Gln Leu Asn Pro
    370                 375                 380

Asp Pro Phe Leu Glu Thr Met Pro Ser Ile Gly Leu Gly Trp Asp Val
385                 390                 395                 400

Met Glu Leu Glu Pro Gly Gln Pro Asp Ile Gln Val Val Lys
                405                 410

<210> SEQ ID NO 49
<211> LENGTH: 387
<212> TYPE: PRT
<213> ORGANISM: Vibrio cholerae

<400> SEQUENCE: 49

Met Glu Thr Leu Gln Asp Ile Gly Thr Asn Met Leu Lys Asp Glu Leu
1               5                   10                  15

Arg Thr Pro Tyr Phe Met Ile Asp Glu Ala Lys Leu Ile Ala Asn Leu
            20                  25                  30

Glu Ile Ala Lys His Leu Lys Glu Ile Ser Gly Val Lys Met Val Leu
        35                  40                  45

Ala Leu Lys Cys Phe Ser Thr Trp Gly Val Phe Asp Ile Ile Lys Pro
    50                  55                  60

Tyr Leu Asp Gly Thr Thr Ser Ser Gly Pro Phe Glu Val Lys Leu Gly
65                  70                  75                  80

Tyr Glu Thr Phe Gly Gly Glu Thr His Ala Tyr Ser Val Gly Tyr Ser
                85                  90                  95

Glu Glu Asp Val Lys Glu Val Ile Asp Ile Cys Asp Lys Met Ile Phe
            100                 105                 110

Asn Ser Gln Ser Gln Leu Ala Ala Tyr Arg His Leu Val Glu Gly Lys
        115                 120                 125

Ala Ser Leu Gly Leu Arg Ile Asn Pro Gly Val Ser Tyr Ala Gly Gln
    130                 135                 140
```

```
Asp Leu Ala Asn Pro Ala Arg Gln Phe Ser Arg Leu Gly Val Gln Ala
145                 150                 155                 160

Asp His Ile Asp Glu Ser Val Phe Asp Ser Ile Asn Gly Val Met Phe
            165                 170                 175

His Met Asn Cys Glu Asn Lys Asp Val Asp Ala Phe Ile Gly Leu Leu
        180                 185                 190

Asp Ala Ile Ser Glu Arg Phe Gly Arg Tyr Leu Asp Lys Leu Asp Trp
    195                 200                 205

Val Ser Leu Gly Gly Val Phe Phe Thr Trp Pro Gly Tyr Asp Val
210                 215                 220

Glu Lys Leu Gly Ala Ala Leu Lys Ala Phe Ala Glu Arg His Ala Val
225                 230                 235                 240

Gln Leu Tyr Leu Glu Pro Gly Glu Ala Ile Ile Thr Lys Thr Thr Asp
            245                 250                 255

Leu Val Val Thr Val Val Asp Ile Val Glu Asn Gly Met Lys Thr Ala
        260                 265                 270

Ile Val Asp Ser Ala Thr Glu Ala His Arg Leu Asp Thr Leu Ile Tyr
    275                 280                 285

Lys Glu Pro Ala Ser Val Leu Glu Ala Ser Asp Lys Gly Gln His Glu
290                 295                 300

Tyr Val Ile Gly Ser Cys Ser Cys Leu Ala Gly Asp Gln Phe Cys Val
305                 310                 315                 320

Ala Lys Phe Asp Glu Pro Leu Gln Val Gly Gln Lys Leu His Ile Leu
            325                 330                 335

Asp Ser Ala Gly Tyr Thr Met Val Lys Leu Asn Trp Phe Asn Gly Leu
        340                 345                 350

Lys Met Pro Ser Val Tyr Cys Glu Arg Lys Asn Gly Gln Ile Gln Lys
    355                 360                 365

Ile Asn Gln Phe Gly Tyr Glu Asp Phe Lys Arg Thr Leu Ser Leu Trp
370                 375                 380

Ser Ile Glu
385

<210> SEQ ID NO 50
<211> LENGTH: 397
<212> TYPE: PRT
<213> ORGANISM: Bacteroides uniformis

<400> SEQUENCE: 50

Met Gly Lys Val Leu Ile Ile Gly Ala Gly Val Gly Thr Val Val
1               5                   10                  15

Ala His Lys Val Ala Gln Asn Pro Asp Val Phe Thr Glu Ile Met Ile
                20                  25                  30

Ala Ser Arg Thr Lys Ser Lys Cys Asp Ala Val Val Lys Ala Ile Gly
            35                  40                  45

Asn Pro Asn Ile Lys Thr Ala Gln Val Asp Ala Asp Ser Val Asp Glu
        50                  55                  60

Leu Val Ala Leu Phe Asn Ser Phe Lys Pro Glu Ile Val Ile Asn Val
65                  70                  75                  80

Ala Leu Pro Tyr Gln Asp Leu Thr Ile Met Glu Ala Cys Leu Gln Ser
                85                  90                  95

Gly Val Asn Tyr Leu Asp Thr Ala Asn Tyr Glu Pro Lys Asp Val Ala
            100                 105                 110

His Phe Glu Tyr Ser Trp Gln Trp Ala Tyr Lys Lys Arg Phe Glu Asp
        115                 120                 125
```

Ala Gly Leu Thr Ala Ile Leu Gly Cys Gly Phe Asp Pro Gly Val Ser
    130                 135                 140

Gly Ile Tyr Thr Ala Tyr Ala Ala Lys His His Phe Asp Glu Ile Gln
145                 150                 155                 160

Tyr Leu Asp Ile Val Asp Cys Asn Ala Gly Asn His His Lys Ala Phe
                165                 170                 175

Ala Thr Asn Phe Asn Pro Glu Ile Asn Ile Arg Glu Ile Thr Gln Asn
            180                 185                 190

Gly Arg Tyr Tyr Glu Asn Gly Glu Trp Val Thr Thr Lys Pro Leu Glu
        195                 200                 205

Ile His Lys Asp Leu Thr Tyr Pro Asn Ile Gly Pro Arg Asp Ser Tyr
    210                 215                 220

Leu Leu Tyr His Glu Glu Leu Glu Ser Leu Val Lys Asn Phe Pro Thr
225                 230                 235                 240

Ile Lys Arg Ala Arg Phe Trp Met Thr Phe Gly Gln Glu Tyr Leu Thr
                245                 250                 255

His Leu Arg Val Ile Gln Asn Ile Gly Met Ala Arg Ile Asp Glu Val
            260                 265                 270

Glu Tyr Asn Gly Met Lys Ile Val Pro Leu Gln Phe Leu Lys Ala Val
        275                 280                 285

Leu Pro Asn Pro Gln Asp Leu Gly Glu Asn Tyr Glu Gly Glu Thr Ser
    290                 295                 300

Ile Gly Cys Arg Ile Arg Gly Leu Lys Asp Gly Lys Glu Arg Thr Tyr
305                 310                 315                 320

Tyr Val Tyr Asn Asn Cys Ser His Gln Glu Ala Tyr Lys Glu Thr Gly
                325                 330                 335

Met Gln Gly Val Ser Tyr Thr Thr Gly Val Pro Ala Met Ile Gly Ala
            340                 345                 350

Met Met Phe Leu Lys Gly Leu Trp Lys Lys Pro Gly Val Trp Asn Val
        355                 360                 365

Glu Glu Phe Asn Pro Asp Pro Phe Met Glu Gln Leu Asn Lys Gln Gly
    370                 375                 380

Leu Pro Trp His Glu Ile Ile Asp Gly Asp Leu Glu Val
385                 390                 395

<210> SEQ ID NO 51
<211> LENGTH: 366
<212> TYPE: PRT
<213> ORGANISM: Bacteroides uniformis

<400> SEQUENCE: 51

Met Glu Glu Gly Leu Leu Arg Lys Asn Leu Ala Leu Ile Lys Ser Val
1               5                   10                  15

Ala Asp Arg Ala Gly Val Glu Ile Ile Leu Ala Phe Lys Ser Phe Ala
            20                  25                  30

Met Trp Arg Ser Phe Pro Ile Phe Arg Glu Tyr Ile Asp His Ser Thr
        35                  40                  45

Ala Ser Ser Val Tyr Glu Ala Arg Leu Ala Leu Glu Glu Phe Gly Ser
    50                  55                  60

Lys Ala His Thr Tyr Ser Pro Ala Tyr Thr Glu Ala Asp Phe Pro Glu
65                  70                  75                  80

Ile Met Arg Cys Ser Ser His Ile Thr Phe Asn Ser Leu Ser Gln Phe
                85                  90                  95

His Arg Phe Tyr Pro Val Val Val Ala Glu Gly Ser Gly Ile Ser Cys

```
                100               105              110
Gly Ile Arg Ile Asn Pro Glu Tyr Ser Glu Val Glu Thr Glu Leu Tyr
            115              120             125

Asn Pro Cys Ala Pro Gly Thr Arg Phe Gly Val Met Ala Asp Pro Leu
            130              135             140

Pro Glu Glu Leu Pro Val Gly Ile Glu Gly Phe His Cys His Cys His
145             150              155             160

Cys Glu Ser Ser Ser Tyr Glu Leu Glu His Thr Leu Glu His Leu Glu
                165              170             175

Gly Lys Phe Ser Arg Trp Phe Ser Gln Ile Lys Trp Leu Asn Leu Gly
            180              185             190

Gly Gly His Leu Met Thr Arg Lys Asp Tyr Asp Val Glu His Leu Val
            195              200             205

Arg Leu Leu Gln Gly Leu Lys Gly Arg Tyr Ser His Leu Gln Ile Ile
            210              215             220

Leu Glu Pro Gly Ser Ala Phe Thr Trp Gln Thr Gly Val Leu Ser Ser
225             230              235             240

Glu Ile Val Asp Ile Val Glu Asn Arg Gly Ile Arg Thr Ala Ile Leu
                245              250             255

Asn Val Ser Phe Thr Cys His Met Pro Asp Cys Leu Glu Met Pro Tyr
            260              265             270

Gln Pro Ala Val Arg Gly Ala Glu Met Gly Asp Ala Gly Pro Tyr Val
            275              280             285

Tyr Arg Leu Gly Gly Asn Ser Cys Leu Ser Gly Asp Tyr Met Gly Leu
            290              295             300

Trp Ser Phe Asp His Glu Leu Gln Ile Gly Glu Arg Ile Val Phe Glu
305             310              315             320

Asp Met Ile His Tyr Thr Thr Val Lys Thr Asn Met Phe Asn Gly Ile
                325              330             335

His His Pro Ala Ile Ala Met Trp Thr Lys Glu Gly Lys Ala Glu Val
            340              345             350

Phe Lys Gln Phe Ser Tyr Glu Asp Tyr Arg Gly Arg Met Ser
            355              360             365
```

L-ORNITHINE PRODUCTION IN EUKARYOTIC CELLS

STATEMENT OF PRIORITY

This application is a 35 U.S.C. § 371 national phase application of International Application Serial No. PCT/SE2016/050193, filed Mar. 10, 2016, which claims the benefit, under 35 U.S.C. § 119 (a) of U.S. Provisional Patent Application No. 62/166,050, filed May 25, 2015, and U.S. Provisional Patent Application No. 62/132,349, filed Mar. 12, 2015, the entire contents of each of which are incorporated by reference herein.

TECHNICAL FIELD OF THE INVENTION

The present invention relates to the development of genetically engineered microorganisms that can produce L-ornithine and its derivatives. More specifically the invention relates to the production of L-ornithine, which can, for instance, be used as food additive using genetically engineered eukaryotic cells. Such L-ornithine producing eukaryotic cells, for instance yeast cells, can also be directly used for baking, brewing, or making other food products. In addition, other new chemicals using L-ornithine as precursors in the cell can also be produced when said L-ornithine producing eukaryotic cells are subject to further genetic modifications. These chemicals include but not limited to L-arginine, L-citrulline, putrescine, spermidine, spermine, agmatine and tropane alkaloids, etc.

BACKGROUND OF THE INVENTION

L-ornithine, the intermediate of L-arginine biosynthesis, has already been widely used as a dietary supplement, as it is known to be beneficial for the treatment of wound healing and liver disease. Furthermore, it is also the precursor of bulk chemicals such as putrescine, an important diamine used as a nylon monomer, and natural products such as tropane alkaloids, which are used as parasympatholytics for competitively antagonizing acetylcholine.

L-ornithine is nowadays prepared by various processes, encompassing chemical synthesis and enzymatic catalysis. For instance, EP0464325A2 discloses an enzymic conversion process for the preparation of salts of L-ornithine from L-arginine in the presence of the enzyme L-arginase (EC 3.5.3.1.) extracted from animal liver. To reduce the cost of the enzyme, a whole-cell biotransformation system for the conversion of L-arginine to L-ornithine was also developed by constructing a recombinant *Escherichia coli* with over-expressed arginase (EC 3.5.3.1) encoding gene ARG from the bovine liver (Zhan et al. 2013). However, said whole-cell biotransformation system always has the problem of cell permeability, and addition of permeability reagent may lead to subsequent product separation problems. One idea has been to screen for a thermophilic enzyme, higher operation temperature could be used to improve the permeability of the recombinant cells. Arginase (ARG) from *Bacillus caldovelox* was found to be a potential thermophilic candidate (Patchett et al. 1991). Recently, the recombinant *E. coli* with *B. caldovelox* ARG gene was constructed, leading to an efficient and simple enzymatic process for the environment-friendly synthesis of L-ornithine from L-arginine (Song et al. 2014).

However, these methods either suffer from issues of expensive substrates, poor enantiopure purity or are environmental unfriendly.

Some L-citrulline or L-arginine auxotroph bacteria belong to the genus *Brevibacterium*, the genus *Corynebacterium*, the genus *Bacillus* and the genus *Arthrobacter* are known to produce L-ornithine. In addition, variants of said L-ornithine producing bacteria having resistance to arginine analogues and/or 2-thiazolealanine and/or sulfaguanidine and/or 2-fluoropyruvic acid and/or microphenolic acid and/or ornithinol are said to have better L-ornithine producing performance. Metabolic engineering frameworks, which offer the ability to leverage the advantages of biocatalysts (e.g. precision, specificity) and tailor the carbon flow of microbes, have enabled construction of platform cell factories for producing amino acids. Recent advantages in the said metabolic engineering also lead to the strain construction for L-ornithine production (Hwang and Cho 2012; Hwang and Cho 2014; Hwang et al. 2008; Jiang et al. 2013a; Jiang et al. 2013b). For instance, WO 2012008809 A2 discloses a strategy to give the L-ornithine production at a high yield rate and with high efficiency by the fine-turning of gluconate kinase (GntK) in *Corynebacterium*. In another disclose, U.S. Pat. No. 8,741,608 B2 suggests that overexpressing of L-ornithine exporter is an efficient strategy to further improve L-ornithine titers. US 20140051132 A1 also discloses an invention where NCgl_2067-NCgl_2065 operon in *Corynebacterium* is/are attenuated lead to the improved production of L-amino acids belonging to L-glutamate family which includes L-ornithine. NCgl_2067-NCgl_2065 operon was suggested to encode negative regulators which directly controls expression of the related genes in the L-amino acids synthesis belong to L-glutamate.

However, one of the main drawbacks of L-ornithine production in bacterial strains is the phage contamination issues which often result in substantial economic losses. Thus, there is a need for better microbial strategies for the production of L-ornithine, putrescine, spermidine, spermine and other chemicals using these compounds as a precursor

SUMMARY OF THE INVENTION

Thus it is an object of the present disclose to provide an improved eukaryotic cell factory, such yeast cell factory that can be used for fermentation based production of L-ornithine. The L-ornithine synthesis pathway, and even the central metabolism in the said cell factory are harnessed to manage the said challenges.

An aspect of the embodiments relates to a eukaryotic cell capable of producing L-ornithine. The eukaryotic cell is genetically modified for attenuated activity of an ornithine carbamyoltransferase.

Another aspect of the embodiments relates to a eukaryotic cell capable of producing L-ornithine. The eukaryotic cell is genetically modified for enhanced L-ornithine biosynthesis from α-ketoglutarate.

A further aspect of the embodiments relates to a eukaryotic cell capable of producing L-ornithine. The eukaryotic cell is genetically modified for enhanced α-ketoglutarate biosynthesis.

Yet another aspect of the embodiments relates to a process for production of L-ornithine. The process comprising cultivating a eukaryotic cell according to the embodiments in the presence of a carbon source.

The eukaryotic cells of the embodiments can be further genetically modified for the production of polyamines. A further aspect of the embodiments relates to a process for production of a polyamine selected from the group consisting of putrescine, spermidine and spermine. The process comprising cultivating a eukaryotic cell according to the embodiments in the presence of a carbon source.

The successful proof of concept production of L-ornithine with S. cerevisiae in the present disclose represents the first systematics case implementation to produce amino acids in eukaryotic microbes, which demonstrated the potential to use eukaryotic microbes as the cell factory to produce amino acid or even other amino acid derived chemicals.

According to the present invention microbes can be further engineered to produce L-ornithine-derived products, such as the polyamines putrescine, spermidine and spermine, as well as the arginine-derivative agmatine, which have a variety of industrial applications. This includes overexpression of native and heterologous steps in the biosynthesis of these compounds, as well as elimination of competitive steps. Furthermore, the cellular transport systems are manipulated to allow export of these compounds into the media. We also present several gene targets that can be manipulated in order to allow high tolerance to these compounds when synthesized at large quantities.

DETAILED DESCRIPTION

Figure 1A:
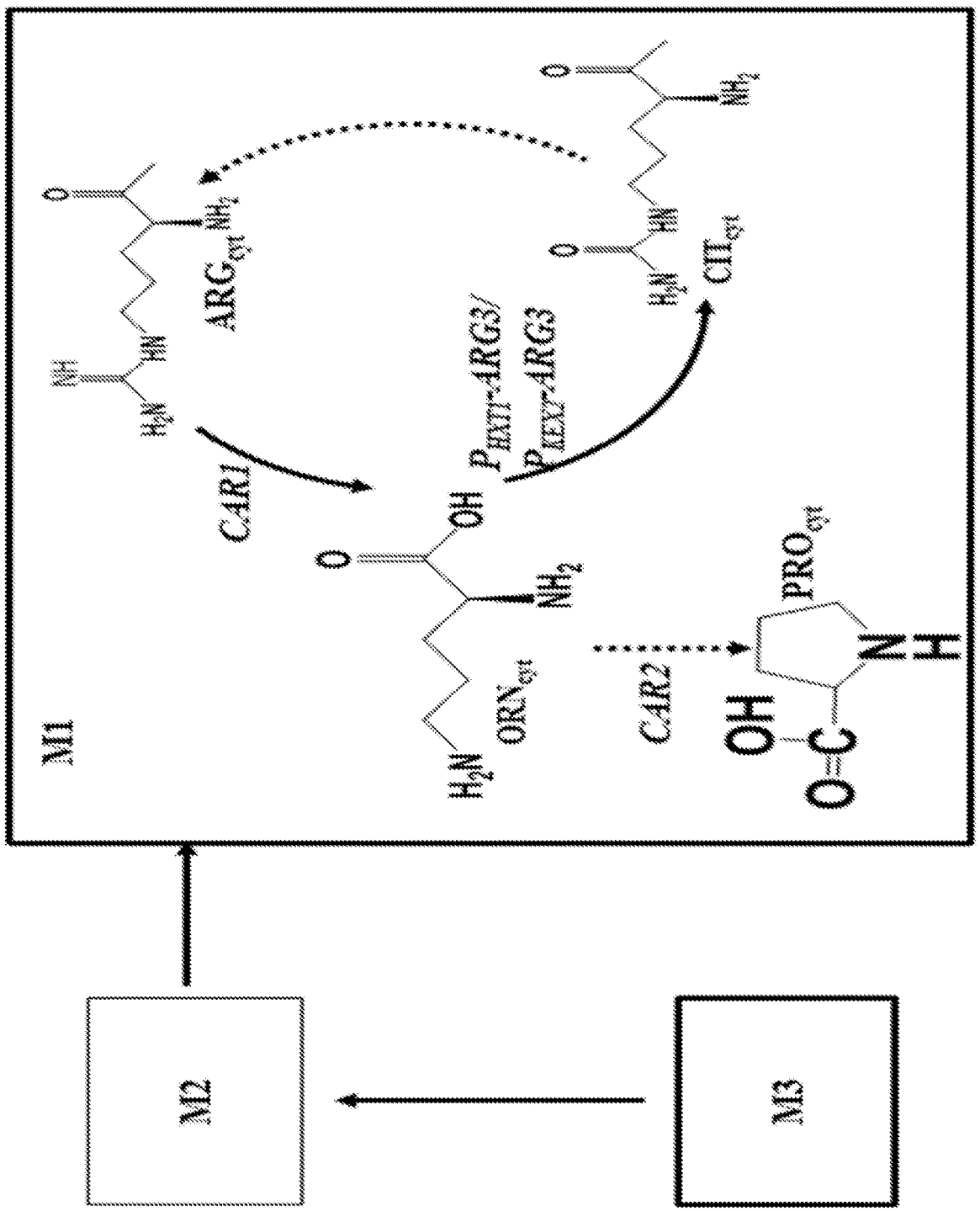
FIG. 1. L-arginine leaky auxotroph enables L-ornithine overproduction. (a) The attenuation of ARG3 was implemented by replacing the original promoter of ARG3 with the HXT1 or KEX2 promoter ($P_{HXT1}$-ARG3 and $P_{KEX2}$-ARG3, respectively). Dashed arrows represent multiple reaction steps. (b) The transcriptional attenuation of Arg3p and knockout of L-ornithine potential consumption step (Car2p) led L-ornithine overproduction. Black filled circle indicates the molecular implementation is included in the strain under test. (c) The transcriptional attenuation of Arg3p decreased the intracellular L-arginine pool. All the strains were cultivated for 72 h in Delft medium. All data are presented as the mean±s.d. (n≥3).

Several unique features of Baker's yeast *S. cerevisiae*, including its robustness, GRAS (generally recognized as safe) status, excellent availability of molecular biology tools, wide use in industry, including large scale bioethanol production, and the more efficient ability to express complex enzymes such as cytochrome P450-containing enzymes, make it an attractive chasis host for production various chemicals. Furthermore, as *S. cerevisiae* is also widely used in brewing and baking industries, the L-ornithine producing yeast could represent a plug and play solution for the production of L-ornithine containing drinks and/or baking products or even other functional food products.

L-arginine biosynthesis is known for its compartmentalization in metabolism where L-ornithine, the precursor of L-arginine is synthesized in the mitochondria using L-glutamate as substrate which is produced in the cytoplasm. After transport to the cytoplasm, L-ornithine is converted to L-arginine after three consecutive steps. In addition, α-ketoglutarate, the precursor of L-glutamate is one of the intermediates of TCA cycle, the flux of which is limited by the so called 'Crabtree effect' leading to the formation of ethanol as main byproduct. It is obvious that engineering *S. cerevisiae* to accumulate amino acids including L-ornithine remains a daunting task.

According to the above mentioned characteristics of L-ornithine metabolism, there are at least four challenges in constructing an L-ornithine over-producing yeast strain: (i) how to tune more metabolic flux stop at L-ornithine rather than toward L-arginine biosynthesis without incapacitating the ability of L-arginine synthesis, as sufficient L-arginine is necessary for cell growth; (ii) how to balance and coordinate the corresponding pathways and enzymes in different sub- cellular organelles, as pathway perturbation could create a substantial bottleneck due to membranes transportation of intermediates and these intermediates will be redirect to competing pathways; (iii) how to increase the supply of the precursor α-ketoglutarate, as 'Crabtree effect' will limit the TCA cycle efficiency for α-ketoglutarate biosynthesis during normal batch fermentation with sufficient glucose; (iv) the total pathway optimization calls for intensive perturbations to the related pathways. How to implement the desired engineering strategies efficiently is yet to be demonstrated.

The invention herein relies, unless otherwise indicated, on the use of conventional techniques of metabolic engineering, fermentation engineering, synthetic biology, biochemistry, molecular biology, cell biology, microbiology and recombinant DNA technology.

To facilitate understanding of the invention, a number of terms are defined below.

As used herein, the term "modified" refers to a host organism that has been modified to increase production of L-ornithine, putrescine, spermidine, spermine or agmatine, as compared with an otherwise identical host organism that has not been so modified. In principle, such "modification" in accordance with the present disclosure may comprise any physiological, genetic, chemical, or other modification that appropriately alters production of these compounds production in a host organism as compared with such production in an otherwise identical organism which is not subject to the said modification. In most of the embodiments, however, the modification will comprise a genetic modification. In certain embodiments, as described herein, the modification comprises introducing into a host cell, and particularly into a host cell which is reduced or negative for ornithine carbamoyltransferase activity. In some embodiments, a modification comprises at least one physiological, chemical, genetic, or other modification; in other embodiments, a modification comprises more than one chemical, genetic, physiological, or other modification. In certain aspects where more than one modification is made use of, such modifications can include any combinations of physiological, genetic, chemical, or other modification (e.g., one or more genetic, chemical and/or physiological modification(s)). Genetic modifications which boost the activity of a polypeptide include, but are not limited to: introducing one or more copies of a gene encoding the polypeptide (which may distinguish from any gene already present in the host cell encoding a polypeptide having the same activity); altering a gene present in the cell to increase transcription or translation of the gene (e.g., altering, adding additional sequence to, replacement of one or more nucleotides, deleting sequence from, or swapping for example, regulatory, a promoter or other sequence); and altering the sequence (e.g. non-coding or coding) of a gene encoding the polypeptide to boost activity (e.g., by increasing enzyme activity, decrease feedback inhibition, targeting a specific subcellular location, boost mRNA stability, boost protein stability). Genetic modifications that reduce activity of a polypeptide include, but are not limited to: deleting a portion or all of a gene encoding the polypeptide; inserting a nucleic acid sequence which disrupts a gene encoding the polypeptide; changing a gene present in the cell to reduce transcription or translation of the gene or stability of the mRNA or polypeptide encoded by the gene (for example, by adding additional sequence to, altering, deleting sequence from, replacement of one or more nucleotides, or swapping for example, replacement of one or more nucleotides, a promoter, regulatory or other sequence).

As used herein, the term "open reading frame (ORF)" refers to a region of RNA or DNA encoding polypeptide, a peptide, or protein.

As used herein, the term "recombinant" means that a particular nucleic acid (RNA or DNA) is the product of various combinations of restriction, cloning, and/or ligation steps resulting in constructs with structural non-coding or -coding sequences different from endogenous nucleic acids found in the systems of natural.

As used herein, "recombinant eukaryotic cells" according to the present disclose is defined as cells which contain additional copies or copy of an endogenous nucleic acid sequence or are transformed or genetically modified with polypeptide or a nucleotide sequence that does not naturally occur in the eukaryotic cells. The wild-type eukaryotic cells are defined as the parental cells of the recombinant eukaryotic cells, as used herein.

As used herein, "recombinant prokaryotic cells" according to the present disclose is defined as cells which contain additional copies or copy of an endogenous nucleic acid sequence or are transformed or genetically modified with polypeptide or a nucleotide sequence that does not naturally occur in the prokaryotic cells. The wild-type prokaryotic cells are defined as the parental cells of the recombinant prokaryotic cells, as used herein.

As used herein, the term "endogenous" when used with respect to a nucleic acid (RNA or DNA) or protein refers to a protein or a nucleic acid which occurs naturally as part of the cell, organism, genome or RNA or DNA sequence where it is present.

As used herein, the term "heterologous" when used with respect to a nucleic acid (RNA or DNA) or protein refers to a protein or a nucleic acid which occurs non-naturally as part of the cell, organism, genome or RNA or DNA sequence where it is present. Heterologous proteins or nucleic acids are not endogenous to the cell where it is introduced, but have been obtained from synthetically produced or one of another cells.

As used herein, the term "gene" indicates to a nucleic acid sequence which contains a template for a nucleic acid polymerase (in eukaryotes, RNA polymerase II). Genes are transcribed into mRNAs which are then translated into proteins.

As used herein, the term "genome" encompasses both the plasmids and chromosomes in a host cell. For instance, encoding nucleic acids of the present disclosure which are introduced into host cells can be portion of the genome whether they are chromosomally integrated or plasmids-localized, i.e. present in plasmids.

As used herein, the term "nucleic acid" refers to a ribonucleotide polymer or unless otherwise indicated, the term includes reference to the complementary sequence and the specified sequence thereof.

As used herein, the terms "peptide", "polypeptide", and "protein" are used interchangeably to indicate to a polymer of amino acid residues. The terms "peptide", "polypeptide" and "protein" also includes modifications including, but not limited to, lipid attachment, glycosylation, glycosylation, sulfation, hydroxylation, γ-carboxylation of L-glutamic acid residues and ADP-ribosylation.

As used herein, the term "enzyme" is defined as a protein which catalyses a chemical or a biochemical reaction in a cell. Usually, according to the present invention, the nucleotide sequence encoding an enzyme is operably linked to a nucleotide sequence (promoter) that causes sufficient expression of the corresponding gene in the eukaryotic cell to confer to the cell the ability to produce L-ornithine.

As used herein, the term "promoter" refers to a nucleic acid sequence which has functions to control the transcription of one or more genes, which is located upstream with respect to the direction of transcription of the transcription initiation site of the gene. Suitable promoters in this context include both constitutive and inducible natural promoters as well as engineered promoters, which are well known to the person skilled in the art. Suitable promoters in eukaryotic host cells may be PDC, GPD1, TEF1, PGK1 and TDH. Other suitable promoters include HIS3, CYC1, ADH1, PGL, GAPDH, ADC1, URA3, TRP1, LEU2, TPI, AOX1 and ENO1.

As used herein, the term "terminator" is functional in the eukaryotic cell used in the present invention. Natural genes of the host cell are the preferred terminators source.

As used herein, the term "overexpression" refers to increasing the number of copies of a desired nucleic acid sequence. Normally, overexpression leads to an increased level of activity of an enzyme and/or proteins, and/or to an increased level of activity in a desirable location (e.g., in the cytosol or mitochondria). There are a lot of strategies available in the art for overexpression of special nucleotide sequences encoding enzymes and/or proteins in a eukaryotic cell. Particularly, a nucleotide sequence encoding an enzyme/protein may be overexpressed by increasing the copy number of the gene coding for the enzyme/protein in the cell, e.g. by integrating additional copies of the gene in the cell's genome, from an episomal multicopy expression vector, by expressing the gene from a centromeric vector, or by introducing an (episomal) expression vector that comprises multiple copies of the gene. Preferably, overexpression of the enzyme/protein according to the disclosure is obtained with a constitutive strong promoter.

The term "overproducing" is used herein in reference to the production of L-ornithine in a host cell and indicates that the host cell is producing more of L-ornithine, putrescine, spermidine, spermine or other compounds as disclosed herein by virtue of the introduction of nucleic acid sequences which encode different polypeptides involved in the host cell's metabolic pathways or as a result of other modifications as compared with the unmodified host cell or wild-type cell.

As used herein, the term "Crabtree effect" refers to the phenomenon whereby the yeast, *S. cerevisiae*, produces ethanol in high external glucose concentrations and aerobic conditions rather than producing biomass via the tricarboxylic acid (TCA) cycle, which is the common process occurring aerobically in most yeasts e.g. *Kluyveromyces* spp.

As used herein the term "vector" is defined as a linear or circular DNA molecule comprising a polynucleotide encoding a polypeptide of the invention, and which is operably linked to additional nucleotides that ensure its expression.

As used herein, sequence identity refers to sequence similarity between two nucleotide sequences or two peptide or protein sequences. The similarity is determined by sequence alignment to determine the structural and/or functional relationships between the sequences.

In certain embodiments, the present disclosure relates to a modified eukaryotic cell, preferably, the eukaryotic cell is yeast cell, wherein the yeast cell can overproduce L-ornithine. Said overproduction of L-ornithine is obtained in the first place by the down-regulation or attenuation of specially selected genes, wherein said genes encode enzymes involved in the L-ornithine and/or polyamine consumption and/or degradation pathways. Further L-ornithine production ability is improved by down-regulation, attenuation, deletion or overexpression of specially selected genes, wherein said genes encode enzymes and/or proteins involved in the L-ornithine 'acetylated derivatives cycle', L-glutamate synthesis pathways, subcellular trafficking, TCA cycle, pyruvate carboxylation pathway, respiratory electron-transport chain, and the carbon subtracts assimilation machinery.

Preferably, the yeast to be modified can be selected from any known genus and species of yeast. In one embodiment, the yeast genus can be *Saccharomyces, Kluyveromyces, Zygosaccharomyces, Candida, Hansenula, Torulopsis, Kloeckera, Pichia, Schizosaccharomyces, Trigonopsis, Brettanomyces, Debaromyces, Nadsonia, Lipomyces, Cryptococcus, Aureobasidium, Trichosporon, Lipomyces, Rhodotorula, Yarrowia, Phaffia,* or *Schwanniomyces,* among others. In a further embodiment, the yeast can be *Saccharomyces, Yarrowia, Zygosaccharomyces, Kluyveromyces* or *Pichia* spp. In yet a further embodiment, the yeast can be *Saccharomyces cerevisiae, Saccharomyces boulardii, Zygosaccharomyces bailii, Kluyveromyces lactis,* and *Yarrowia lipolytica. Saccharomyces cerevisiae* is commonly used yeast in industrial processes, but the disclosure is not limited thereto. Other yeast species useful in the present disclosure include but are not limited to *Schizosaccharomyces pombe, Hansenula anomala, Candida sphaerica,* and *Schizosaccharomyces malidevorans.*

In one embodiment the prokaryotic cell can be a bacterial cell or archaeal cell. The recombinant bacterial cell could be gram positive or gram negative bacteria. The bacteria may also be photosynthetic bacteria (e.g. cyanobacteria). The bacteria can either be Gram-negative or Gram-positive. The genera of Gram negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium.* The genera of Gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

In some embodiments, the present disclose relates to a modified yeast cell, wherein the activity of the L-ornithine consumption and/or degradation pathway of the yeast cell was reduced. In one preferred embodiment, the yeast cell is *S. cerevisiae.* In one preferred embodiment, the activity of ornithine carbamoyltransferase in *S. cerevisiae* is reduced. In one preferred embodiment, the activity of ornithine carbamoyltransferase in *S. cerevisiae* is reduced by down-regulation, attenuation or deletion the ornithine carbamoyltransferase encoding gene, wherein the said gene is ARG3. The attenuation of objective gene can be achieved by known methods in the art. In one preferred embodiment, the attenuation of ARG3 is achieved by replaced the promoter region of ARG3 with weak constitutive promoter, for instance the promoter of KEX2. It was found that the attenuation of the ARG3 by the promoter replacement strategy led to the production of L-ornithine which would not achieve with the wild-type strain which has native ARG3 promoter.

In one preferred embodiment, the reduced L-ornithine degradation activity is achieved by reducing the activity of L-ornithine transaminase (OTAse) which catalyzes the second step of arginine degradation in eukayotic cell. In one preferred embodiment, the reduced L-ornithine degradation activity is achieved by reducing the activity of L-ornithine transaminase (OTAse) which catalyzes the second step of arginine degradation in *S. cerevisiae.* In one preferred embodiment, the reduction of OTAse activity is achieved by deleting the OTAse encoding gene CAR2 in *S. cerevisiae.* The gene deletion can be achieved by known methods in the art. The CAR2 deletion improves the L-ornithine production.

In a preferred embodiment, the activity of arginase which catabolizes L-arginine to L-ornithine and urea is increased in the eukaryotic cell. In a preferred embodiment, the activity of arginase which catabolizes L-arginine to L-ornithine and urea is increased in the modified *S. cerevisiae.* The increasing activity of arginase could be achieved by known methods in the art. For instance, the increasing activity of arginase could be achieved by overexpressing the encoding gene of arginase. The arginase encoding gene can be from any known species, for instance *S. cerevisiae.* In one preferred embodiment, the overexpressing of the CAR1 gene which encodes the arginase is achieved in the modified *S. cerevisiae.* Surprisingly, the overexpression of CAR1 gene in the modified yeast cell led to increased production of L-ornithine. Preferably, the yeast cell overexpresses a nucleotide sequence encoding arginase comprising an amino acid sequence that has at least 40%, preferably at least 45, 50, 55, 60, 65, 70, 75, 80, 85, 90, 95, 97, 98, 99% sequence identity with the amino sequence of SEQ ID NO: 1. Preferably, the nucleotide sequence encodes arginase comprising the amino acid sequence of SEQ ID NO: 1.

In one preferred embodiment, the carbon channeling from α-ketoglutarate to L-ornithine is enhanced in the modified eukaryotic cell. In one preferred embodiment, the carbon channeling from α-ketoglutarate to L-ornithine is enhanced in the modified yeast cell. In a preferred embodiment, the carbon channeling from α-ketoglutarate to L-ornithine is enhanced in the modified *S. cerevisiae.* Direct enhancing precursor supply pathway was a very commonplace strategy in bacteria to boost more flux to the desired products, yet, the segmentation of precursor intermediates in different subcellular organelles compromised the metabolic engineering endeavors in *S. cerevisiae.* L-ornithine biosynthetic pathway is one of such complicated pathways which is subject to subcellular compartmentalization: the downstream L-ornithine 'acetylated derivatives cycle' and the TCA cycle which gives the precursors of L-glutamate are confined to the mitochondria, while the middle of L-glutamate supply pathway is confined to cytoplasm. According to the metabolism architecture, three strategies were proposed to improve the pathway efficiency between α-ketoglutarate node of TCA cycle and L-ornithine 'acetylated derivatives cycle' as follows: (i) directly enhance the endogenous pathway in its quondam subcellular organelle and the subcellular trafficking step; (ii) re-localize the L-glutamate synthesis reaction into mitochondria to avoid the subcellular trafficking of L-glutamate and its precursor α-ketoglutarate and (iii) 'short-circuit' the total L-ornithine pathway started from TCA cycle to cytosol to bypass the subcellular trafficking of L-glutamate and L-ornithine.

In one preferred embodiment, the carbon channeling from α-ketoglutarate to L-ornithine is enhanced in the modified eukaryotic cell by directly enhancing the endogenous pathway in its quondam subcellular organelle and the subcellular trafficking steps. In one preferred embodiment, the carbon channeling from α-ketoglutarate to L-ornithine is enhanced in the modified *S. cerevisiae* by directly enhancing the endogenous pathway in its quondam subcellular organelle and the subcellular trafficking steps. In one preferred embodiment, enhancing the endogenous pathway in its quondam subcellular organelle and the subcellular trafficking steps is achieved by overexpressing of any enzymes/proteins or any combinations of said enzymes/proteins in the pathway from α-ketoglutarate to L-ornithine in the eukaryotic cell. In one preferred embodiment, enhancing the endogenous pathway in its quondam subcellular organelle and the subcellular trafficking steps is achieved by increasing the activity of any enzymes/proteins or any combinations of said enzymes/proteins in the pathway from α-ketoglutarate to L-ornithine in S. cerevisiae. These enzymes/proteins comprise: acetylglutamate synthase (glutamate N-acetyltransferase), acetylglutamate kinase and N-acetyl-gamma-glutamyl-phosphate reductase, mitochondrial ornithine acetyltransferase, acetylornithine aminotransferase, $NADP^+$-dependent glutamate dehydrogenase, glutamine synthetase (GS), $NAD^+$-dependent glutamate synthase (GOGAT), ornithine transporter of the mitochondrial inner membrane, glutamate uniporter, mitochondrial inner membrane α-ketoglutarate transporter. In one preferred embodiment, the increased activity of any of the said enzymes/proteins or any combinations of thereof is achieved by overexpression the encoding genes. Preferably, at least one endogenous or homologous pyruvate carboxylase is/are overexpressed in the eukaryotic cell according to the invention. In one preferred embodiment, the increased activity of any of the said enzymes is achieved by overexpressing the related genes in cytosol or mitochondria. Any genes either endogenous or heterogonous to the modified eukaryotic cell could be chosen as the overexpressing targets. In one preferred embodiment, the overexpression of any genes or any combinations of genes in the list comprising ARG2 (SEQ ID NO: 2), ARG5, 6 (SEQ ID NO: 3), ARG8 (SEQ ID NO: 4), ARG7 (SEQ ID NO: 5), GDH1 (SEQ ID NO: 6), GDH3 (SEQ ID NO: 7), GLN1 (SEQ ID NO: 8), GLT1 (SEQ ID NO: 9), ORT1 (SEQ ID NO: 10), AGC1 (SEQ ID NO: 11) and ODC1 (SEQ ID NO: 12) which are all from S. cerevisiae is achieved.

In one preferred embodiment, L-ornithine 'acetylated derivatives cycle' is re-localized to cytosol in the modified eukaryotic cell. In one preferred embodiment, L-ornithine 'acetylated derivatives cycle' is re-localized to cytosol in the modified S. cerevisiae. In one preferred embodiment, L-ornithine 'acetylated derivatives cycle' is re-localized to cytosol in the modified S. cerevisiae by increasing the enzyme activity of the related enzymes in the said pathway from bacteria cell. In one preferred embodiment, L-ornithine 'acetylated derivatives cycle' is re-localized to cytosol in the modified S. cerevisiae by overexpression all the genes in the said pathway from bacteria cell. In one preferred embodiment, L-ornithine 'acetylated derivatives cycle' is re-localized to cytosol in the modified S. cerevisiae by overexpression all the genes in the said pathway from bacteria cell, wherein the genes comprising E. coli $argA_{Ec}$ (SEQ ID NO: 23) and $argB_{Ec}$(SEQ ID NO: 24), and C. glutamicum $argC_{Cg}$ (SEQ ID NO: 25), $argD_{Cg}$(SEQ ID NO: 26) and $argJ_{Cg}$(SEQ ID NO: 27).

In certain preferred embodiment, the efficiency of carbon channeling from substrate to α-ketoglutarate is enhanced in the modified eukaryotic cell. In certain preferred embodiment, the efficiency of carbon channeling from substrate to α-ketoglutarate is enhanced in the modified yeast cell. In certain preferred embodiment, the efficiency of carbon channeling from substrate to α-ketoglutarate is enhanced in the modified eukaryotic cell. In certain preferred embodiment, the efficiency of carbon channeling from substrate to α-ketoglutarate is enhanced in the modified S. cerevisiae.

In one preferred embodiment, the efficiency of carbon channeling from substrate to α-ketoglutarate is enhanced by increase in the enzymes/proteins activity of at least one enzyme/protein in the pathway from carbon substrate to the α-ketoglutarate in the modified eukaryotic cell. In one preferred embodiment, the efficiency of carbon channeling from substrate to α-ketoglutarate is enhanced by increase in the enzymes/proteins activity of at least one enzyme/protein in the pathway from carbon substrate to the α-ketoglutarate in the modified yeast cell. In one preferred embodiment, the efficiency of carbon channeling from substrate to α-ketoglutarate is enhanced by increase in the enzymes/proteins activity of at least one enzyme/protein in the pathway from carbon substrate to the α-ketoglutarate in the modified S. cerevisiae cell. In one preferred embodiment, the efficiency of carbon channeling from substrate to α-ketoglutarate is enhanced by increasing the enzyme/protein activity of at least one enzyme/protein in the pathway from carbon substrate to the α-ketoglutarate in the modified S. cerevisiae cell, wherein the increasing of the activity of enzymes/proteins is achieved by overexpressing the encoding genes of said enzymes/proteins. Preferably, the eukaryotic cell according to the present disclose, overexpress a nucleotide sequence encoding a pyruvate carboxylase (PYC), preferably a pyruvate carboxylase that is active either at cytosol or mitochondria upon expression of a nucleotide sequence encoding a PYC, for instance a PYC comprising an amino acid sequence according to SEQ ID NO: 13. Preferably, an endogenous or homologous pyruvate carboxylase is overexpressed in the eukaryotic cell according to the invention. It was found that overexpressing an endogenous pyruvate carboxylase (PYC) resulted in increased L-ornithine production levels by the eukaryotic cell according to the present disclosure.

Preferably, the eukaryotic cell according to the present disclose, overexpress a nucleotide sequence encoding a citrate synthase (CS) which catalyzes the condensation of acetyl coenzyme A and oxaloacetate to form citrate, preferably a citrate synthase that is active either at cytosol or mitochondria upon expression of a nucleotide sequence encoding a CS, for instance a CS comprising an amino acid sequence according to SEQ ID NO: 14. Preferably, an endogenous or homologous pyruvate carboxylase is overexpressed in the eukaryotic cell according to the invention. Surprisingly, it was found that overexpressing an endogenous citrate synthase (CS) resulted in increased L-ornithine production levels by the eukaryotic cell according to the present disclosure.

Preferably, the eukaryotic cell according to the present disclose, the activity of pyruvate dehydrogenase (PDH) is increased. Preferably, the increase activity of PDH is achieved by overexpressing at least one subunit of PDH. Preferably, the nucleotide sequence encoding E1 alpha subunit of the pyruvate dehydrogenase (PDH) complex, preferably E1 alpha subunit of the pyruvate dehydrogenase (PDH) that is active either at cytosol or mitochondria is upon expression of a nucleotide sequence encoding said protein, for instance a E1 alpha subunit of the pyruvate dehydrogenase (PDH) comprising an amino acid sequence according to SEQ ID NO: 15. Preferably, an endogenous or homologous pyruvate carboxylase is overexpressed in the eukaryotic cell according to the invention. Surprisingly, it was found that overexpressing an endogenous pyruvate dehydrogenase (PDH) subunit resulted in increased L-ornithine production levels by the eukaryotic cell according to the present disclosure.

Preferably, the eukaryotic cell according to the present disclose, overexpresses a nucleotide sequence encoding a aconitase, preferably an aconitase is active either at cytosol or mitochondria upon expression of a nucleotide sequence encoding a aconitase, for instance an aconitase comprising an amino acid sequence according to SEQ ID NO: 16. Preferably, an endogenous or homologous aconitase is overexpressed in the eukaryotic cell according to the invention. Surprisingly, it was found that overexpressing an aconitase resulted in increased L-ornithine production levels by the eukaryotic cell according to the present disclosure.

Preferably, the eukaryotic cell according to the present disclose, overexpresses a nucleotide sequence encoding an isocitrate dehydrogenase (IDP) which catalyzes the oxidation of isocitrate to α-ketoglutarate, preferably an IDP is active either at cytosol or mitochondria upon expression of a nucleotide sequence encoding an IDP, for instance an IDP comprising an amino acid sequence according to SEQ ID NO: 17. Preferably, an endogenous or homologous IDP is overexpressed in the eukaryotic cell according to the invention. It was found that overexpressing an IDP resulted in increased L-ornithine production levels by the eukaryotic cell according to the present disclosure.

In one preferred embodiment, the activity of protein which uptake pyruvate form cytosol to mitochondria is increased in the eukaryotic cell according to the present disclosure. In one preferred embodiment, at least one subunit of the mitochondrial pyruvate carrier from S. cerevisiae is subject to overexpression. In one preferred embodiment, MPC1 (SEQ ID NO: 18) or MPC2 (SEQ ID NO: 19) or MPC3 (SEQ ID NO: 20) or any combinations of MPC1, MPC2, MPC3 is subject to overexpression. Surprisingly, it was found that overexpressing pyruvate carrier proteins resulted in increased L-ornithine production levels by the eukaryotic cell according to the present disclosure.

In one preferred embodiment, at least one enzyme/protein or any combinations of thereof is/are increased, the enzymes/proteins are as follows: isocitrate dehydrogenase, mitochondrial pyruvate carrier, pyruvate carboxylase, citrate synthase (CS), pyruvate dehydrogenase (PDH).

In one preferred embodiment, the carbon substrate uptake activity is decreased in the eukaryotic cell according to the present disclose. Many technologies/strategies known in the art can be used to decrease the activity of carbon substrate uptake. In one preferred embodiment, the carbon substrate uptake activity is decreased in the eukaryotic cell according to the present disclose, wherein the decrease activity of carbon uptake is achieved by decreasing the activity of the transport proteins which transport the carbon substrate from extracellular environment to the cytosol. Preferably, the decreasing of transport proteins which transport the carbon uptake is achieved by increase in the activity of special proteins which regulate the carbon uptake. In one preferred embodiment, stability of one of the proteins in the glucose regulation systems is achieved by overexpression the mutated MTH1 (SEQ ID NO: 22), encoding the internal deleted version of glucose transporter regulation protein. Surprisingly, more carbon flux from carbon substrate was boosted into L-ornithine and less or no ethanol production was seen with the modified S. cerevisiae.

In one preferred embodiment, the activity of the NADH alternative oxidase is increased to increase the efficiency of carbon channeling from carbon substrate to α-ketoglutarate in the modified eukaryotic cell. In one preferred embodiment, the activity of the NADH alternative oxidase is increased to increase the efficiency of carbon channeling from the carbon substrate to α-ketoglutarate in the modified yeast cell. In one preferred embodiment, the activity of the NADH alternative oxidase (AOX) is increased to increase the efficiency of carbon channeling from carbon substrate to α-ketoglutarate in the modified S. cerevisiae. In one preferred embodiment, the activity of the NADH alternative oxidase is increased to increase the efficiency of carbon channeling from carbon substrate to α-ketoglutarate in the modified S. cerevisiae, wherein the increased activity of AOX is achieved by overexpression of AOX from Hansenula anomala (HaAOX) (SEQ ID NO: 28). Surprisingly, more carbon flux from carbon substrate was boosted into L-ornithine and less or no ethanol production was seen with the modified S. cerevisiae.

In one preferred embodiment, the eukaryotic cell according to the present invention may be able to grow on any suitable carbon source known in the art and convert it to L-ornithine. The eukaryotic cell may be able to convert directly plant biomass, hemicelluloses, celluloses, pectines, rhamnose, fucose, maltose, galactose, maltodextrines, ribose, ribulose, or starch, starch derivatives, sucrose, glycerol and lactose. Hence, a preferred host organism expresses enzymes such as hemicellulases (e.g. endo- and exo-xylanases, arabinases) and cellulases (endocellulases and exocellulases) necessary for the conversion of cellulose into glucose monomers and hemicellulose into arabinose and xylose monomers, pectinases able to convert pectines into galacturonic acid and glucuronic acid or amylases to convert starch into glucose monomers. In one preferred embodiment, the modified eukaryotic cell is able to convert a carbon source selected from the group consisting of glucose, xylose, arabinose, fructose, galactose, sucrose, glycerol raffinose and lactose. In another aspect, the present invention relates to a process for the preparation of L-ornithine, comprising fermenting or cultivating the eukaryotic cell according to the present invention, wherein L-ornithine is prepared.

In one preferred embodiment, the L-ornithine produced by the modified eukaryotic cell described herein can be incorporated into one or more food, and/or chemical products.

In one preferred embodiment, the genetically modified eukaryotic cells according to the present disclose described herein can be incorporated into food and/or drink production. In one preferred embodiment, the genetically modified eukaryotic cells according to the present disclose described herein can be incorporated into beer brewing, wherein the beer comprises moderate L-ornithine. In one preferred embodiment, the genetically modified eukaryotic cells according to the present disclose described herein can be incorporated into bread baking, wherein the baking products comprise moderate L-ornithine.

In one preferred embodiment, the genetically modified eukaryotic cells according to the present disclose can be further modified to produce chemical compound which can be produced in the cell using L-ornithine as the precursor.

In certain embodiments, the present disclosure relates to a modified cell, such as yeast or bacterial cell, wherein the cell can overproduce polyamines, such as putrescine, spermidine or spermine. Said overproduction is obtained by combining some or all of the modifications for ornithine production mentioned above with overexpression of the enzymatic steps responsible for production of these compounds, down-regulation of competing and/or inhibitory reactions, overexpression of various export proteins, down-regulation of various uptake proteins and modification of expression of various proteins associated with polyamine toxicity, giving a very effective total process.

In a preferred embodiment, the activity of ornithine decarboxylase (ODC) which catalyzes the conversion of ornithine to putrescine is increased to increase flux towards putrescine in yeast. The increase in activity of ODC could be achieved by known methods in the art. For instance, the increased activity of ODC could be achieved by overexpressing the encoding gene of ODC. The ODC encoding gene can be from any known species, for instance *S. cerevisiae*. In one preferred embodiment the overexpression of the native SPE1 gene which encodes the ODC is achieved in the modified *S. cerevisiae*. In addition, heterologous ODC from other eukaryotic or prokaryotic sources can be expressed (e.g. from *Escherichia coli, Triticum aestivum, Oryza sativa, Glycine max, Citrus sinesis, Homo sapiens*). Furthermore, a mutated, highly-active ODC from *E. coli* containing modifications in the I163 and E165 residues can be expressed in yeast (Choi et al., 2015). To further increase the activity of ODC in yeast, the activity of the ODC antizyme, which binds to ODC, inactivates it, and targets it for degradation, could be decreased by deletion or promoter exchange. These modifications can be combined with the modifications for ornithine over-production described above. It has also been previously shown that deletion of Methylthioadenosine phosphorylase (encoded by MEU1) in yeast results in an increase in ODC activity and large elevation in polyamine pools (Subhi et al., 2003). Therefore, deletion or down-regulation of this gene can be combined with the above modifications. Furthermore, down-regulation of spermdine synthase (SPDS), which catalyzes conversion of putrescine to spermdine, can also be combined with the modifications above to increase flux towards putrescine.

In another embodiment, flux towards spermidine is increased in yeast by increasing the activities of S-adenosylmethionine decarboxylase (SAMDC) and spermidine synthase (SPDS), which catalyze conversion of putrescine into spermidine. This can be achieved by, for example, overexpression of the native SPE2 and SPE3 genes which encode SAMDC and SPDS in the modified *S. cerevisiae*. In addition, heterologous SAMDC and SPDS from other eukaryotic or prokaryotic sources can be expressed (e.g. from *Escherichia coli, Triticum aestivum, Oryza sativa, Glycine max, Citrus sinesis, Homo sapiens*). To further increase flux towards spermidine production, the SPE4 gene, which encodes spermine synthase (SPS), can be down-regulated. Flux towards spermidine can also be increased by overexpressing yeast polyamine oxidase (FMS1), which catalyzes conversion of spermine to spermidine, or spermine oxidase (SMOX; EC 1.5.3.16) from other sources (e.g. mammalian) for the same reaction. These modifications can be combined with the modifications for ornithine and/or putrescine over-production described above.

In another embodiment, flux towards spermine production is increased by increasing the activity of spermine synthase (SPS), which catalyzes the conversion of spermidine to spermine. This can be achieved by, for example, overexpression of the native SPE4 gene, which encodes SPS in the modified *S. cerevisiae*. In addition, heterologous SPS from other eukaryotic or prokaryotic sources can be expressed (e.g. from *Triticum aestivum, Oryza sativa, Glycine max, Citrus sinesis, Homo sapiens*). These modifications can also be combined with increase in the activities of ODC, SAMDC and/or SPDS, as well as down-regulation of the ODC antizyme. In addition, to reduce conversion of spermine to spermidine, yeast FMS1 can also be down-regulated.

In another embodiment, flux towards polyamines can be increased by down-regulation of competing reactions. For example, polyamine acetyltransferase (encoded by PAA1 in yeast) can acetylate various polyamines such as putrescine, spermidine and spermine. To reduce this, this enzyme can be down-regulated or deleted.

In another embodiment, export of polyamines to the media can be facilitated. This can be accomplished by overexpression of different export proteins, such as yeast TPO1, TPO2, TPO3, TPO4 and TPO5; *Escherichia coli* MdtJl, mammalian SLC3A2, *Bacillus subtillis* Bit transporter and/or mammalian MDR1. In addition, genes associated with polyamine uptake, such as yeast DUR3, SAM3, AGP2 and/or GAP1 can be down-regulated or deleted. Alternatively, increased intracellular presence of polyamines could be achieved by down-regulation or deletion of the polyamine transporters TPO1, TPO2, TPO3, TPO4 or TPO5.

In another embodiment, the resistance of the above strains to polyamine toxicity is increased. Down-regulation and/or deletion of several genes have been associated with increased resistance to polyamine toxicity in yeast. This includes SR protein kinase (SRPK) (encoded by SKY1), Putative serine/threonine protein kinase (encoded by PTK2), BRP1 and FES1. In addition, overexpression of several native genes has been associated with increased resistance to polyamine toxicity. This includes QDR3 and YAP1. The above genes can be over-expressed and/or down-regulated in various combinations to allow for optimal resistance to polyamine toxicity in yeast.

In certain embodiments, the present disclosure relates to a modified eukaryotic cell capable of over-producing agmatine. Said production can be accomplished either independently, or by combining some of the modifications described for ornithine production above with the overexpression of some of the enzymatic steps responsible for agmatine production and down-regulation of competing reactions.

In one embodiment, flux can be directed from ornithine to arginine and/or agmatine production by increasing the activities of ornithine carbamoyltransferase [EC:2.1.3.3], argininosuccinate synthase (EC:6.3.4.5) and argininosuccinate lyase [EC:4.3.2.1]. This can be done, for example, by overexpressing the native yeast ARG3, ARG1, ARG10 and/or ARG4 genes. In addition, heterologous genes encoding these activities can also be expressed. To decrease competing reactions, the native arginase (CAR1) genes can be deleted or down-regulated. Furthermore, conversion of arginine to agmatine can be accomplished by introduction of a heterologous gene encoding arginine decarboxylase [EC: 4.1.1.19] (e.g. *E. coli* SpeA or Adi, *Desulfovibrio magneticus* pdaA, *Homo sapiens* AZIN2, etc.).

In certain embodiments, putrescine can be produced from agmatine by introduction of genes encoding for enzyme activities of agmatinase (e.g *E. coli* SpeB), which converts agmatine to putrescine and urea (e.g *E. coli* SpeB). In addition, agmatine could also be converted to putrescine by introduction of two heterologous steps: hydrolytic deamination of agmatine to N-carbamoylputrescine by agmatine deiminase (e.g. AguA from *Pseudonomas aeroginosa*) and hydrolysis of the carbomoyl group to yield putrescine in a reaction catalyzed by N-carbamoylputrescine amidohydrolyase (e.g. AguB from *Pseudonomas aeroginosa*; PTC from *Enterococcus faecalis*).

In certain embodiments, spermidine can be produced from agmatine. In some extremophiles, agmatine aminopropyltransferase uses S-adenosylmethionine (dsSAM) as a donor to produce aminopropylagmatine which is subsequently hydrolysed to spermidine and urea by aminopropylagmatine ureohydrolase. Genes encoding enzymes for these activities can also be expressed in yeast to facilitate spermidine production (e.g. *Thermococcus kodakarensis* TK0147, TK0240, TK0474 and TK0882, *Thermus thermophiles* speE and speB).

In a another embodiment, spermidine can be produced via the condensation of L-aspartate semialdehyde and putrescine via carboxy(nor)spermidine dehydrogenase (CANSDH) yielding carboxyspermidine, followed by decarboxylation by carbox(nor)spermidine decarboxylase (CANSDC). Genes encoding enzyme with these activities can be expressed to facilitate spermidine production (e.g. CANSDH and CANSDC from *Campylobacter jejuni*, *Vibrio cholera*, *Vibrio cholerae* or *Vibrio alginolyticus*). Alternatively, aminopropyl transferase activity which uses dcSAM to synthesize norspermidine from 1,3-diaminopropane from *Clostridium thermohydrosuluricum* can also be expressed.

In certain embodiments, additional reactions that could potentially compete with polyamine synthesis could be deleted or down-regulated in yeast. This can include reactions involved in pathways that lead to GABA (γ-aminobutyric acid), such as those encoded by UGA1, UGA2, UGA3 and/or UGA4).

In certain embodiments, production of polyamines from bacterial sources can be achieved. For production of L-ornithine and putrescine, organisms like *Escherichia coli* and *Corynebacterium glutanicum* are feasible hosts for production. This makes them good platform strains for the production for spermidine and spermine through overexpression of intrinsic or heterologous spermidine synthase and S-adenosylmethionine decarboxylase. Modifications in *E. coli* WL3110 (orig. K12 W3110 (CGSC, *Coli* Genetic Stock Center) to increase ornithine and putrescine production respectively can be implemented as described by Quian et al. (2009). For example, such modifications can comprise enhancing the precursor supply (e.g., deletion of argI gene), inactivating putrescine degradation and utilization pathways (e.g., deletion of speG; puuPA, argR) and deleting rpoS, a stress responsive polymerase sigma factor. In addition to, or combined with the former changes, genes coding for ornithine decarboxylase converting ornithine to putrescine and ornithine biosynthetic genes (argC-E) can be overexpressed either through the use of plasmids or chromosomal integration. This former platform strain can additionally be transformed with either plasmids for overexpression of endogenous or heterologous speE (E.C.: 2.5.1.16; SEQ ID NO: 37) and speD (EC 4.1.1.50; SEQ ID NO: 39) genes. Spermidine exporters derived from, for example, *E. coli*, including the mdtJI complex genes (SEQ ID NOs: 40-41) or Blt from, for example, *B. subtilis* (SEQ ID NO: 42) represent possible candidates for over/co-expression with the "platform" stain described herein to increase the production of spermidine/spermine. In other embodiments, in order to increase the production of spermine, heterologous spermine synthases (E.C. 2.5.1.22) from, for example, eukaryotic sources, including *S. cerevisiae*, *Triticum aestivum*, *Oryza sativa*, *Glycine max*, *Citrus sinesis*, *Homo sapiens* can be expressed.

In yet other embodiments, polyamines can be produced in *C. glutamicum*. Modifications to increase ornithine production in *C. glutamicum* strain ATCC 13032 can be achieved through, for example, deletion of proB and argF, which block competing pathways, deletion of argR gene, which is the repressor of the L-arginine operon, overexpression of argCJBD from *C. glutanicum* (ATCC 21831 start codon change of pgi and zwf), which lead to enrichment of the NADPH pool, and/or replacing native promoter of tkt operon with a strong sod promoter. In some embodiments, in order to increase putrescine production the platform strain can be engineered to overexpress the ornithine decarboxylase gene, speC (EC 4.1.1.19; SEQ ID NO: 44) from *E. coli* and/or by deletion of the carbamoyl-transferase argF gene.

In some embodiments, in order to increase spermidine production in the platform strain, the endogenous spermidine synthase gene speE (SEQ ID NO: 45) and *E. coli* S-adenosylmethionine decarboxylase speD (EC 4.1.1.50; SEQ ID NO: 39) can be overexpressed. The former strains can additionally be engineered to increase the export, as described elsewhere herein. In other embodiments in order to increase spermidine, heterologous spermine synthases (E.C. 2.5.1.22) from eukaryotic sources can be overexpressed. For example, the former spermine synthases can be derived from, for example, *S. cerevisiae* (Spe4, GI: 3201942; SEQ ID NO: 43), *Triticum aestivum*, *Oryza sativa*, *Glycine max*, *Citrus sinesis* and/or *Homo sapiens*.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

In general, any modification may be applied to a cell to impart or increase accumulation and/or production of L-ornithine or a chemical compound which can be produced in the cell using L-ornithine. In many cases, the modification comprises a genetic modification, wherein the genetic modifications may be introduced into cells by any available means including transfer (e.g., via transformation or mating) of nucleic acids and/or chemical mutation.

An aspect of the embodiments relates to a eukaryotic cell capable of producing L-ornithine. The eukaryotic cell is genetically modified for attenuated activity of an ornithine carbamyoltransferase.

In an embodiment, the eukaryotic cell is genetically modified for attenuated expression of a gene encoding the ornithine carbamyoltransferase in the eukaryotic cell.

In an embodiment, the eukaryotic cell has a native promoter of the gene encoding the ornithine carbamyoltransferase replaced by a weak constitutive promoter. In a particular embodiment, the eukaryotic cell has a native promoter of the gene ARG3 replaced by a promoter of the gene KEX2.

In an embodiment, the eukaryotic cell is genetically modified by deletion or disruption of a gene encoding an L-ornithine transaminase. In a particular embodiment, the eukaryotic cell is genetically modified by deletion or disruption of the gene CAR2.

The above disclosed embodiments relates to a eukaryotic cell, such as fungal cell and preferably a yeast cell, genetically modified according to module 1 (M1) as described herein.

In an embodiment, the eukaryotic cell is genetically modified for enhanced L-ornithine biosynthesis from α-ketoglutarate.

In an embodiment, the eukaryotic cell is genetically modified for cytosolic L-ornithine biosynthesis from α-ketoglutarate.

In an embodiment, the eukaryotic cell comprises at least one of gene selected from a group consisting of a gene encoding a cytosolic glutamate N-acetyltransferase, a gene encoding a cytosolic N-acetylglutamate kinase, a gene encoding a cytosolic N-acetyl-gamma-glutamyl-phosphate reductase, a gene encoding a cytosolic acetylornithine aminotransferase and a gene encoding a cytosolic ornithine acetyltransferase. In a particular embodiment, the eukaryotic cell comprises the genes argA$_{Ec}$ and argB$_{Ec}$ from *Escherichia coli* and the genes argC$_{Cg}$, argD$_{Cg}$ and argJ$_{Cg}$ from *Corynebacterium glutamicum*.

In an embodiment, the yeast is genetically modified for overexpression of at least one gene selected from a group consisting of a gene encoding an N-acetyl-gamma-glutamyl-phosphate reductase, a gene encoding a mitochondrial ornithine acetyltransferase, a gene encoding an acetylornithine aminotransferase and a gene encoding an acetylglumate synthase. In a particular embodiment, the yeast is genetically modified for overexpression of the genes ARG5, 6 ARG7, ARG8 and ARG2.

In an embodiment, the eukaryotic cell is genetically modified for overexpression of at least one gene selected from a group consisting of a gene encoding a L-ornithine transporter, a gene encoding a L-glutamate transporter and a gene encoding NADP+-dependent glutamate dehydrogenase. In a particular embodiment, the eukaryotic cell is genetically modified for overexpression of the genes ORT1, AGC1, GDH1.

The above disclosed embodiments relates to a eukaryotic cell, such as fungal cell and preferably a yeast cell, genetically modified according to module 2 (M2) as described herein. As mentioned above, the genetical modification according to module 2 is preferably applied to a eukaryotic cell that also is genetically modified according to module 1. However, the embodiments are not limited. Thus, an aspect of the embodiments relates to a yeast cell genetically modified according to module 2 but not necessarily according to module 1. This aspect of the embodiments thereby relates to a eukaryotic cell capable of producing L-ornithine. The eukaryotic cell is genetically modified for enhanced L-ornithine biosynthesis from α-ketoglutarate. The above described optional but preferred embodiments relating to the genetical modification according to module 2 also applies to the aspect of a eukaryotic cell genetically modified according to module 2 but not necessarily according to module 1.

In an embodiment, the eukaryotic cell is genetically modified for enhanced α-ketoglutarate biosynthesis.

In an embodiment, the eukaryotic cell is genetically modified for attenuated glucose uptake.

In an embodiment, the eukaryotic cell is genetically modified for overexpression of a gene encoding a glucose transporter regulator protein. In a particular embodiment, the eukaryotic cell is genetically modified for overexpression of the gene MTH1 or the gene MTH1-ΔT, wherein the gene MTH1-ΔT is an internal deletion version of the gene MTH1.

The above disclosed embodiments relates to a eukaryotic cell, such as fungal cell and preferably a yeast cell, genetically modified according to module 3 (M3) as described herein. As mentioned above, the genetical modification according to module 3 is preferably applied to a eukaryotic cell that also is genetically modified according to module 1 and module 2. However, the embodiments are not limited. Thus, an aspect of the embodiments relates to a yeast cell genetically modified according to module 3 but not necessarily according to module 1 or module 2. This aspect of the embodiments thereby relates to a eukaryotic cell capable of producing L-ornithine. The eukaryotic cell is genetically modified for enhanced α-ketoglutarate biosynthesis. The above described optional but preferred embodiments relating to the genetic modification according to module 3 also applies to the aspect of an eukaryotic cell genetically modified according to module 3 but not necessarily according to module 1 or module 2.

Thus, the embodiments encompass a eukaroytoic cell genetically modified according to module 1, a eukaryotic cell genetically modified according to module 2, a eukaryotic cell genetically modified according to module 3, a eukaryotic cell genetically modified according to module 1 and module 2, a eukaryotic cell genetically modified according to module 1 and module 3, a eukaryotic cell genetically modified according to module 2 and module 3 and a eukaryotic cell genetically modified according to module 1, module 2 and module 3.

In an embodiment, the eukaryotic cell is genetically modified for overexpression of a gene encoding an arginase. In a particular embodiment, the eukaryotic cell is genetically modified for overexpression of the gene CAR1.

The above described embodiments and particular embodiments can be combined in any suitable manner. Hence, the present invention also encompasses various combinations of different genetical modifications of the above described embodiments to form a eukaryotic cell capable of producing L-ornithine.

In an embodiment, the eukaryotic cell is genetically modified by:
having a native promoter of the gene ARG3 replaced by a promoter of the gene KEX2;
deletion or disruption of the gene CAR2;
overexpression of the genes ORT1, AGC1, GDH1;
expression of the genes argA$_{Ec}$ and argB$_{Ec}$ from *Escherichia coli* and the genes argC$_{Cg}$, argD$_{Cg}$ and argJ$_{Cg}$ from *Corynebacterium glutamicum*; and
overexpression of the gene MTH1-ΔT.

In an embodiment, the eukaryotic cell is also genetically modified for overexpression of the gene CAR1.

Further aspects of the embodiments relates to a eukaryotic cell capable of producing a polyamine using L-ornithine as a starting material or intermediate product in the production of the polyamine. In a preferred embodiment, the polyamine is selected from a group consisting of putrescine, spermidine and spermine.

Thus, in embodiment the eukaryotic cell is capable of producing a polyamine selected from the group consisting of putrescine, spermidine and spermine. The eukaryotic cell is also genetically modified for overexpression of a gene encoding ornithine decarboxylase (ODC) and/or attenuated activity of ODC antienzyme.

In a particular embodiment, the eukaryotic cell is genetically modified for overexpression of the gene SPE1 and deletion or disruption of the gene OAZ1.

In an embodiment, the eukaryotic cell is capable of producing a polyamine selected from the group consisting of spermidine and spermine. The eukaryotic cell is also genetically modified for overexpression of a gene encoding an S-adenosylmethionine decarboxylase and/or a gene encoding a spermidine synthase.

In a particular embodiment, the eukaryotic cell is genetically modified for overexpression of the genes SPE2 and SPE3.

In an embodiment, the eukaryotic cell is capable of producing a polyamine selected from the group consisting of spermidine and spermine. The eukaryotic cell is also genetically modified for expression of a gene encoding a carboxynorspermidine dehydrogenase and/or a gene encoding a carboxynorspermidine decarboxylase.

In a particular embodiment, the eukaryotic cell is genetically modified for expression of:
i) the genes Cj0172c and Cj1515c from *Campylobacter jejuni*; or
ii) the genes VC1624 and VC1623 from *Vibrio cholera*; or
iii) the genes Lys1 and nspC from *Bacteroides uniformis*.

In an embodiment, the eukaryotic cell is capable of producing spermine. The eukaryotic cell is also genetically modified for overexpression of a gene encoding a spermine synthase.

In a particular embodiment, the eukaryotic cell is genetically modified for overexpression of the gene SPE4.

In an embodiment relating to the eukaryotic cell capable of producing a polyamine, the eukaryotic cell is genetically modified for overexpression of a gene encoding a polyamine transporter. In a particular embodiment, the eukaryotic cell is genetically modified for overexpression of at least one gene selected from the group consisting of TPO1, TPO2, TPO3, TPO4 and TPO5.

In an embodiment, the eukaryotic cell capable of producing L-ornithine and optionally the polyamine is a fungal cell, preferably a yeast cell.

In an embodiment, the yeast cell is selected from a genus consisting of the group consisting of *Saccharomyces, Cryptococcus, Trichosporon, Zygosaccharomyces, Debaromyces, Pichia, Schizosaccharomyces, Trigonopsis, Brettanomyces, Aureobasidium, Nadsonia, Lipomyces, Torulopsis, Kloeckera, Phaffia, Rhodotorula, Candida, Hansenula, Kluyveromyces, Yarrowia*, and *Schwanniomyces*. In a particular embodiment, the yeast cell is selected from a genus consisting of the group consisting of *Saccharomyces, Yarrowia, Zygosaccharomyces, Kluyveromyces* and *Pichia* spp. In an embodiment, the yeast cell is preferably selected from the group consisting of *Saccharomyces cerevisiae, Saccharomyces boulardii, Zygosaccharomyces bailii, Kluyveromyces lactic, Yarrowia lipolytica, Schizosaccharomyces pombe, Hansenula anomala, Candida sphaerica*, and *Schizosaccharomyces malidevorans*, such as *Saccharomyces cerevisiae*.

A further aspect of the embodiments relates to a process for production of L-ornithine. The process comprising cultivating a eukaryotic cell according to any of the embodiments disclosed herein and in particular mentioned in the foregoing in the presence of a carbon source.

Yet another aspect of the embodiments relates to a process for production of a polyamine selected from the group consisting of putrescine, spermidine and spermine. The process comprising cultivating a eukaryotic cell according to the embodiments above relating to a eukaryotic cell capable of producing a polyamine in the presence of a carbon source.

In an embodiment, the carbon source is selected from a group consisting of hemicelluloses, celluloses, pectines, rhamnose, fucose, maltose, galactose, maltodextrines, ribose, ribulose, starch, sucrose, glycerol, lactose, glucose, xylose, arabinose, fructose, galactose and glycerol raffinose and lactose.

EXAMPLES

All engineered yeast strains were constructed (Table 1-3) from *S. cerevisiae* strain CEN.PK 113-11C (MAT a SUC2 MAL2-8c his3Δ1 ura3-52).

Example 1

Strain Construction of Ornithine-Overproducing Strains

All the plasmids used in this study can be found in Table 4. Plasmids (GO1, GO2, GO3, GO4, YO1, YO2, YO3 YO4 and YO3) were constructed according to MOPE strategy and DNA assembler (Shao et al., 2009). The gene expressing modules consisted of a promoter, a structural gene, a terminator, and the promoter of the next module for homologous recombination. The promoter TEF1p, TDH3p, PGK1p and HXT7p, terminator FBA1t, CYC1t, TDH2t and ADH2t, were PCR-amplified from the genomic DNA of *S. cerevisiae* CEN.PK.113-5D. The TPlp and the terminator pYX212t were PCR-amplified from plasmid pYX212. Genes ARG2, ARG5, 6, ARG7, ARG8, CIT1, ACO2, IDP1, PYC2, GLT1 and GLN1 were amplified from the genomic DNA of *S. cerevisiae* CEN.PK.113-5D. PDA1 and mutated mPDA1 were PCR-amplified from plasmid pRS416-PDA1 and pRS416-PDA1 [S313A] respectively (Oliviera et al., 2012). HoAOX1, $argJ_{Cg}$, $argC_{Cg}$, $argD_{Cg}$, and $argB_{Cg}$ were codon-optimized and purchased from GenScript. $argA_{Ec}$ and $argB_{Ec}$ were PCR-amplified from the genomic DNA of *E. coli*. The mutated MTH1-ΔT was PCR-amplified from the genomic DNA of *S. cerevisiae* TAM (Oud et al., 2012). $argB_{Cg}$, and $argJ_{Cg}$ were targeted to the mitochondria using the N-terminal mitochondrial localization signal from subunit IV of the yeast cytochrome c oxidase (CoxIV) (Avalos et al., 2013). All modules were constructed with the one-step PCR strategy similar to overlap extension PCR. The expression modules were co-transformed by electroporation with linearized vector pYX212 or p423GPD into *S. cerevisiae* CEN.PK 113-11C, and the recombinants appeared on the corresponding plates after 2-4 days. Selected colonies formed on the plates were cultured in 5 mL of YPD liquid medium at 30° C. for 72 h. Recovered plasmids were checked by PCR to verify the assembled pathways. Alternatively, positive plasmids were also transformed into *E. coli* DH5α, recovered, digested by the relative restriction endonuclease, and analyzed by gel electrophoresis. Other plasmids used in this study were constructed according to the regular cloning strategy.

To replace the ARG3 promoter, the HXT1 promoter and KEX2 promoter were amplified from genomic DNA by PCR. The DNA cassette including the new promoter, the kanMX cassette and both 5' and 3' parts of the ARG3 promoter was constructed following the strategy of MOPE. Following the transformation of these cassettes into *S. cerevisiae*, the correct transformants were selected and verified by colony PCR. Following a similar strategy, ORT1, ODC1, AGC1, GDH1, GDH2, GDH3, HaAOX1 and MTH1-ΔT were integrated into the chromosome of *S. cerevisiae* background strains, yielding strains with modification in the URA3, YPRCT3 or KGD2 sites of chromosome (Flagfeldt et al., 2009). Similar to $argB_{Cg}$ and $argJ_{Cg}$, GDH1 and GDH2 were targeted to the mitochondria using the N-terminal mitochondrial localization signal from subunit IV of the yeast cytochrome c oxidase (CoxIV). Variation combinations of plasmids and background strains yielded L-ornithine producing strains.

Yeast strains without plasmids were maintained on YPD plates containing 10 g $l^{-1}$ yeast extract, 20 g $l^{-1}$ casein peptone, 20 g $l^{-1}$ glucose and 20 g $l^{-1}$ agar. Plasmid carrying yeast strains were selected on synthetic dextrose (SD) agar containing 6.9 g $l^{-1}$ yeast nitrogen base w/o amino acids (Formedium, Hunstanton, UK), 20 g $l^{-1}$ glucose, and 20 g $l^{-1}$ agar. Strains containing the kanMX cassette were selected on YPD plates containing 200 mg $l^{-1}$ G418 (Formedium, Hunstanton, UK). Defined minimal medium (Delft medium) as described before was used for both batch cultivations and fed-batch fermentations of L-ornithine producing strains (Scalcinati et al., 2012). Luria Bertani (LB) broth with 80 mg 1-1 ampicillin was used for maintenance of *E. coli* DH5α harboring appropriate plasmids. L-ornithine was quantified using a ninhydrin colorimetric assay as described previously (Chinard, 1952).

Example 2

L-Arginine Leaky Auxotroph Enables L-Ornithine Overproduction

As an intermediate of L-arginine biosynthesis in *S. cerevisiae*, L-ornithine can be converted to L-citrulline catalyzed by ornithine carbamoyltransferase (ARG3) in cytoplasm after export from the mitochondria, and L-ornithine biosynthesis rate is limited by the presence of L-arginine due to the feedback inhibition and repression of the key enzymes. However, deletion of ARG3 results in a L-arginine auxotrophy and a need of L-arginine supplementation, which adds additional costs and might take problems in large-scale process control. Thus, as part of this invention, we tested whether fine-tuning the ARG3 expression rather than full blocking would be a better strategy, as L-arginine can still be synthesized at controllable lower level to support the growth and also can limit the negative regulation of L-arginine on L-ornithine biosynthesis. Since promoter replacement can be a feasible strategy, we first weakened the ARG3 expression by replacing its native promoter with the promoter of HXT1 (Low-affinity glucose transporter of the major facilitator superfamily) and KEX2 ($Ca^{2+}$ dependent serine protease involved in protein processing)(Scalcinati et al. 2012) (FIG. 1a). To replace the ARG3 promoter, the HXT1 promoter and KEX2 promoter were amplified from genomic DNA of *S. cerevisiae* strain CEN.PK113-5D by PCR. The DNA cassette including the new promoter, the kanMX cassette and both 5' and 3' parts of the ARG3 promoter was constructed following the strategy of MOPE as described in Example 1 above. Following the transformation of these cassettes into *S. cerevisiae*, the correct transformants were selected and verified by colony PCR. This resulted in strains M1a (HXT1) and M1b (KEX2).

Figure 1B:
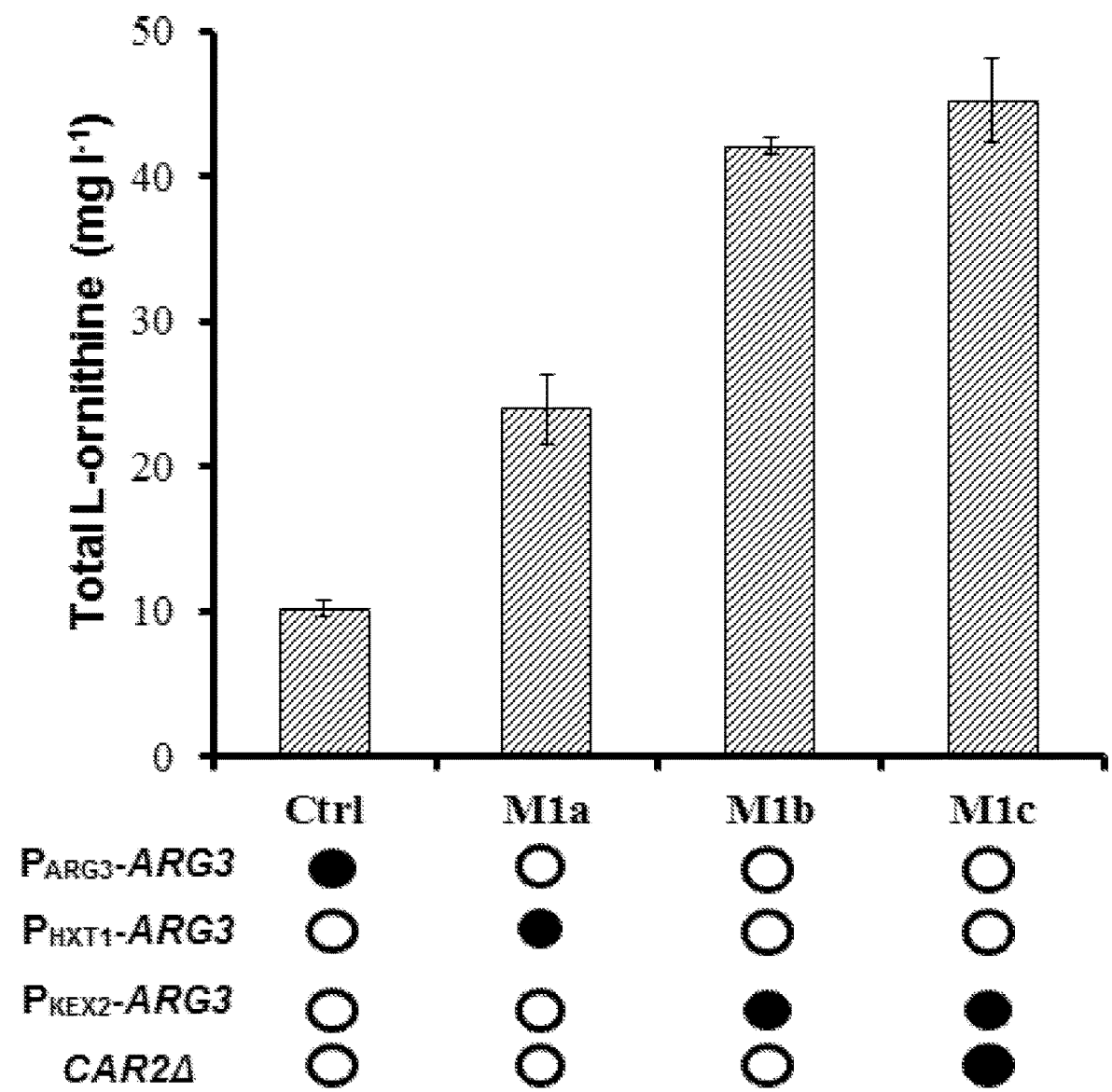
Figure 1C:
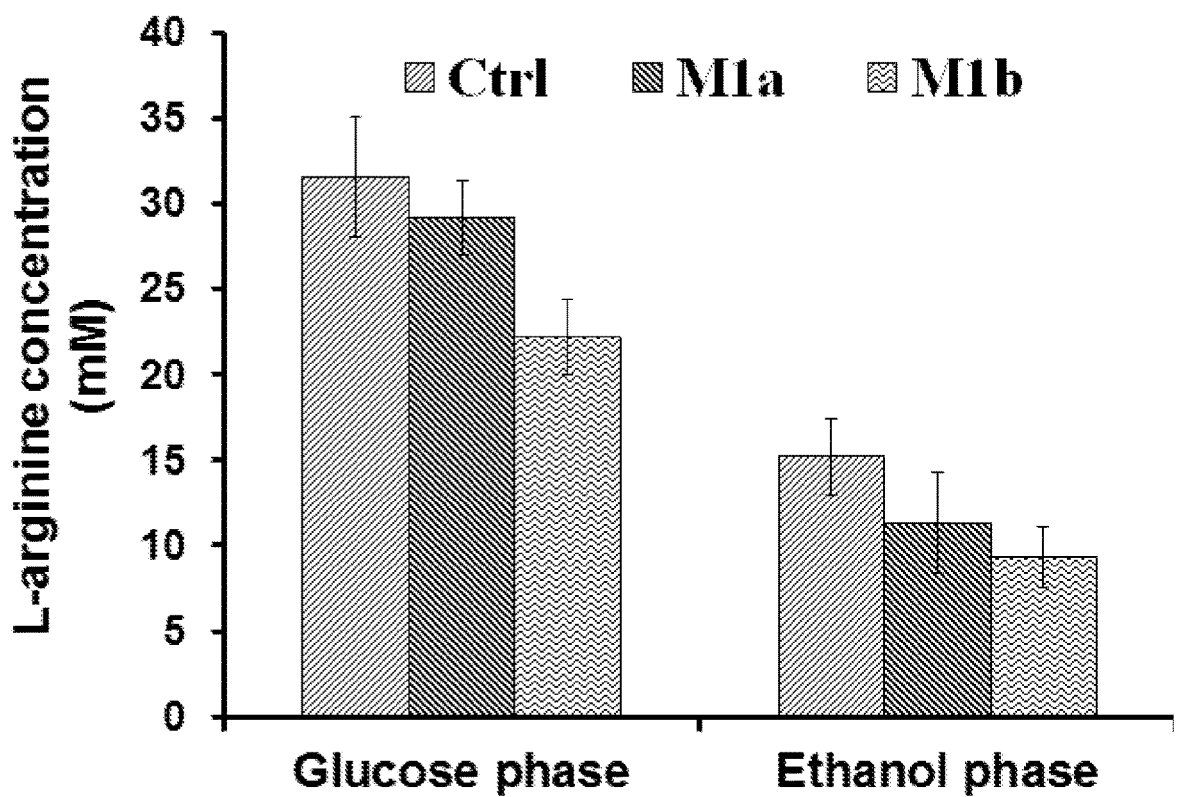

This strategy resulted in increased production of ornithine (FIG. 1b), with both strains in which the ARG3 promoter was replaced with a weaker promoter displaying improved overall production. The choice of promoter was also highly relevant to ornithine production, wherein the strain with the weakest promoter (KEX2) had a 75% higher titer (42 mg/L) compared to the strain with the HXT1 promoter (24 mg/L) as shown in FIG. 1b.

Example 3

Pathway Re-Localization and Subcellular Trafficking Engineering Elevates L-Ornithine Synthesis After the optimization of L-ornithine consumption, we optimized the L-ornithine biosynthesis pathway from α-ketoglutarate, the intermediate of the TCA cycle. This part of L-ornithine synthesis is notable for its complicated metabolic compartmentation, where key metabolites, such as L-glutamate, α-ketoglutarate and L-ornithine, are synthesised in different organelle. Thus, the specific biosynthesis pathway as well as the intermediates transportation/shutting should be co-ordinately optimized.

Figure 2A:
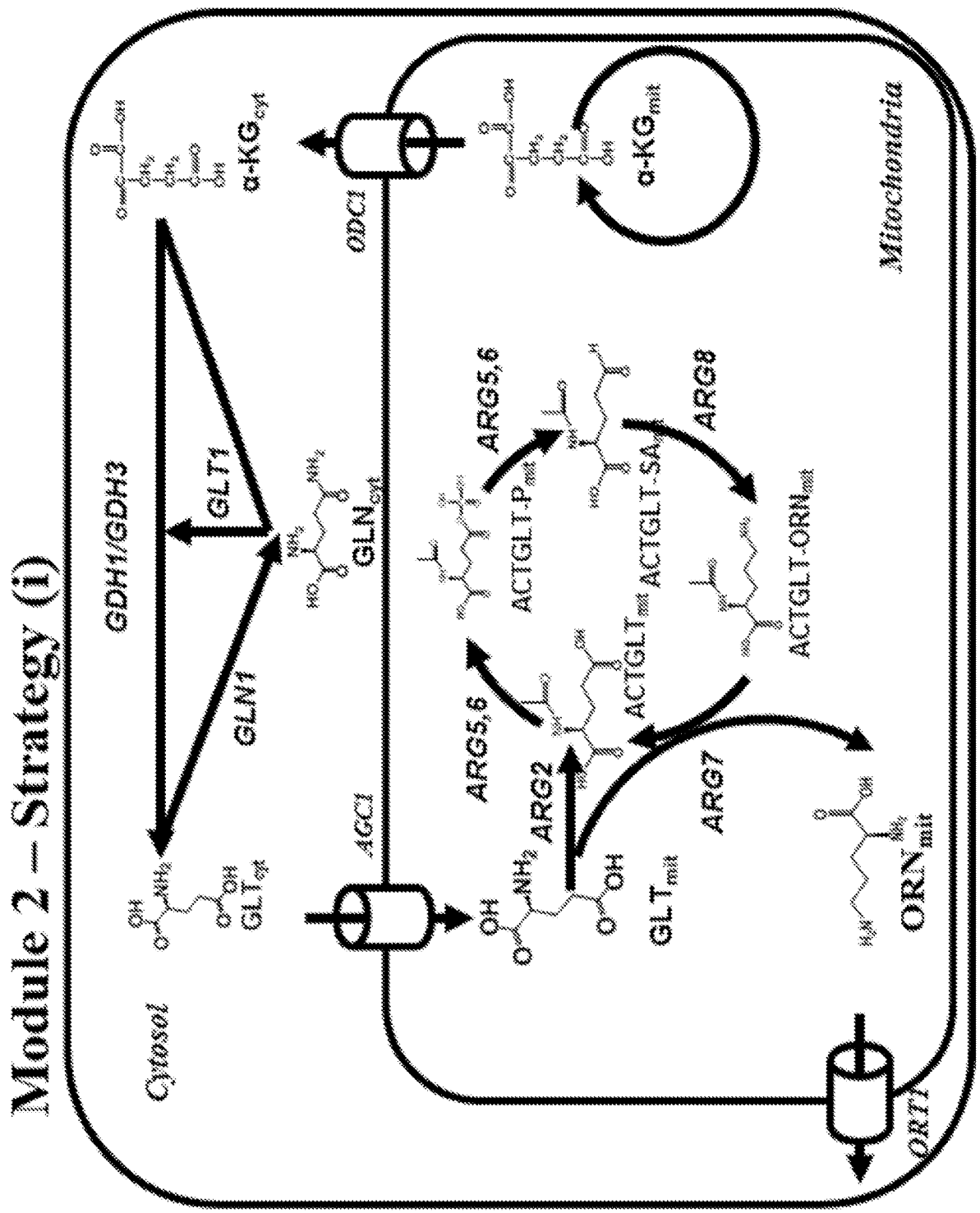
FIG. 2: Improved L-ornithine production by optimizing the flux from α-ketoglutarate to L-ornithine 'acetylated derivatives cycle'. Three strategies were proposed to eliminate the obstacles in the Module 2 as follows: (a) Strategy (i), intrinsic pathways including intracellular trafficking steps of Module 2 was strengthened; (b) Strategy (ii), L-glutamate dehydrogenase reaction was proposed to be re-localized to the mitochondria to bypass the potential intracellular trafficking of α-ketoglutarate and (c). Strategy (iii), L-glutamate and chimeric L-ornithine 'acetylated derivatives cycle' from bacteria was re-localized to cytosol to bypass the potential obstacles of intracellular metabolites' trafficking. (d) Pathway variants of Strategy (i) and Strategy (iii) in Module 2 enable substantial increase of L-ornithine titers. All the strains were cultivated for 72 h in definite Delft medium. All data are presented as the mean±s.d. (n≥0.3).
Figure 2B:
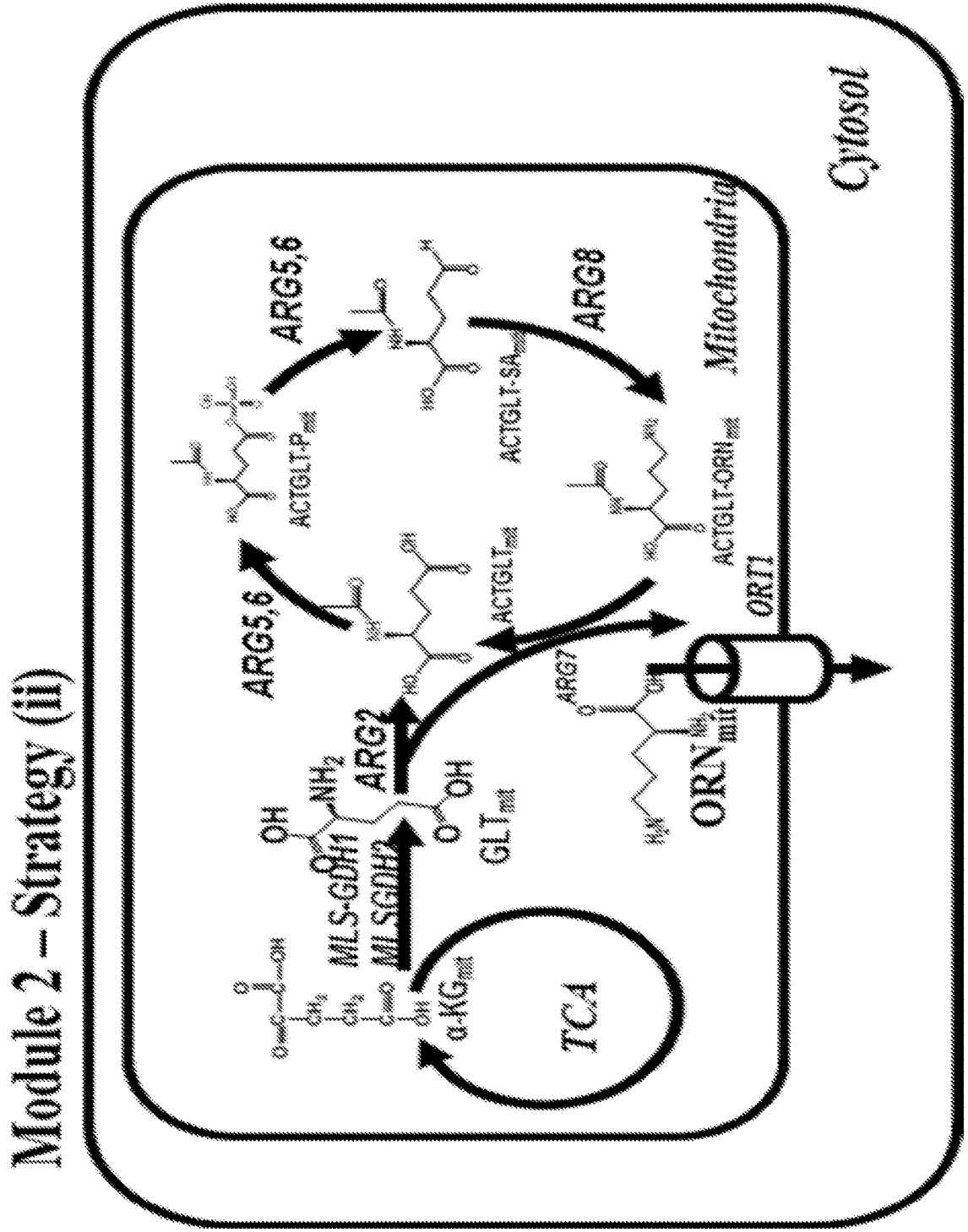
Figure 2C:
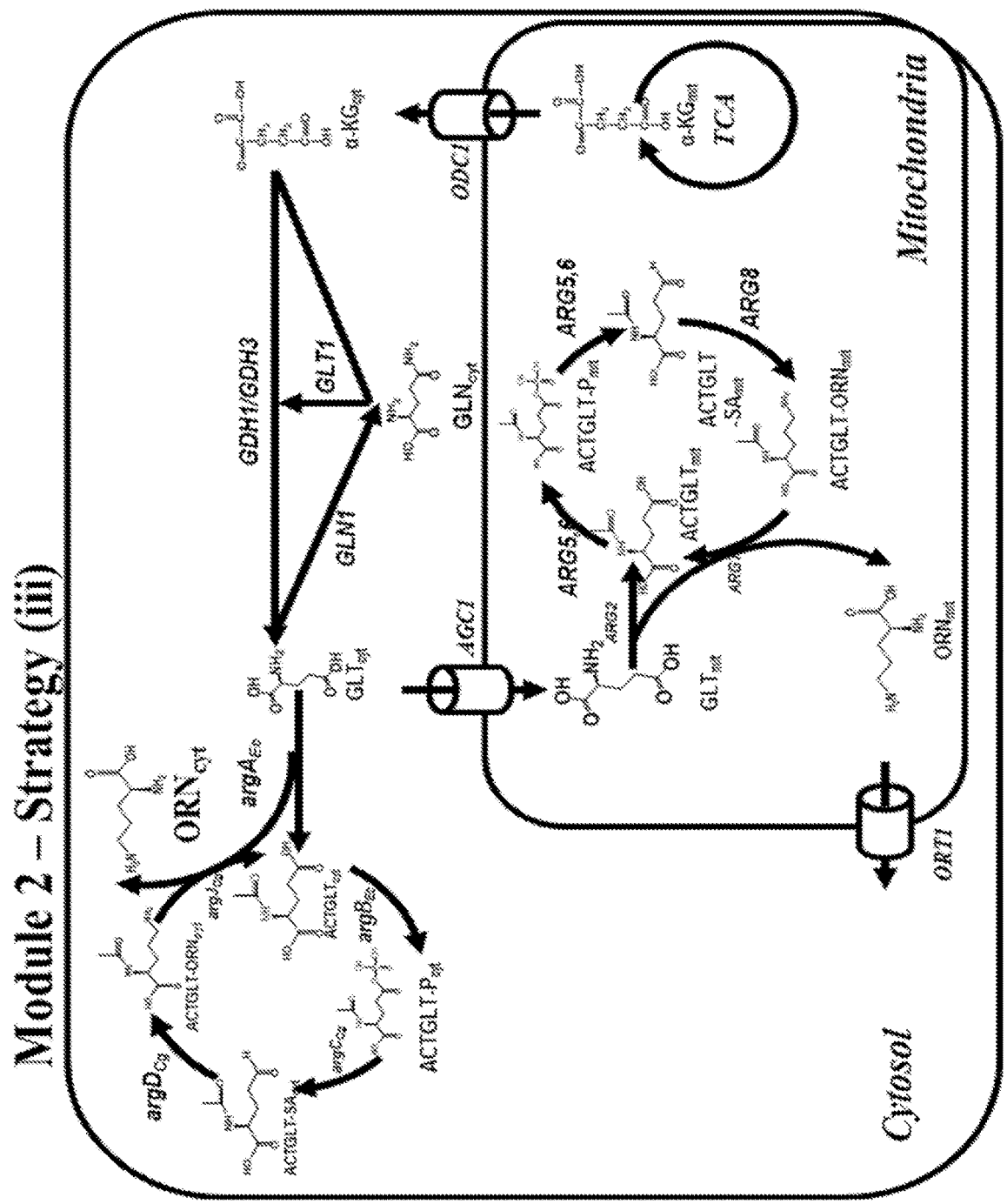

We started at managing the nature of compartmentalization to efficiently improve the L-ornithine titers (FIGS. 2a, 2b and 2c). We first set out to enhance the L-ornithine synthesis pathway from L-glutamate in mitochondria.

CAR2 was initially deleted from strain M1b using a bipartite strategy (Erdeniz et al., 1997). Two overlapping fragments of the kanMX resistance marker cassette flanked by loxP sites were amplified via PCR from plasmid pUG6 (Guldener et al., 1996). Sequences upstream and downstream of CAR2 were also amplified. Due to overlapping ends (introduced through the primer sequences) the CAR2-upstream fragments could be fused to the 5' kanMX fragment and the 3' kanMX fragment to the individual CAR2-downstream fragments by fusion PCR using the outer primers for amplification. The two overlapping PCR fragments thus generated for each gene deletion were transformed into yeast using the lithium acetate method (Gietz and Woods, 2002). This resulted in the stain ORN-E (KanMX). The strain with the CAR2 deletion displayed a slight increase in ornithine production (FIG. 1b). Next, the genes ARG5, 6 (EC.1.2.1.38; 2.7.2.8; SEQ ID NO: 3), ARG7 (EC 2.3.1.35; SEQ ID NO: 5) and ARG8 (EC 2.6.1.11; SEQ ID NO: 4) were amplified from the genomic DNA of *S. cerevisiae* CEN.PK.113-5D and constructed into the GO1 plasmid according to MOPE strategy and DNA assembler as described in Example 1 above. The strain ORN-E(KanMX) was transformed with either two empty plasmids (pYX212 and p423GPD) yielding strain M1c, or with an empty URA-based plasmid (pYX212) and GO1 to yield strain M1cM2f.

Figure 2D:
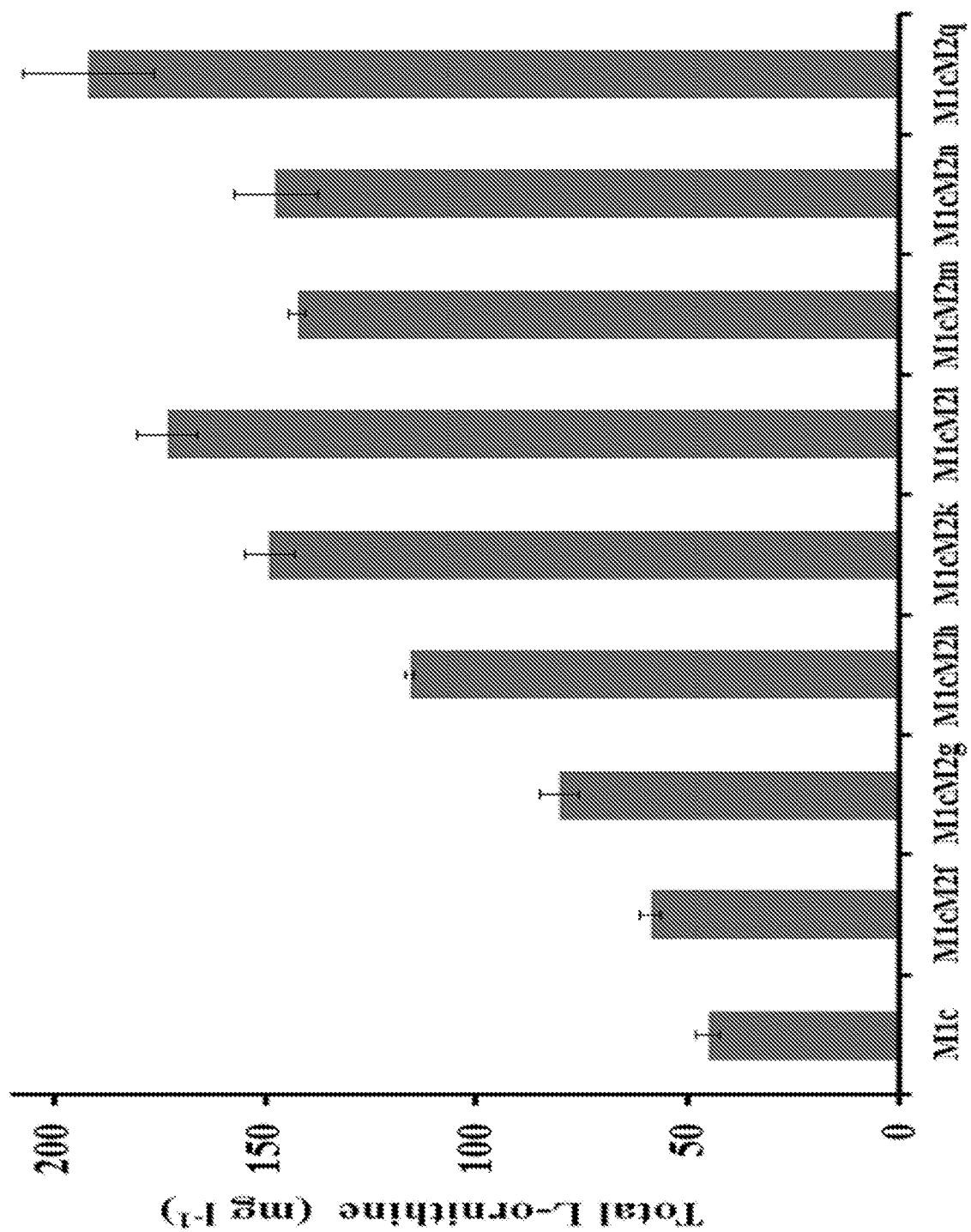

Systematic overexpression of ARG5, 6, ARG7 and ARG8 in strain M1cM2f, increased L-ornithine titers to 59 mg $l^{-1}$, representing a 31% increase as compared to the control (strain M1c)(FIG. 2d). This part of the pathway is known as the acetylated derivatives cycle because the acetyl group that is added to L-glutamate in the first step of the pathway is recycled via N-acetylglutamate generated in the fifth step. We speculated that if the activity of the first step which is catalysed by N-acetyl-ornithine synthase (NAGS, encoding by ARG2; EC 2.3.1.1) was increased, the further L-ornithine titers should improve. To overexpress ARG2 (SEQ ID NO: 2), this gene was amplified from the genome of *S. cerevisiae* CEN.PK113-5D strain and cloned into a plasmid together with ARG5, 6, ARG7 and ARG8 using the MOPE strategy, resulting in plasmid GO2. This plasmid was co-transformed into strain ORN-E(KanMX) along with pYX212, resulting in strain M1cM2g. This strain produced 80 mg of L-ornithine, leading to an 36% increasing as compared to the strain expressing only ARG5, 6, ARG7 and ARG8 (strain M1cM2f)(FIG. 2d). Indeed, while the ARG2 overexpression could improve the efficiency of initial step in the said L-ornithine pathway, it also fulfils an anaplerotic role to replenish the pathway intermediates that are lost due to degradation or cell division.

Figure 8:
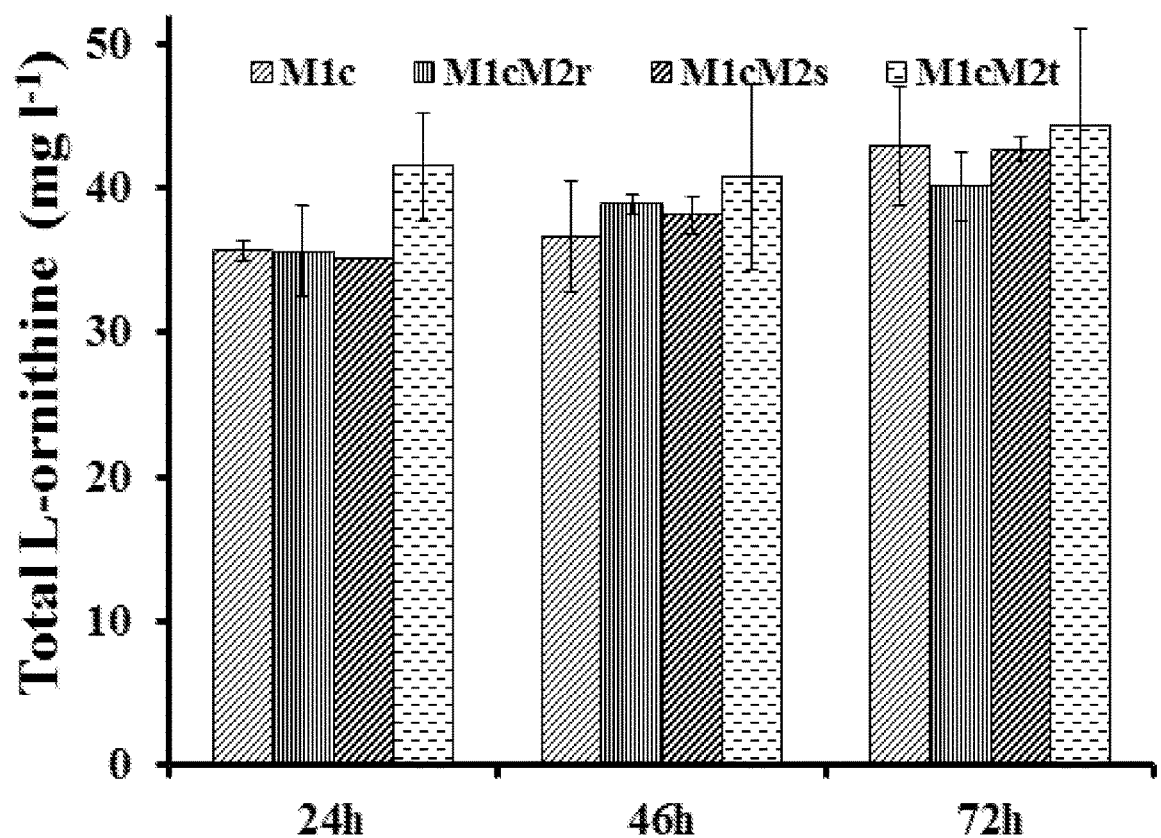
FIG. 8: The effect of truncated Gcn4p overexpression on L-ornithine titers. All the strains were cultivated for 72 h in definite Delft medium. All data are presented as the mean±s.d. (n≥3).
Figure 9:
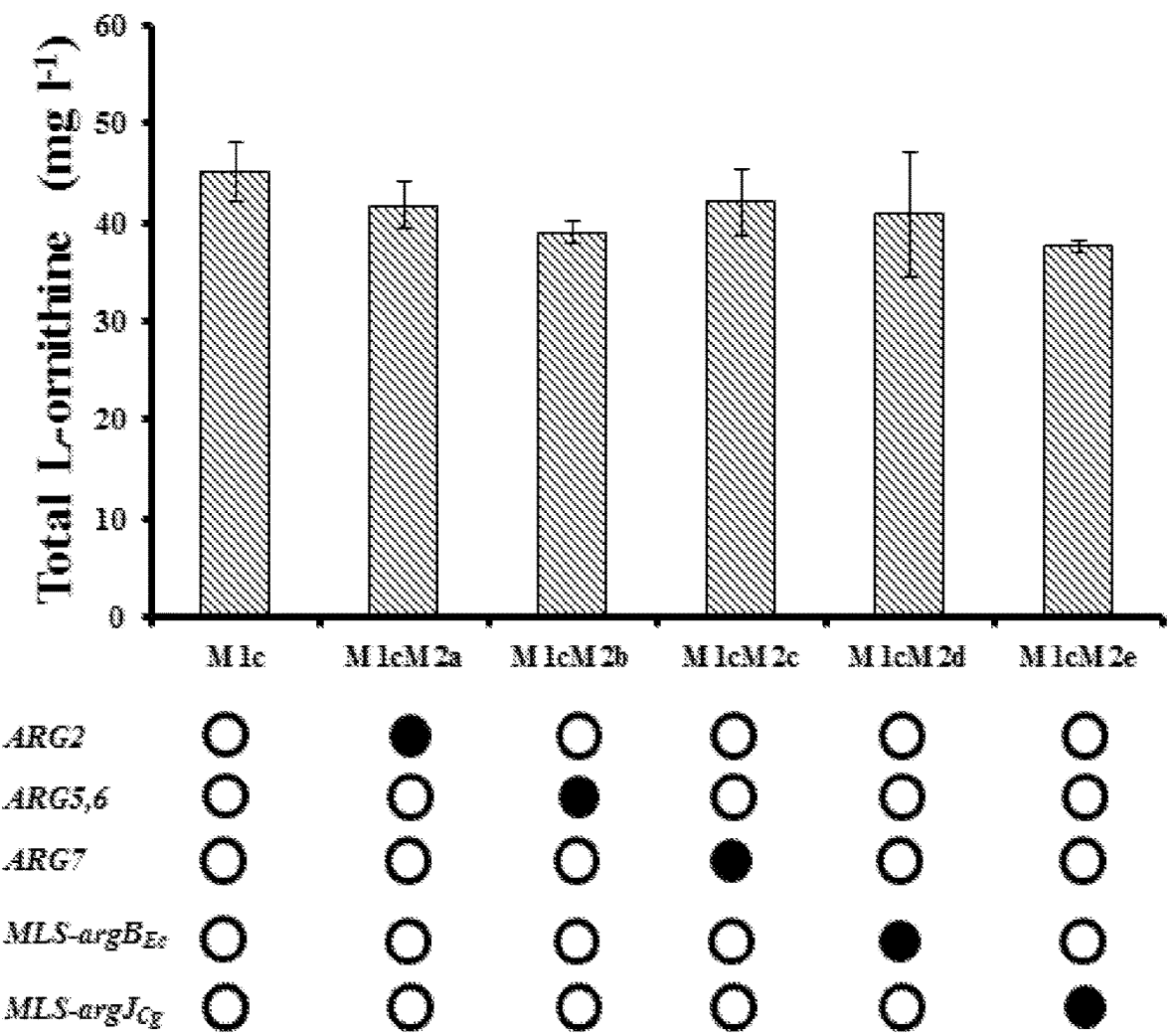
FIG. 9: The single overexpression of related genes in the L-ornithine 'acetylated derivatives cycle' showed no substantial effect to increase the L-ornithine titers. Black filled circle indicates the molecular implementation is included in the strain under test. All the strains were cultivated for 72 h in definite Delft medium. All data are presented as the mean±s.d. (n≥3).

We also investigated whether overexpression of the transcription factor Gcn4p could improve L-ornithine production by up-regulation of corresponding genes such as above mentioned ARG5, 6, ARG7 and ARG8 in L-ornithine synthetic pathway. Thus, we used different-strength promoters to fine-tune expression of a truncated version of GCN4 (tGCN4), in which residues 99-106 were truncated to circumvent the rapid degradation through the ubiquitin pathway. No obvious difference was observed in the L-ornithine titers of most of these constructs, although overexpression of GCN4 using the GPD1 promoter did result in a 16% increase in ornithine titers after 24 h of cultivation (FIG. 8).

Distinguished from L-ornithine synthesis in bacteria, L-ornithine is first synthesised in mitochondria and then exported by Ort1p to the cytosol for L-arginine biosynthesis in yeast and hence we assessed whether increasing the expression level of ORT1 could further boost the L-ornithine titers. First, the KanMX gene was removed from strain ORN-E(KanMX) by introduction of Cre-recombinase-mediated recombination between the two flanking loxP sites using plasmid pSH47 as described previously (Guldener et al., 1996), followed by removal of pSH47 by plating of the strain on 5-FOA. The ORT1 (SEQ ID NO: 10) gene was then amplified from the genome of S. cerevisiae CEN.PK113-5D strain and integrated into the genome, resulting in strain ORN-F. This strain was co-transformed with pYX212 and GO2, resulting in strain M1cM2h. This increased the L-ornithine titers to 115 mg $l^{-1}$, representing a 44% increase as compared to the control strain (M1cM2g)(FIG. 2d).

Figure 10:
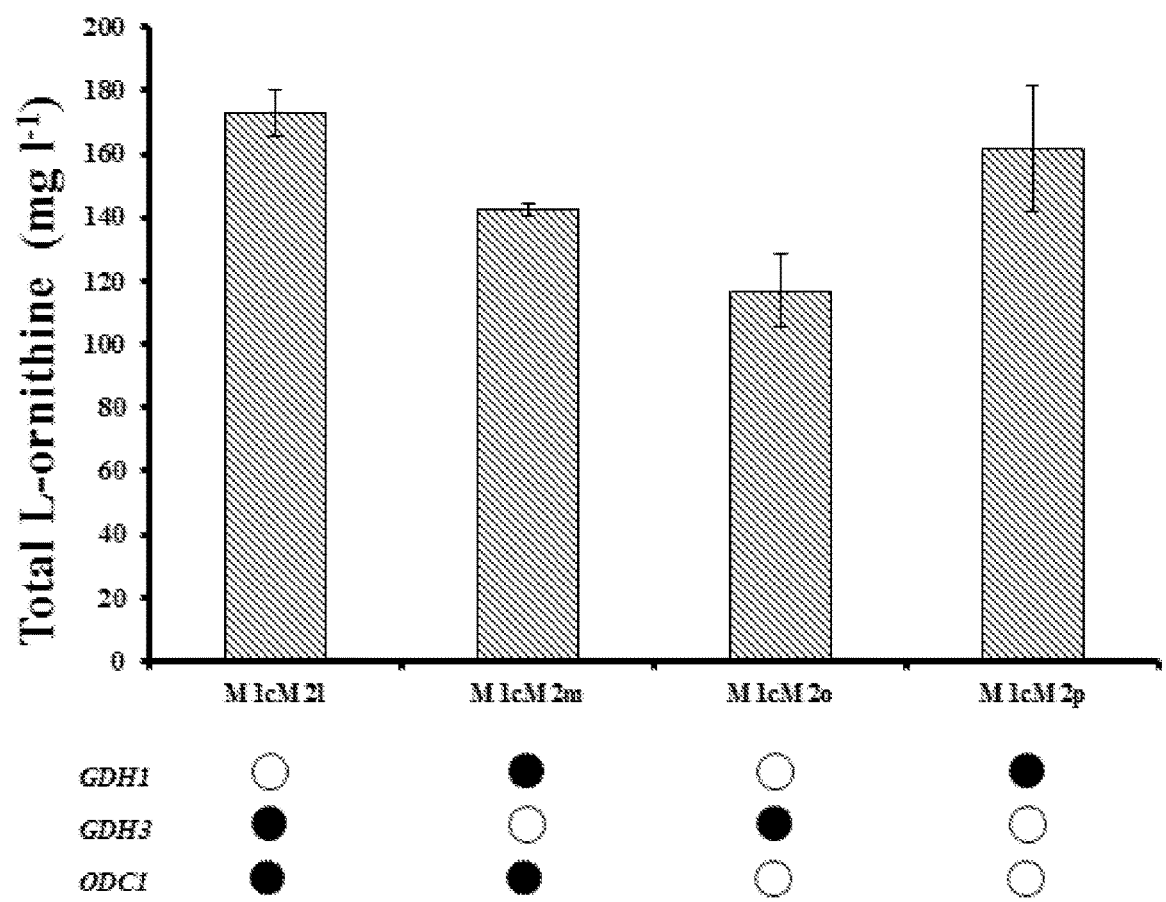
FIG. 10: The effect of ODC1 overexpression of L-ornithine titers in both GDH1 and GDH3 overexpression strain. All the strains were cultivated for 72 h in definite Delft medium. All data are presented as the mean±s.d. (n≥3).

We then engineered L-glutamate biosynthesis and its intracellular trafficking for precursor supply. We speculated that improving the internal L-glutamate trafficking step could increase the glutamate flux to further increase L-ornithine synthesis. Thus, the glutamate uniporter/aspartate-glutamate exchanger encoding gene AGC1 (SEQ ID NO: 11) was overexpressed in strain M1cM2h as described above, and L-ornithine titers in resulting strain M1cM2k increased to 149 mg $l^{-1}$, which was a 30% increase as compared to strain M1cM2h (115 mg $l^{-1}$) (FIG. 2d). Once again, the internal trafficking steps were proved to be rate limiting in metabolic pathways and overexpressing related transporters could be efficient to boost pathway flux to chemicals of interest. Beside the glutamate transportation, α-ketoglutamate transport from mitochondria to cytosol for glutamate synthesis was also enhanced by overexpressing the mitochondrial α-ketoglutamate exporter Odc1p (strain M1cM2o). However, we did not observe any substantial improvement in L-ornithine titers (FIG. 10). This result suggested that either the Odd p could not efficiently export α-ketoglutamate or that the synthesis of α-ketoglutamate could be rate limiting.

After resolving the L-glutamate transportation, the L-glutamate biosynthesis might become limiting for L-ornithine overproduction. There are three pathways that contribute to L-glutamate synthesis in S. cerevesiae. Two pathways are mediated by two isoforms of glutamate dehydrogenase, encoded by GDH1 (EC:1.4.1.4; SEQ ID NO: 6) and GDH3 (EC:1.4.1.4; SEQ ID NO: 7), while the third one catalyzed by combined activities of glutamine synthetase (encoded by GLN1; EC:6.3.1.2; SEQ ID NO: 8) and glutamate synthase (encoded by GLT1; EC 1.4.1.14; SEQ ID NO: 9). We then overexpressed the three pathways separately in strain M1cM2k respectively, resulting strain in M1cM2l (GDH1), M1cM2m (GDH3) and M1cM2n (GLN1 and GLT1). Strain M1cM2l (overexpressing GDH1) displayed a further 16% increase in ornithine production, when compared to strain M1cM2k, and the final L-ornithine titer reached 173 mg $l^{-1}$ (FIG. 2d). However, we could not see any further improvement when either GDH3 (strain M1cM2m) or GLN1 and GLT1 (strain M1cM2n) were expressed. These results indicated that Gdh1p is more efficient for synthesis of L-glutamate than Gdh3p and even the GS-GOGAT system.

Figure 11:
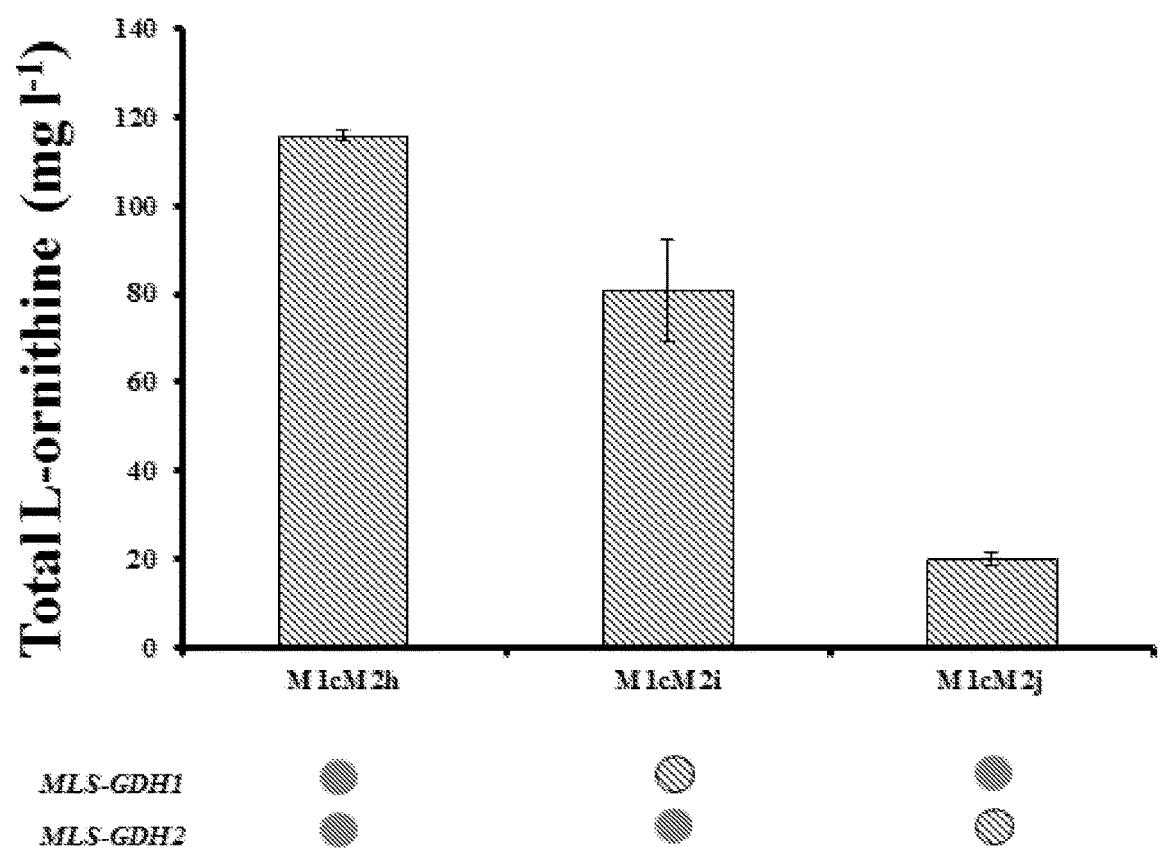
FIG. 11: The mitochondria targeting of GDH1 and GDH2 gave substantial decrease to L-ornithine titers. All the strains were cultivated for 72 h in definite Delft medium. All data are presented as the mean±s.d. (n≥3).

The separated compartmentalization of metabolites should hinder the substrate channeling for consecutive enzyme catalysis. In our case, α-ketoglutarate (mitochondria), L-glutamate (cytoplasm) and L-ornithine (mitochondria) are synthesized in different organelles. Thus, re-localization of these steps into same organelle might be helpful for L-ornithine production. We first introduced the single cytosolic step of L-glutamate biosynthesis into mitochondria by re-localizing the most efficient glutamate dehydrogenase Gdh1p into mitochondria. Considering Gdh1p is NADPH dependent and mitochondria is not rich in NADPH, we also set out to target and overexpress Gdh2p (EC 1.4.1.2) which is NADH dependent, into the mitochondria. Though the reaction catalyzed by Gdh2p favours L-glutamate degradation, but not synthesis in S. cerevesiae, the high level of α-ketoglutarate and NADH in mitochondria might reverse the reaction towards L-glutamate synthesis from α-ketoglutarate. Contrary to expectations, mitochondrial re-localization of Gdh1p (strain M1cM2i) and Gdh2p (M1cM2j) decreased the L-ornithine titers significantly (FIG. 11). The lack of increase of L-ornithine production by mitochondrial Gdh2p targeting might be attributed to its role in L-glutamate degradation which reduced the availability of the precursor for L-ornithine synthesis, while the decrease of L-ornithine production in mitochondrial Gdh1p targeting might be caused by the absence of functional targeting, which even intervene in mitochondrial function.

Figure 12:
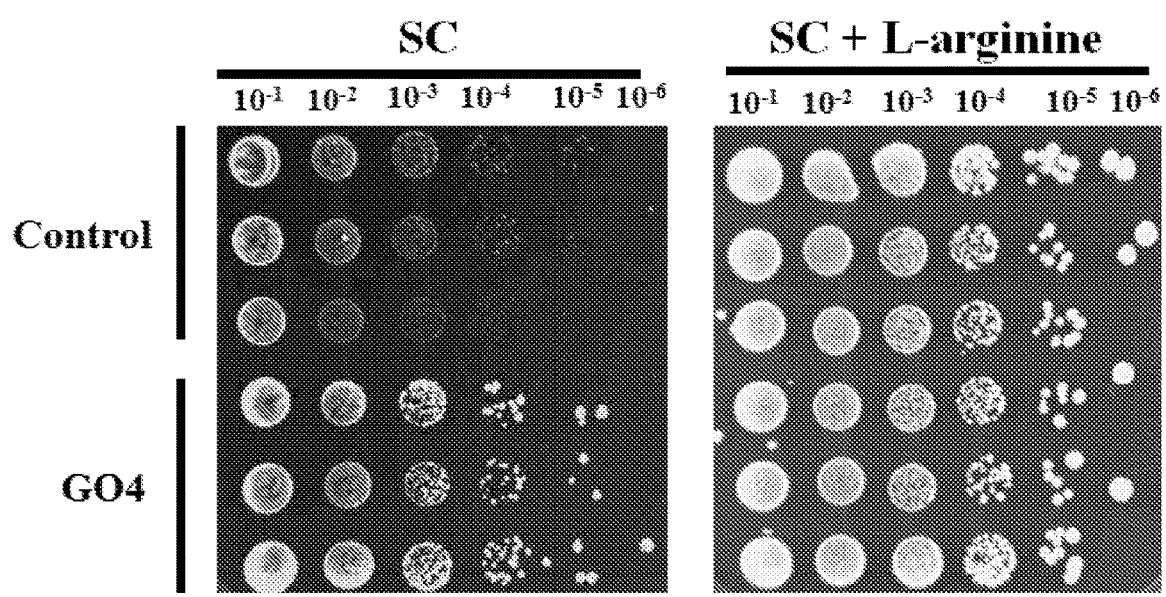
FIG. 12: The cytosolic L-ornithine synthesis pathway was functional verified by complementary test. While the control strain could not grow in the medium without L-arginine, the strain harboring the cytosolic pathway restored the ability to grow on L-arginine negative medium. Control represents Strain B0166A (p423GPD) and GO4 represents strain B0166A (ORT1). The overnight cultured cells were diluted to OD600 of 1, and 5 μl aliquots of dilutions from $10^{-1}$ to $10^{-6}$ were spotted on the corresponding plates.

We then alternatively re-localized L-ornithine synthetic pathway to cytosol, where the precursor L-glutamate is synthesized. We introduced a chimeric heterologous cytosollic L-ornithine synthetic pathway in strain M1cM2q, where the first two enzymes encoding genes $argA_{Ec}$ (SEQ ID NO: 23) and $argB_{Ec}$ (SEQ ID NO: 24) were from E. coli and other three enzymes encoding genes $argJ_{Cg}$ (SEQ ID NO: 27), $argC_{Cg}$ (SEQ ID NO: 25) and $argD_{Cg}$ SEQ ID NO: 26) were cloned from C. glutamicum. The successful complementation of L-arginine auxotrophic S. cerevisiae strain with ORT1 disruption (FIG. 12), demonstrated that the cytosolic pathway was functional to provide the precursor L-ornithine for L-arginine biosynthesis. We also observed that M1cM2q gave an 11% increase of L-ornithine, as compared to strain M1cM2l to 192 mg $l^{-1}$ in shake flask fermentation (FIG. 2d). These results demonstrated re-localization of the complete pathway into the cytosol was helpful for L-ornithine production.

Example 4

Figure 3A:
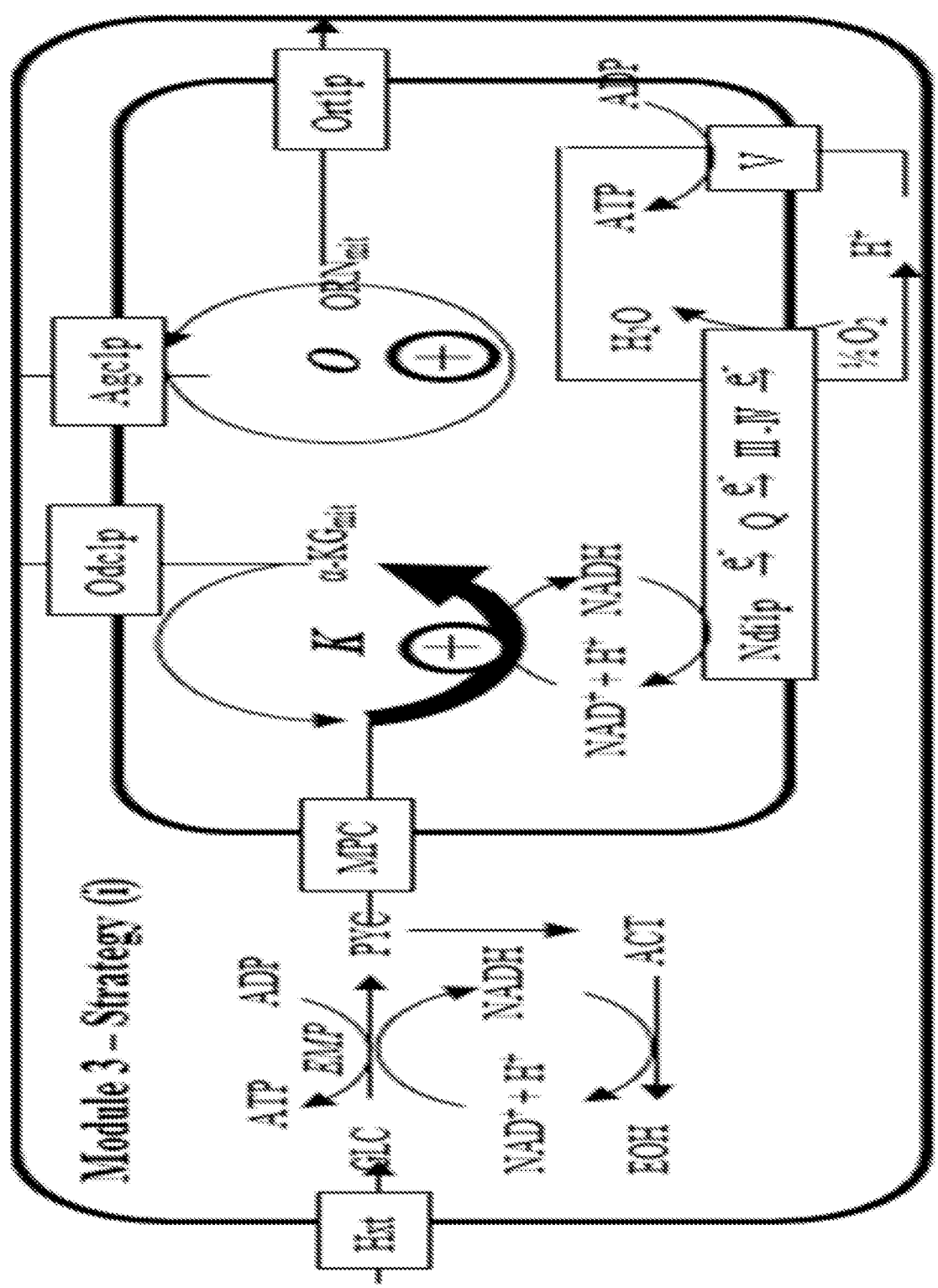
FIG. 3: L-ornithine production improved through strategies to reduce the 'Crabtree effect'. Different strategies to reduce the 'Crabtree effect' on the purpose of improve the carbon channeling from carbon substrate L-glucose to product L-ornithine were proposed. Abbreviation: K, citric acid cycle; O, L-ornithine 'acetylated derivatives cycle'; EMP, glycolysis pathway; PYC, pyruvate; EOH, ethanol; ACT, aldehyde; GLC, glucose; α-KG, α-ketoglutarate; MPC, mitochondrial pyruvate carrier; Odc1p, proposed mitochondria α-ketoglutarate transporter protein; Ort1p, mitochondria L-ornithine transporter; Agc1p, mitochondria L-glutamate transporter; MTH1-ΔT, truncated version of MTH1, AOX, NADH alternative oxidase; Q, ubiquinone; Ndi1p, NADH:ubiquinone oxidoreductase. Respiratory chain (complexes III-IV) is shown as a rectangle, and ATP synthase (complex V) as a square. (a) Strategy (i), directly overexpresses the TCA cycle enzymes including the mutated vision of Pda1p which was suggested to improve the TCA cycle flux. The circled + and − symbols denote the reactions/pathways that increased oxidative TCA cycle activity is expected to accelerate or slow down. (b) Strategy (ii), overexpress the NADH alternative oxidase from H. anomala (HaAOX1) to increase the capacity of the respiration chain which was suggested could reduce the 'Crabtree effect'. The circled + and − symbols denote the reactions/pathways that overexpression of AOX and Ndi1p is expected to accelerate or slow down. (c) Strategy (iii), control the glucose uptake rates by overexpression the truncated Mth1p from which the dephosphorylating site was removed. The circled + and − symbols denote the reactions/pathways that overexpression of MTH1-ΔT is expected to accelerate or slow down. (d) Strains with variants pathways in Module 3 led to increase production of L-ornithine. All the strains were cultivated for 72 h in definite Delft medium. All data are presented as the mean±s.d. (n≥3) (e) Physiological characterization of strain harboring truncated MTH1-ΔT and the control. $\mu_{max}$ ($h^{-1}$), $r_{EOH}$ [g ethanol (g DCW)$^{-1}$h$^{-1}$] and $r_{glu}$ [g glucose (g DCW)$^{-1}$h$^{-1}$] are shown. All values were calculated in batch culture on glucose during exponential growth phase, identified by the linear relationship between the natural logarithm of culture time and biomass. All data are presented as the mean±s.d. (n≥3). (f) Physiological characterization of strain harboring truncated MTH1-ΔT and the control. $Y_{X/S}$ [(g DCW) (g glucose)$^{-1}$], $Y_{ORN/S}$ [mg L-ornithine (g glucose)$^{-1}$] and $Y_{EOH/S}$ [g ethanol (g glucose)$^{-1}$] are shown. All values were calculated in batch culture on glucose during exponential growth phase, identified by the linear relationship between the natural logarithm of culture time and biomass. All data are presented as the mean±s.d. (n≥3).
Figure 3B:
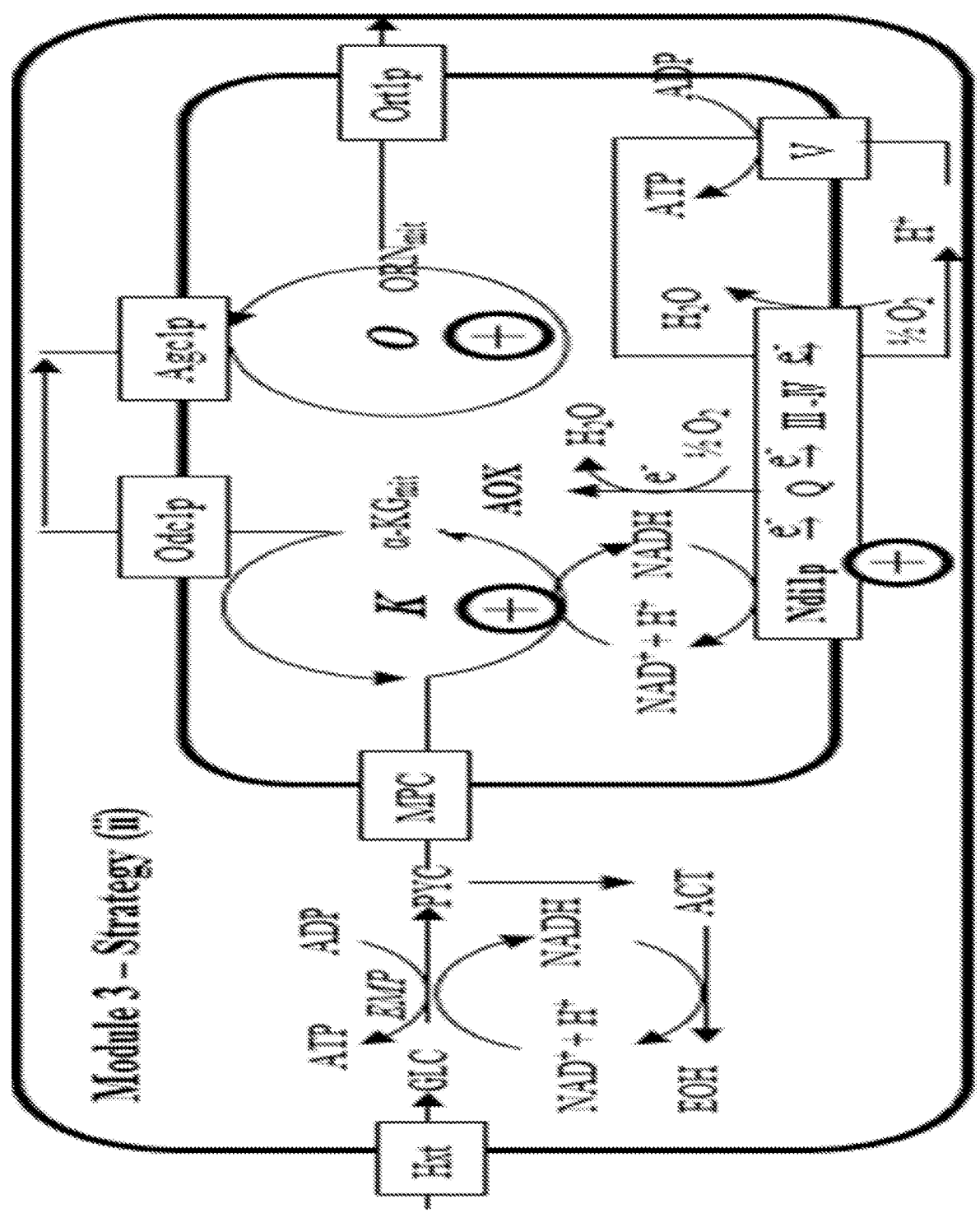
Figure 3C:
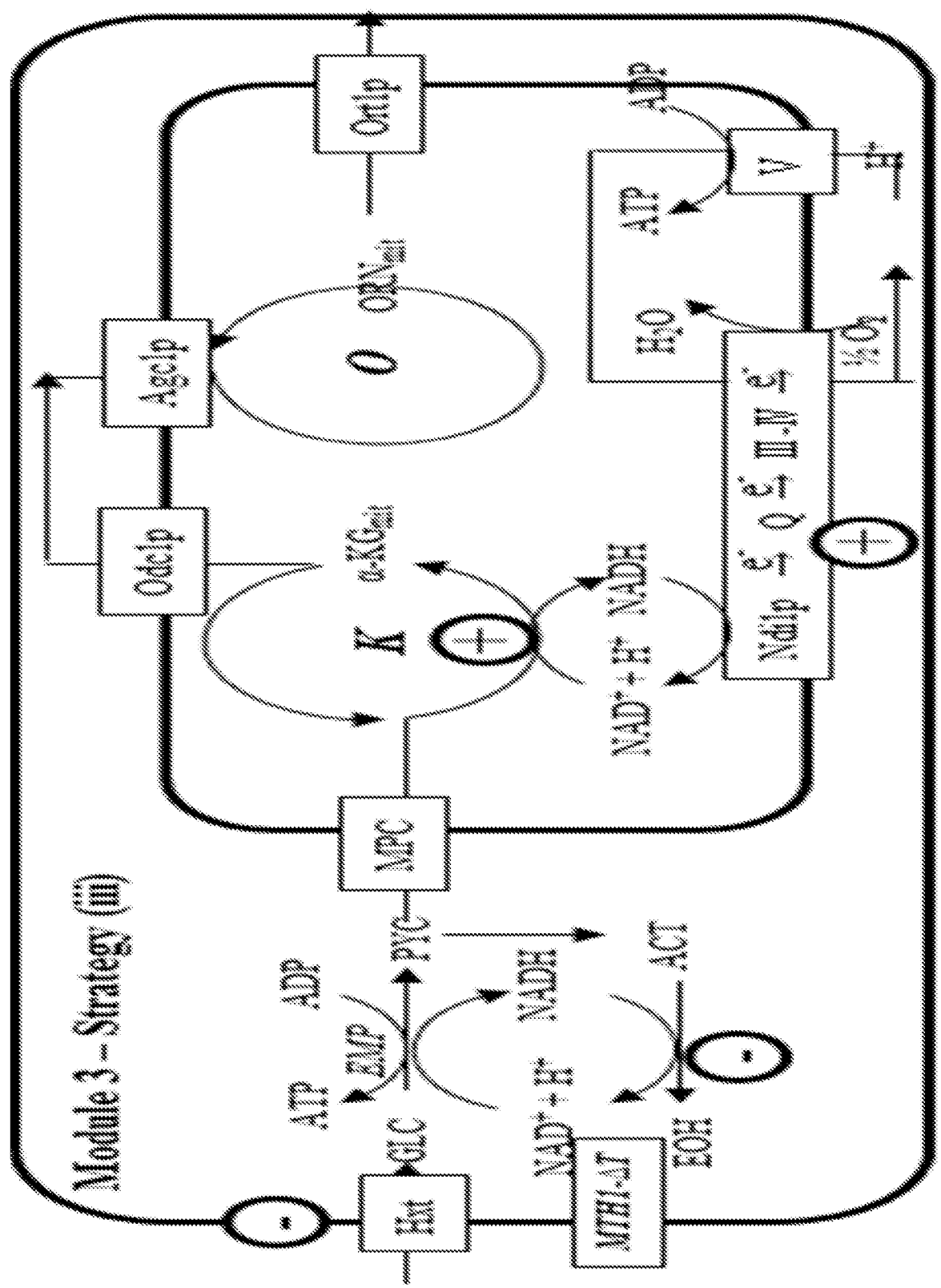

'Crabtree negative' S. cerevisiae construction enables efficient carbon channeling to L-ornithine After efficiently channeling α-ketoglutarate toward L-ornithine, we set out to enhance α-ketoglutarate supply pathway by optimizing Module 3. However, the optimization of this part will be more difficult in S. cerevisiae due to the notable 'Crabtree effect', i.e. the major carbon flux is channeled to ethanol via aerobic-fermentation when S. cerevisiae is growing exponentially on glucose aerobically. This 'Crabtree effect' actually compromised the carbon flux to TCA cycle providing α-ketoglutarate during L-ornithine biosynthesis (FIG. 3a).

Previous studies showed that the TCA cycle flux was to some extent controlled by phosphorylation of pyruvate dehydrogenase and that one mutation in the pyruvate dehydrogenase complex E1 α subunit Pda1p (EC1.2.4.1) can bypass the regulation (Oliveira et al. 2012). In this invention, we overexpressed both wild-type and mutated PDA1 to drive more flux to L-ornithine synthesis. In addition, we overexpressed the potential corresponding genes that catalyze steps from pyruvate to α-ketoglutarate, including one of the pyruvate carboxylase isomers encoding gene PYC2 (EC:6.4.1.1), citrate synthase encoding gene DTI (EC: 2.3.3.16), aconitase encoding gene ACO1 (EC 4.2.1.3) and isocitrate dehydrogenase encoding gene IDP1 (EC 1.1.1.42). The strain M1cM2qM3a, carrying the overexpression of PDA1, PYC2, CIT1, ACO1 and IDP1, had L-ornithine titers of 245 mg $l^{-1}$, representing a 28% increase as compared to parent strain M1cM2q (FIG. 3d), and overexpression of mutated mPDA1 based on PYC2, CIT1, ACO1, IDP1 (strain M1cM2qM3b) just had a slight further L-ornithine increase to 264 mg l$^{-1}$ (FIG. 3d) as compared to strain M1cM2qM3a. The detailed physiological investigation showed that M1cM2qM3b and M1cM2qM3a exhibited approximately 2-fold increased L-ornithine/glucose yield as compared to the parent, whereas there was no substantial difference when compared with the control in terms of biomass yield and maximum specific growth rate. The ethanol yield on glucose made no difference. These results demonstrated that the 'Crabtree effect' could not be substantially alleviated by directly overexpressing the TCA cycle enzymes, but the metabolic flux of the TCA cycle could be improved at a smaller extent.

Figure 3D:
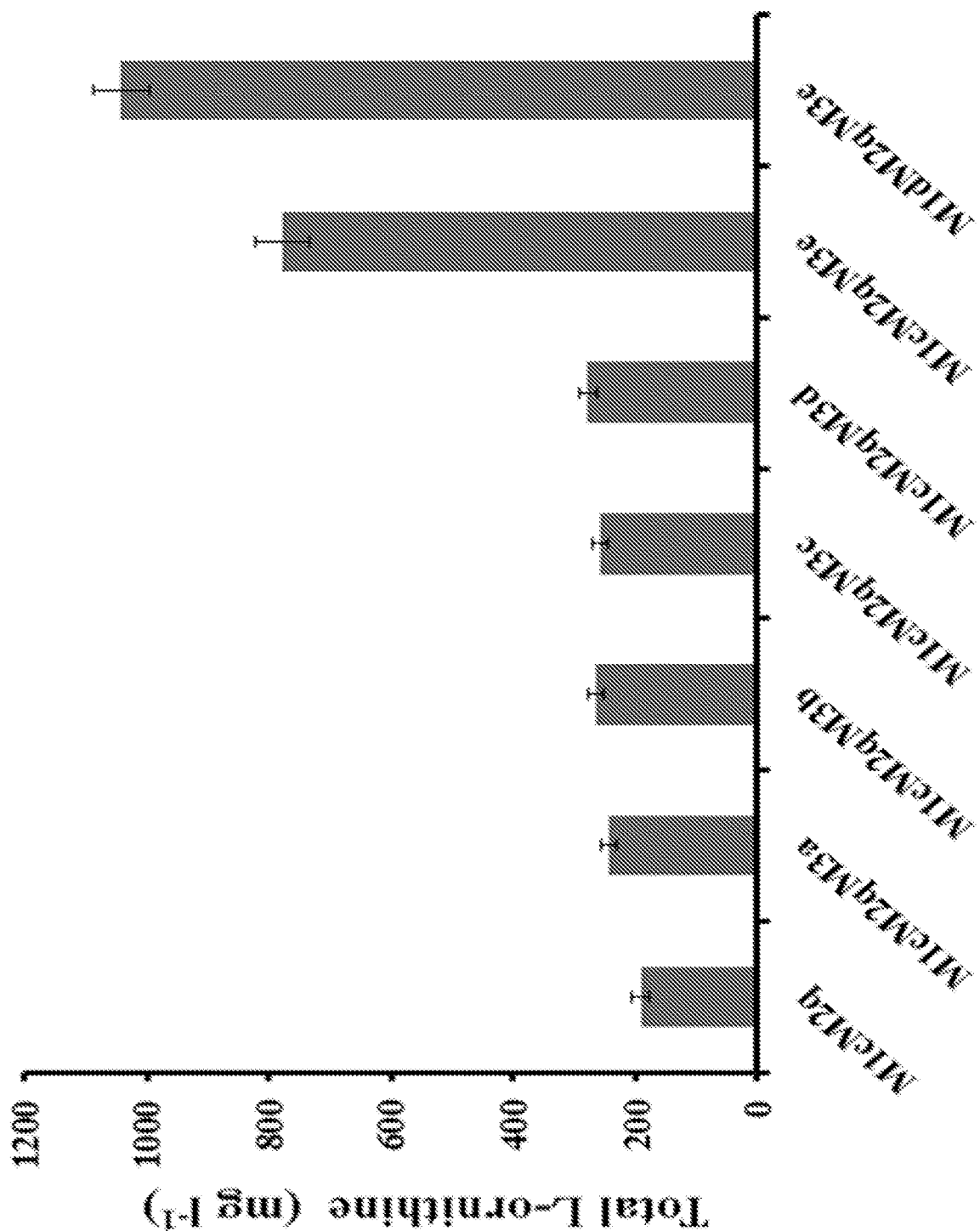

If the 'Crabtree effect' was due to the limited capacity of the respiration chain and the overexpression of NADH alternative oxidase (AOX) substantially alleviated the overflow to ethanol and if AOX overexpression up-regulated almost every step of the TCA cycle, this may be helpful for increasing production of TCA cycle derived chemicals. We overexpressed AOX from *Hansenula anomala* (HaAOX1) and also NDI1 (SEQ ID NO: 21) encoding the internal NADH dehydrogenase, which mediated the delivery of the equivalents to the respiratory chain. The overexpression of HaAOX1 (strain M1cM2qM3c) enabled the L-ornithine titers to reach 258 mg l$^{-1}$, representing a 35% increase as compared the parent strain M1cM2q (FIG. 3d). Furthermore, combined overexpression of NDI1 and HaAOX1 further increased L-ornithine production to 278 mg l$^{-1}$ (FIG. 3d). These results indicated that NADH dehydrogenation was a rate limiting step in NADH oxidation, and overexpression of alternative NADH oxidase was an efficient strategy to boost the TCA flux for the production of TCA derived amino acids. It should be emphasized that the overexpression of HaAOX1 and NDI1 (strain M1cM2qM3d) increased the L-ornithine production to the same level as boosting the TCA cycle's enzyme activity by direct overexpression of related genes (strain M1cM2qM3b) (FIG. 3d).

Figure 3E:
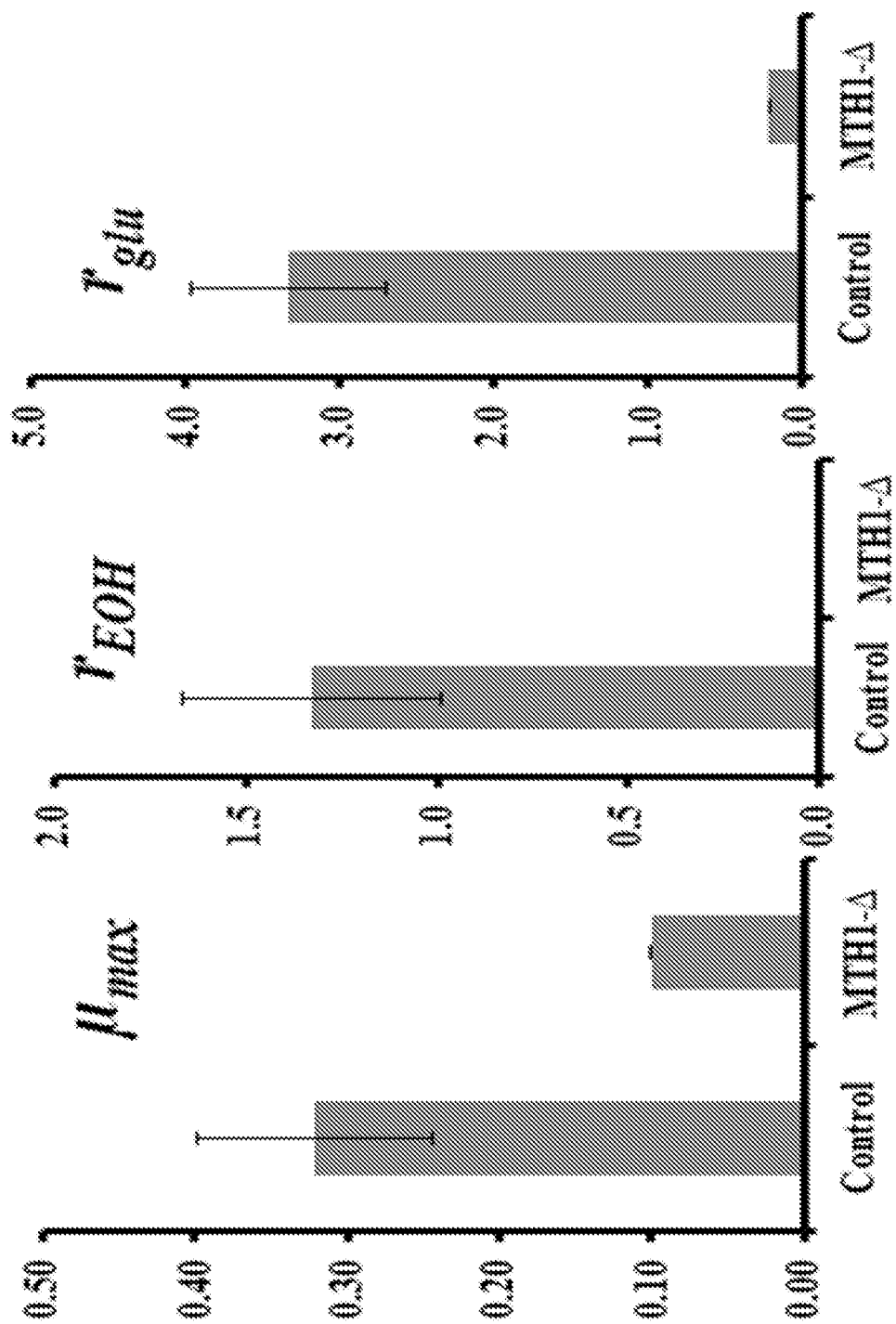
Figure 3F:
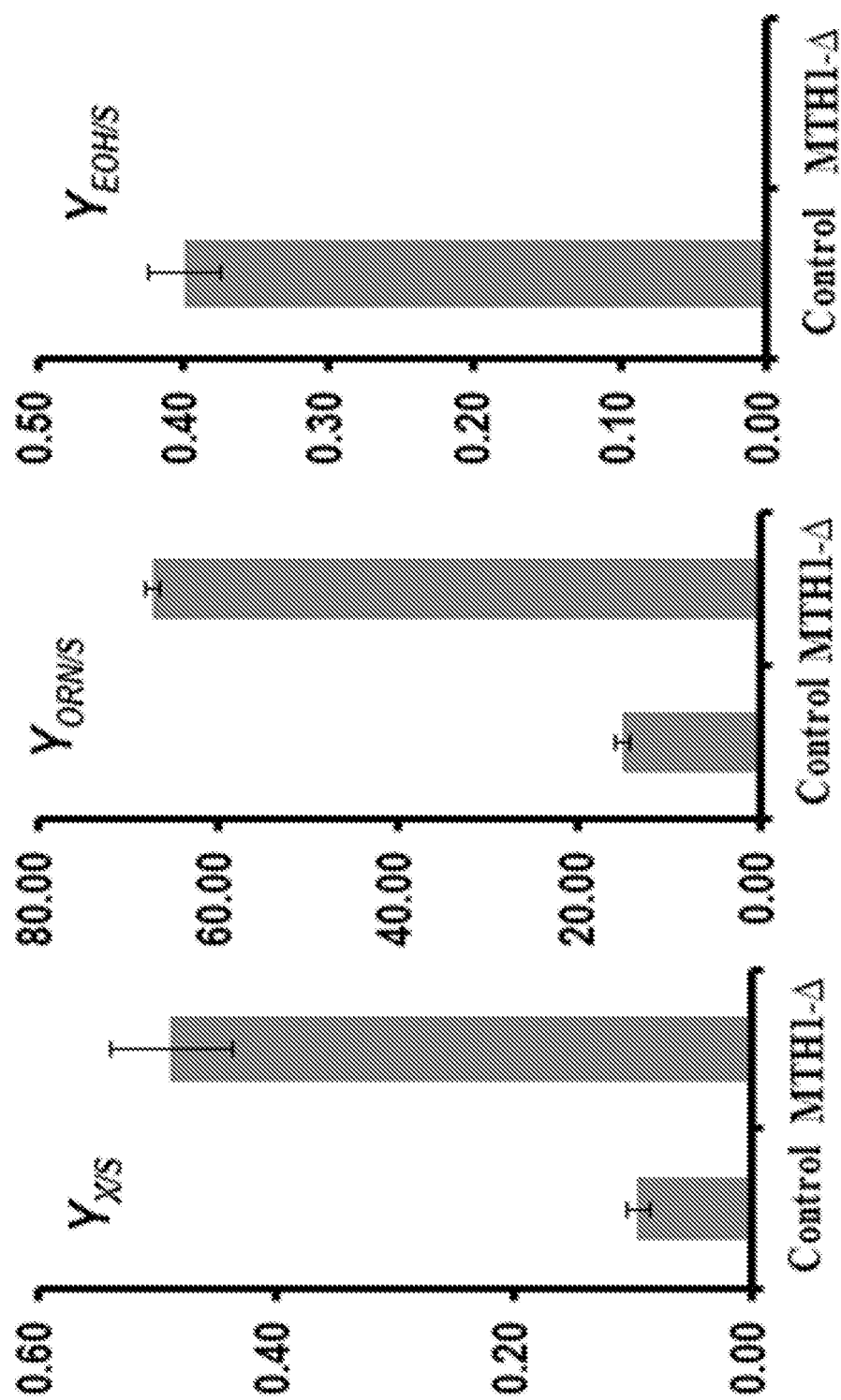

Although aforementioned strategy had to some extent positive effect on L-ornithine production, the 'Crabtree effect' needed further alleviation. Overexpression of MTH1-ΔT (strain M1cM2qM3e) increased L-ornithine titers up to 778 mg l$^{-1}$ compared to the parent strain M1cM2q (FIG. 3d). It should also be emphasized that while the MTH1-ΔT overexpression (M1dM2qM3e) strain produced no ethanol and had low glucose uptake of 0.2 g glucose (g DCW)$^{-1}$h$^{-1}$, the parent strain had ethanol production of 1.3 g ethanol (g DCW)$^{-1}$h$^{-1}$ and glucose uptake rate of 2.2 g glucose (g DCW)$^{-1}$h$^{-1}$ (FIG. 3e). These results demonstrated that alleviating the 'Crabtree effect' of *S. cerevisiae* was an efficient strategy to boost L-ornithine production by enhancing TCA cycle flux.

Figure 13:
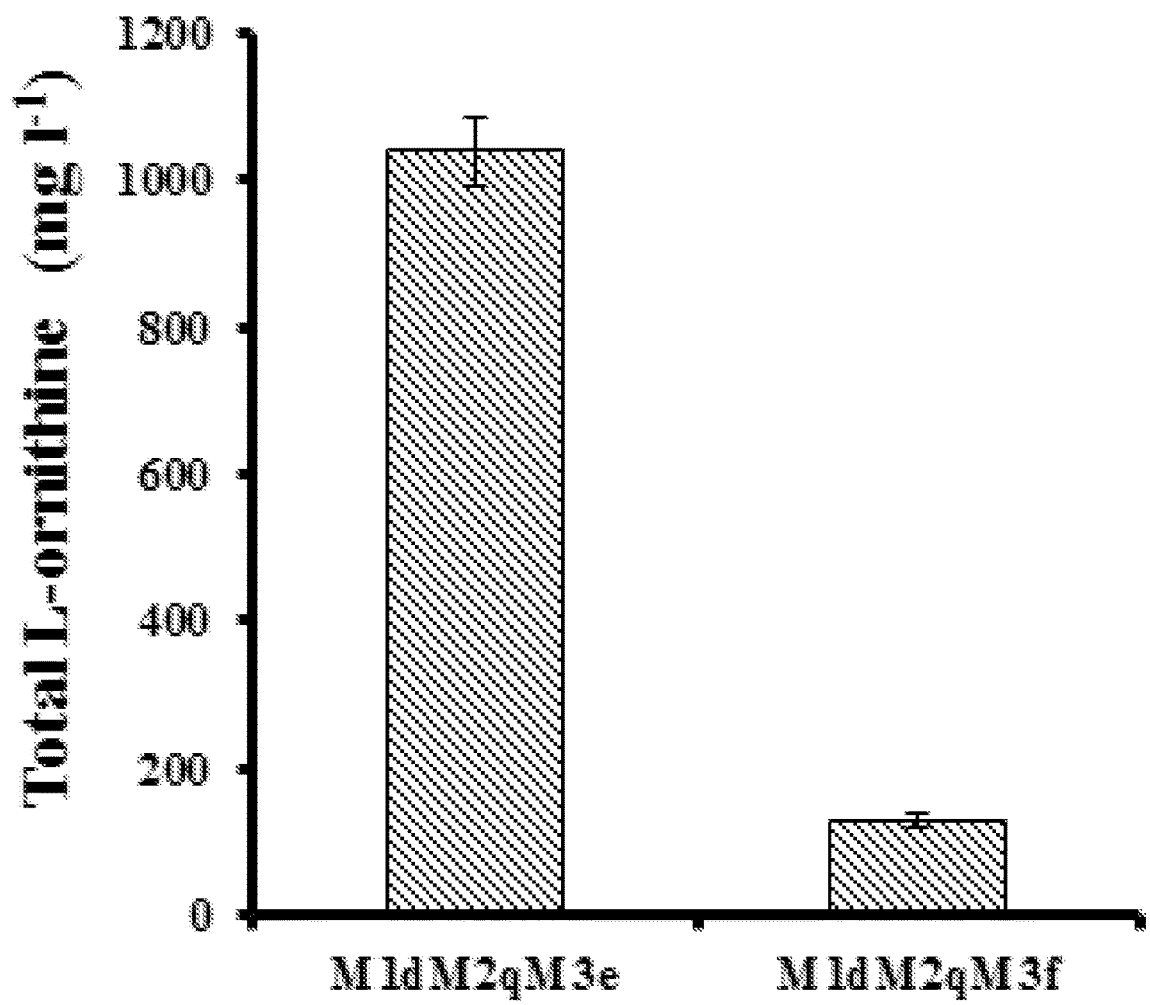
FIG. 13: The KGD2 knock-down gave L-ornithine titers decrease. All the strains were cultivated for 72 h in definite Delft medium. All data are presented as the mean±s.d. (n≥3).
Figure 14:
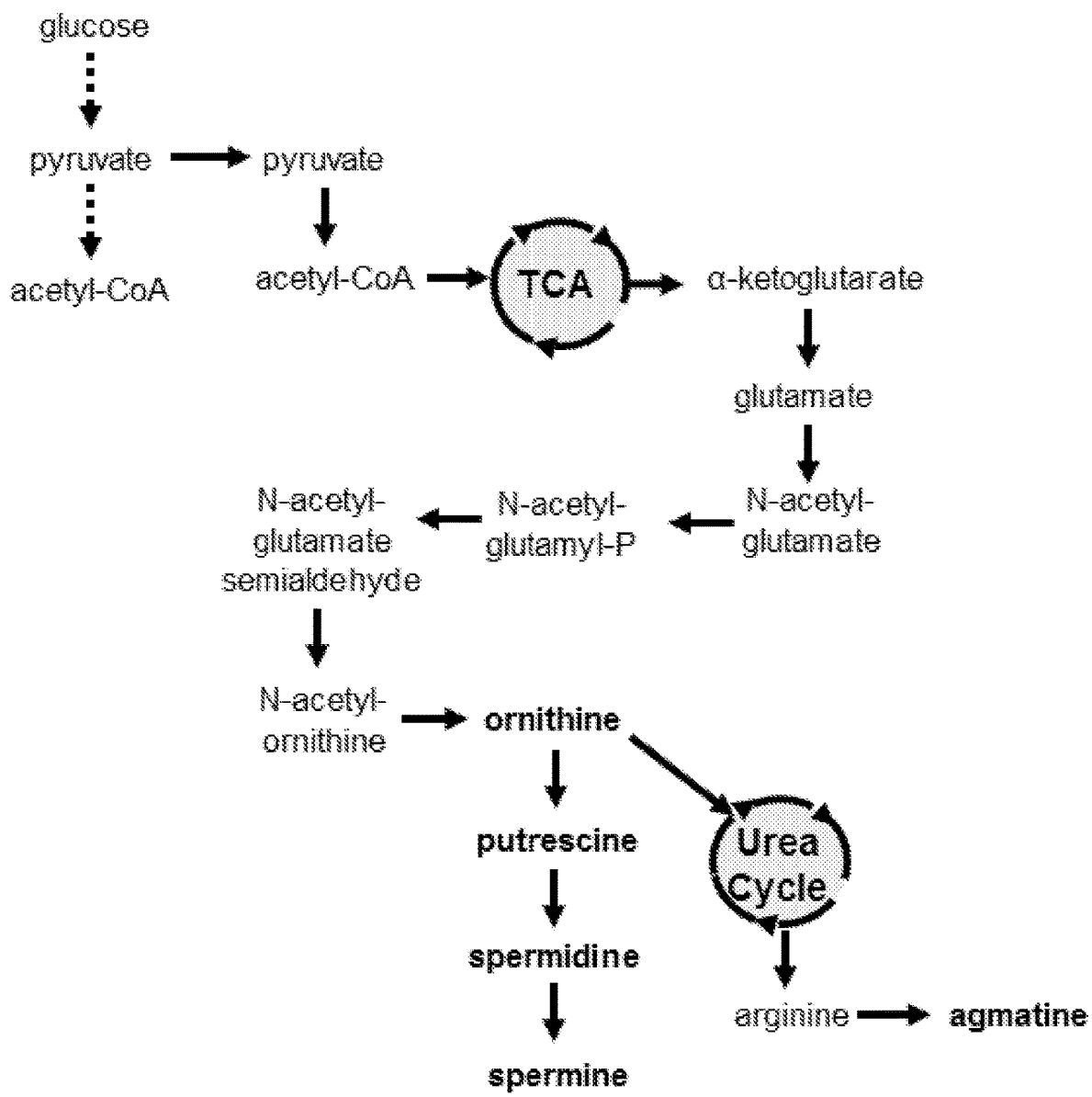
FIG. 14: Overview of pathway leading to ornithine derivatives.

We also assessed whether ODC attenuation might redirect more TCA flux to synthesis of L-glutamate, the precursor of L-ornithine. However, attenuation of KGD2, encoding one of the components of the mitochondrial α-ketoglutarate dehydrogenase complex, decreased L-ornithine titers 10-folds (FIG. 13). KGD2 down-regulation (Strain M1dM2qM3f) restored the glucose uptake of 2.2 g glucose (g DCW)$^{-1}$h$^{-1}$ and ethanol production of g ethanol (g DCW)$^{-1}$h$^{-1}$ compared to the parent strain of MTH1-ΔT overexpression.

Figure 4:
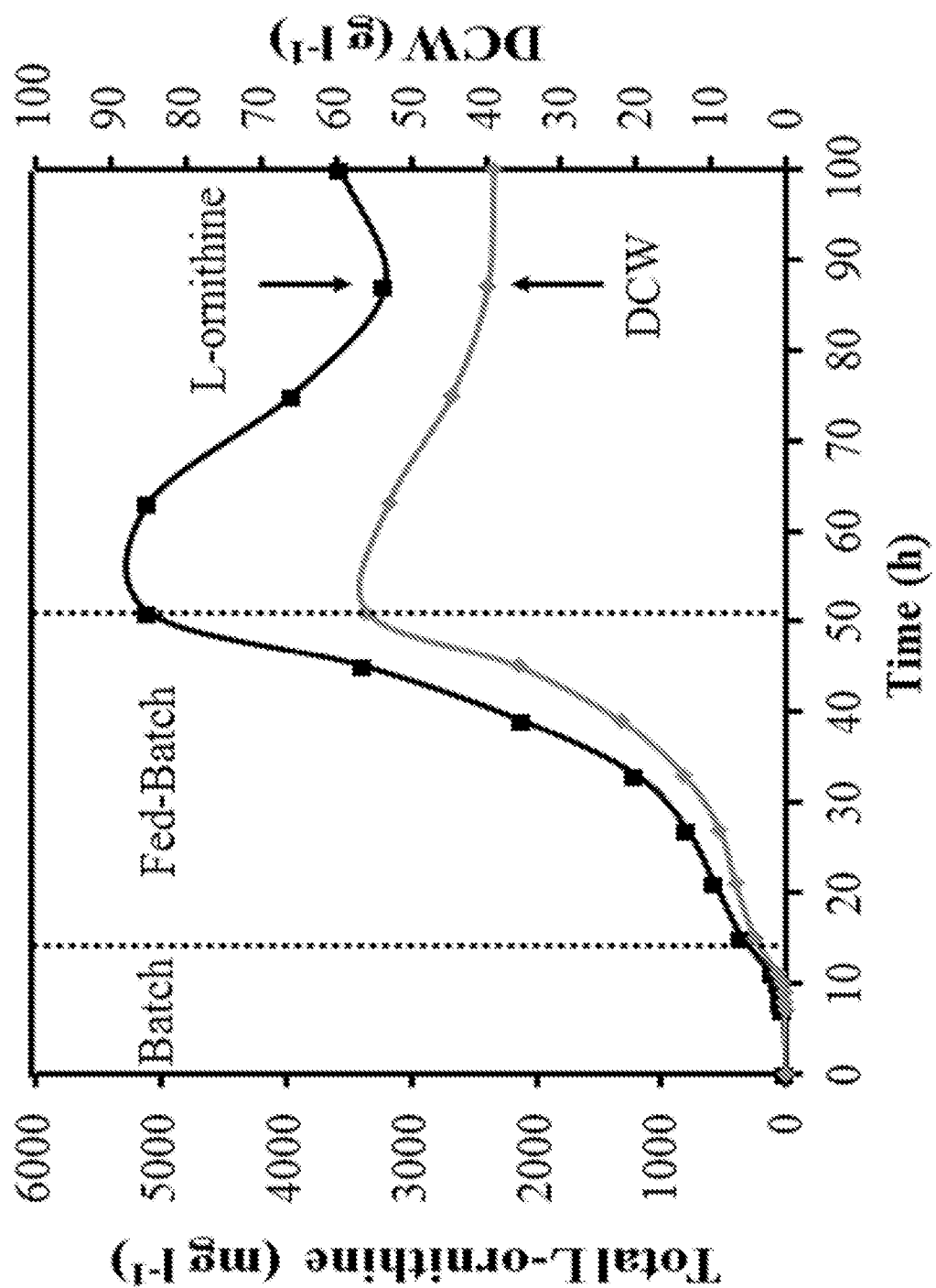
FIG. 4: Fed-batch fermentation of engineered strain in 3-l bioreactor. Time course profile of DCW (grey line) and L-ornithine (black line) of strain M1dM2qM3a were shown.
Figure 5:
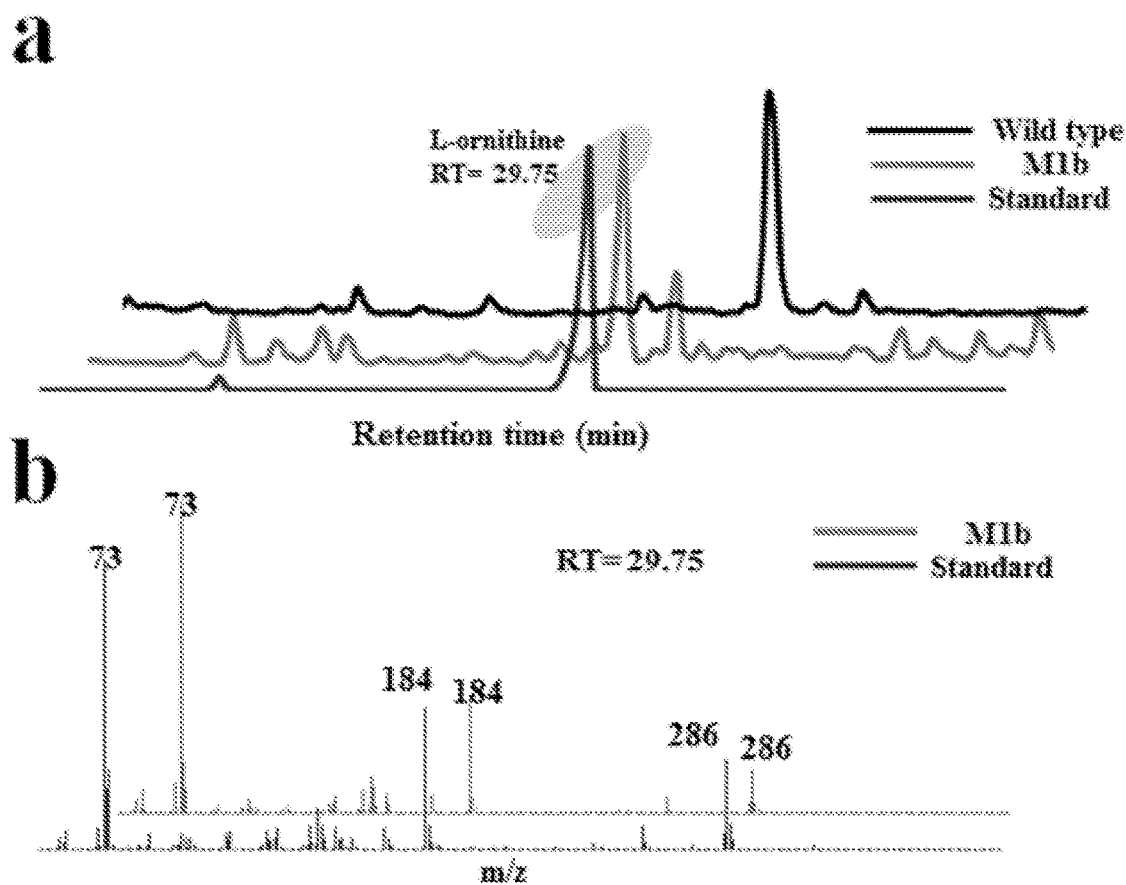
FIG. 5: Qualitative verification of L-ornithine produced by proof of concept strain with GC-MS. (a) Gas chromatogram of L-ornithine (retention time 29.75 min). (b) High resolution mass spectrometry of L-ornithine.
Figure 6:
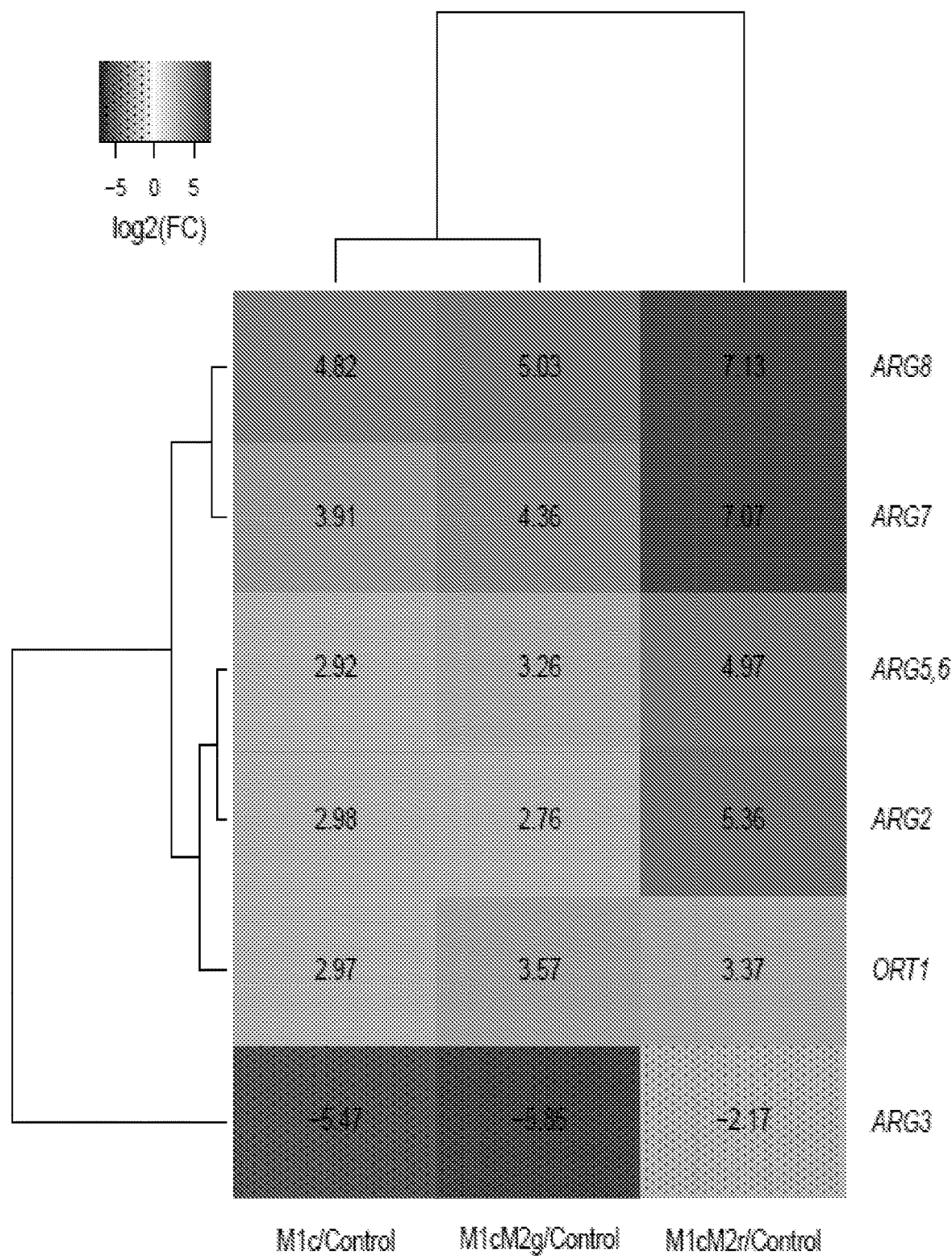
FIG. 6: RT-PCR indicated significant changes were in strains producing L-ornithine and the control strain. The comparisons are M1c vs. control, M1cM2r vs. control and M1cM2g vs. control. The grey-scale key represents log 2 [fold change], untextured grey represents up-regulation and dotted-grey represents down-regulation. The intensity of the grey colour correlates with the fold-change.
Figure 7:
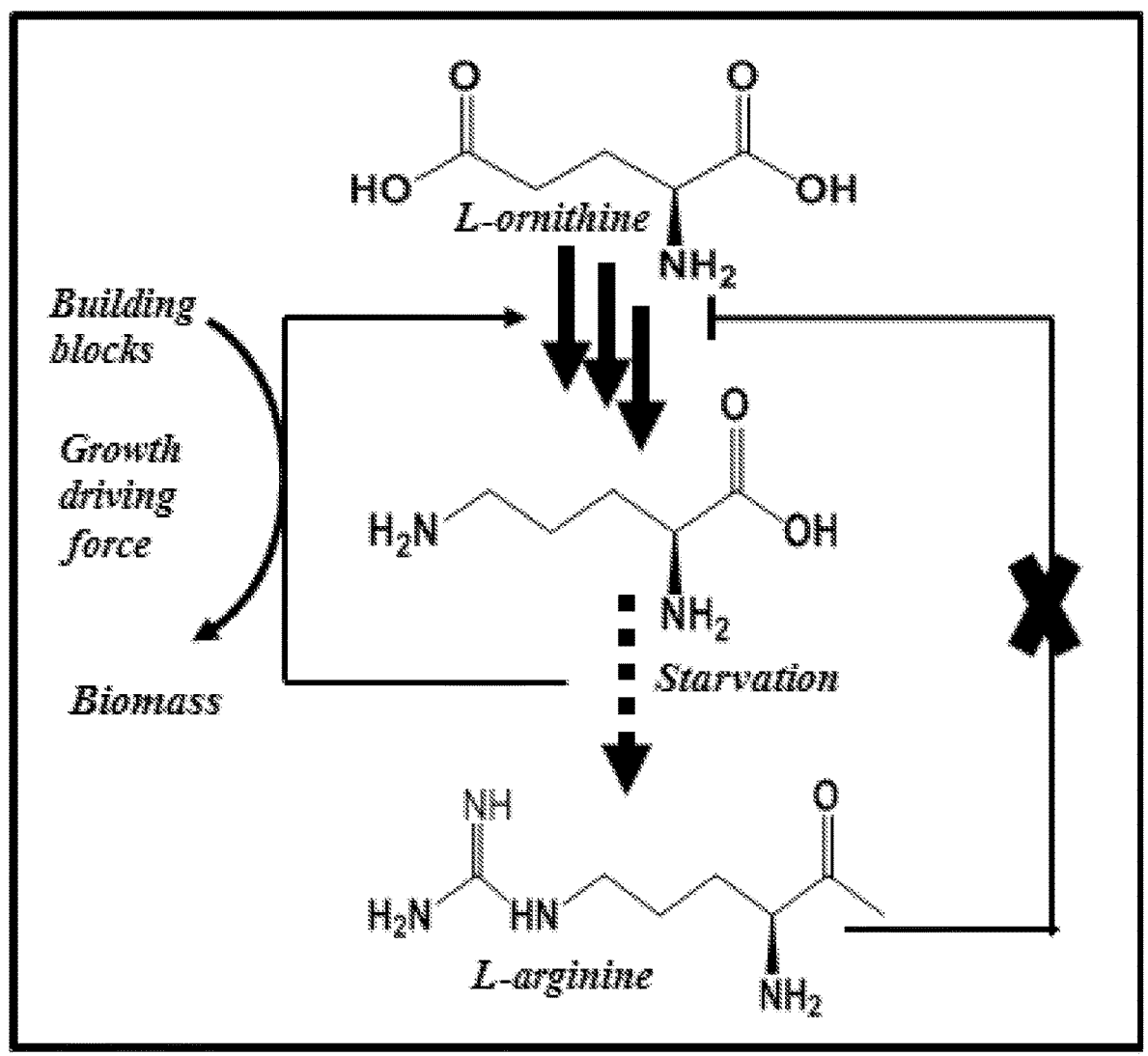
FIG. 7: Proposed underline mechanisms by which the L-ornithine 'acetylated derivatives cycle' flux was boosted when Arg3p was attenuated.

Besides the molecular manipulation, we explored the possibility of alleviating the 'Crabtree effect' by using an aerobic glucose-limited fed-batch strategy with strain M1cM2qM3a, whose upstream TCA cycle was enhanced as described above. Our engineered strain gave a final L-ornithine titer of 5.1 g l$^{-1}$, whereas the DCW was 56 g l$^{-1}$ (FIG. 4).

Example 5

'Urea Cycle' Engineering Enables Further L-Ornithine Titer Improvement

*S. cerevisiae* has the potential to operate a urea cycle: arginase (encoded by CAR1; EC:3.5.3.1; SEQ ID NO: 1)) can degrade L-arginine into urea and L-ornithine. Early study showed that in the presence of L-arginine and L-ornithine, ornithine carbamoyltransferase (OTC, Arg3p) and arginase (Car1p), both trimeric proteins, can form the so-called 'epi-arginase' mode of regulation, i.e. a one-to-one complex in which arginase remains active but OTC activity is inhibited. This regulation prevents the formation of an L-ornithine futile cycle when the biosynthesis of L-arginine is repressed and the catabolism of L-arginine activated. Our previous result showed that the strain with attenuated Arg3p still maintained ⅔ of the L-arginine intracellular concentration. It is speculated that overexpression of Car1p could enable even lower intracellular L-arginine. CAR1 overexpression (strain M1dM2qM3e) gave the final L-ornithine titers to 1041 mg l$^{-1}$, representing a further 34% increase as compared to the parent strain M1cM2qM3e and 23-fold when compared with strain M1c (FIG. 3d). Our result indicated that CAR1 overexpression pushed more flux into the L-ornithine synthesis cycle.

Example 6

Overexpression of the Putrescine Biosynthetic Pathway in *S. cerevisiae*

To increase putrescine production, the gene OAZ1, coding for the ornithine decarboxylase antizyme was deleted from strain ORN-L(KanMX) and strain CEN.PK113-11C. First, the KanMX marker from ORN-L(KanMX) was looped out by introduction of Cre-recombinase-mediated recombination between the two flanking loxP sites using plasmid pSH47 as described previously (Guldener et al., 1996), followed by removal of pSH47 by plating of the strain on 5-FOA, resulting in strain ORN-L. Next, OAZ1 was deleted from ORN-L and CEN.PK113-11C using a bipartite strategy (Erdeniz et al., 1997). Two overlapping fragments of the kanMX resistance marker cassette flanked by loxP sites were amplified via PCR from plasmid pUG6 (Giildener et al., 1996). Sequences upstream and downstream of OAZ1 were also amplified. Due to overlapping ends (introduced through the primer sequences) the OAZ1-upstream fragments could be fused to the 5' kanMX fragment and the 3' kanMX fragment to the individual OAZ1-downstream fragments by fusion PCR using the outer primers for amplification. The two overlapping PCR fragments thus generated for each gene deletion were transformed into yeast using the lithium acetate method (Gietz and Woods, 2002). This resulted in strains PUT-A(KanMX) (expressing the ornithine pathway) and WT-PUT-A (KanMX) (not-expressing the ornithine platform). Subsequent transformation of WT-PUT-A(KanMX) with p426GPD and p423GPD resulted in strain WT-PUT1. PUT-A(KanMX) was transformed with plasmids p426GPD and GO4, resulting in strain PUT-1.

In parallel, following the same procedure, we also constructed the integration cassette for SPE1 overexpression which codes for ornithine decarboxylase (EC 4.1.1.17). SPE1 was amplified from S. cerevisiae (CEN.PK113-11C) genome (SEQ ID NO: 29) and placed under the control of TEF1 promoter and PRM9t terminator (Chen et al., 2012a) using fusion PCR procedures. The cassette was integrated to OAZ1 site of ORN-L and CEN.PK113-11C, resulting in strains PUT-B(KanMX) and WT-PUT-B(KanMX), respectively. WT-PUT-B(KanMX) was then transformed with plasmids p426GPD and p423GPD, resulting in strain WT-PUT2. PUT-B(KanMX) was transformed with plasmids p426GPD and GO4, resulting in strain PUT-2.

To further increase production of putrescine, the export of these polyamines can be increased by overexpressing genes associated with polyamine export or deleting genes associated with polyamine uptake. To increase putrescine production by S. cerevisiae, the gene TPO1 (SEQ ID NO: 32) was amplified from the genome of S. cerevisiae (CEN.PK113-11C) using PCR. This gene was then cloned into p412GPD under the control of the TDH3 promoter using standard cloning procedures, resulting in plasmid p412GPD-TPO1. This plasmid was transformed into strain WT-PUT-B (KanMX) together with plasmid p423GPD, resulting in strains WT-PUT3. p412GPD-TPO1 was also transformed into strain PUT-B(KanMX) together with the vector GO4, resulting in strain PUT3.

The resulting strains were cultivated in minimal media. In order to quantify polyamine production, samples were treated as follows: cultivation sample was prepared by taking 1 ml of liquid culture. Cells were spun down by centrifugation. The supernatant was directly used for derivatization. Cells were subject to Hot Water (HW) Extraction. This procedure was adapted from (Canelas et al. 2009). Tubes containing 1 ml of demineralized water were preheated in a water bath at 95-100° C. for 10 min. Then, the hot water was quickly poured over the cell pellet; the mixture was immediately vortexed, and the sample was placed in the water bath. After 30 min, each tube was placed on ice for 5 min. After centrifugation, the supernatant was directly used for derivatization. For the accurate measurement of polyamine concentration, samples were diluted, if necessary, to give polyamine concentration within the standard curve range. For derivatization, the procedure was adapted from (Kim et al. 2015). In brief, 0.25 ml of saturated NaHCO3 solution and 0.5 ml of dansyl chloride solution (5 mg/ml in acetone) were added to 0.5 ml of sample. Then the reaction mixture was incubated at 40° C. for 1 h in the dark with occasional shaking. The reaction was stopped by adding 0.1 ml 25% ammonium hydroxide. Samples filtered through a 25 mm syringe filter (0.45 μm Nylon) can be used for HPLC detection. The following chromatographic condition are used: C18 (100 mm×4.6 mm i. d., 2.6 μm, Phenomenex Kinetex), excitation wavelength 340 nm, emission wavelength 515 nm, Sample injecting 10p1, column temperature 40° C., Detector sensitivity 7, acquisition starts at 3.4 min. The mobile phase is water and methanol with the speed of 1 mL/min. The elution program is as follows: 0-23 min 50% to 95% MeOH, 23-27 min 95% MeOH, 27-32 min 95% to 100% MeOH, 32-37 min 100% to 50% MeOH.

Figure 15:
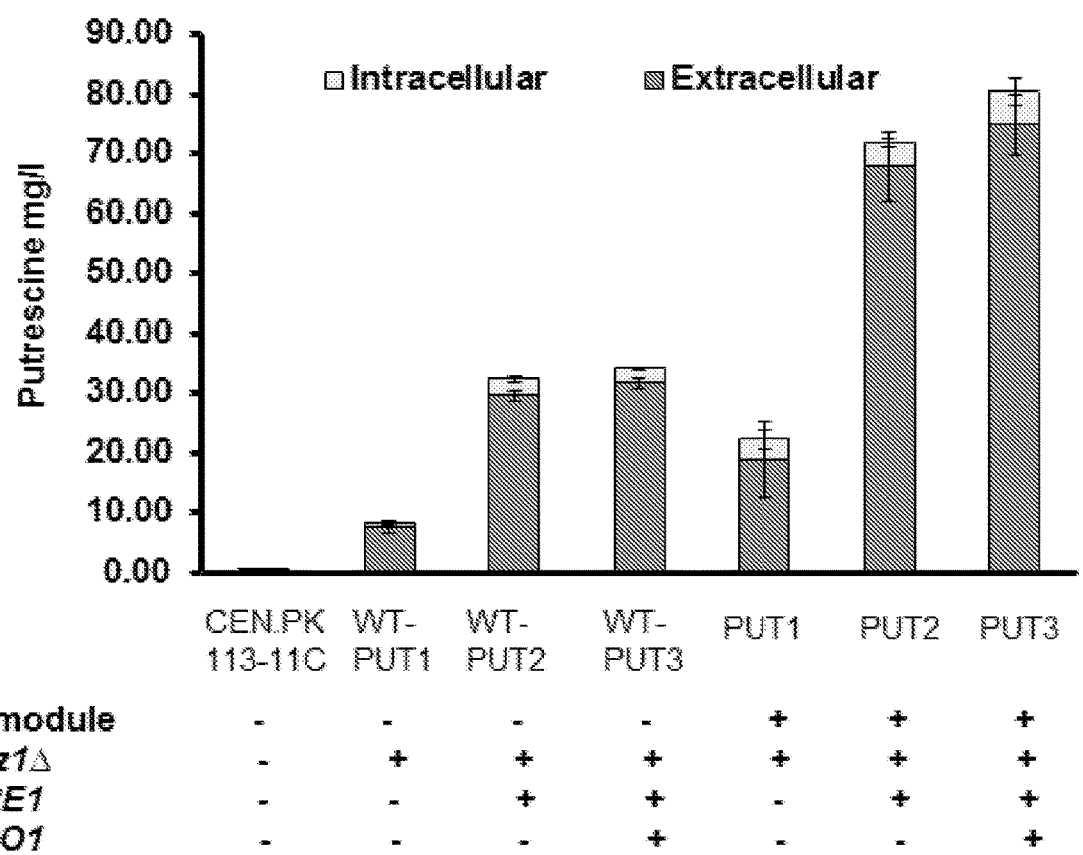
FIG. 15: Putrescine production in engineered yeast strains with or without an ornithine module. The ornithine module includes pKEX2-ARG3, Δcar2, GDH1, ORT1, AGC1 and the cytosolic ornithine synthetic pathway in the plasmid GO4. Further engineering for putrescine production includes deletion of OAZ1 and overexpression of SPE1. Both intra- and extra-cellular levels of putrescine were quantified.

Both intracellular and extracellular putrescine levels were quantified (FIG. 15). Levels of putrescine significantly increased upon deletion of OAZ1, and increased further upon introduction of SPE1 (FIG. 15). Furthermore, strains engineered for increased ornithine production (strains PUT1, PUT2 and PUT3) produced significantly more putrescine compared to strains without any ornithine pathway modifications (FIG. 15), displaying the benefits of the ornithine platform for polyamine production. In addition, a slight increase in putrescine levels was observed for strains overexpressing the transporter TPO1 (FIG. 15).

Example 7

Overexpression of the Spermidine Biosynthetic Pathway in S. cerevisiae

To increase spermidine production by S. cerevisiae, the genes SPE2 (SEQ ID NO: 30) and SPE3 (SEQ ID NO: 31), encoding S-adenosylmethionine decarboxylase (EC 4.1.1.50) and spermidine synthase (EC 2.5.1.16) (respectively), were amplified from the genome of S. cerevisiae (CEN.PK113-11C) using PCR.

Following the same procedure, we also constructed the integration cassette for SPE3 overexpression which codes for Spermidine synthase (EC 2.5.1.16). SPE3 was amplified from S. cerevisiae (CEN.PK113-11C) genome (SEQ ID NO: 31) and placed under the control of PGK1 promoter and pYX212t terminator using fusion PCR procedures. SPE1 which codes for ornithine decarboxylase (EC 4.1.1.17) together with TEF1 promoter and PRM9t terminator was also included in the same cassette. The cassette was integrated into OAZ1 site of ORN-L, resulting in strain SPD-A(KanMX). Subsequent transformation of plasmid p426GPD and GO4 resulted in strain SPD1.

In parallel, following the same procedure, we also constructed the integration cassette for SPE2 (SEQ ID NO: 30) encoding S-adenosylmethionine decarboxylase (EC 4.1.1.50). SPE2 was amplified from S. cerevisiae (CEN.PK113-11C) genome (SEQ ID NO: 30) and placed under the control of TDH3 promoter and DIT1t terminator using fusion PCR procedures. SPE1 which codes for ornithine decarboxylase (EC 4.1.1.17) together with TEF1 promoter and PRM9t terminator was also included in the same cassette. Also, SPE3 which was amplified from S. cerevisiae (CEN.PK113-11C) genome (SEQ ID NO: 31) under the control of PGK1 promoter and pYX212t terminator using fusion PCR procedures was as part of the integration cassette. The full cassette was integrated into the OAZ1 site of ORN-L, resulting in strain SPD-B(KanMX). Subsequent transformation of this strain with plasmids p426GPD and GO4 resulted in strain SPD2.

Figure 16:
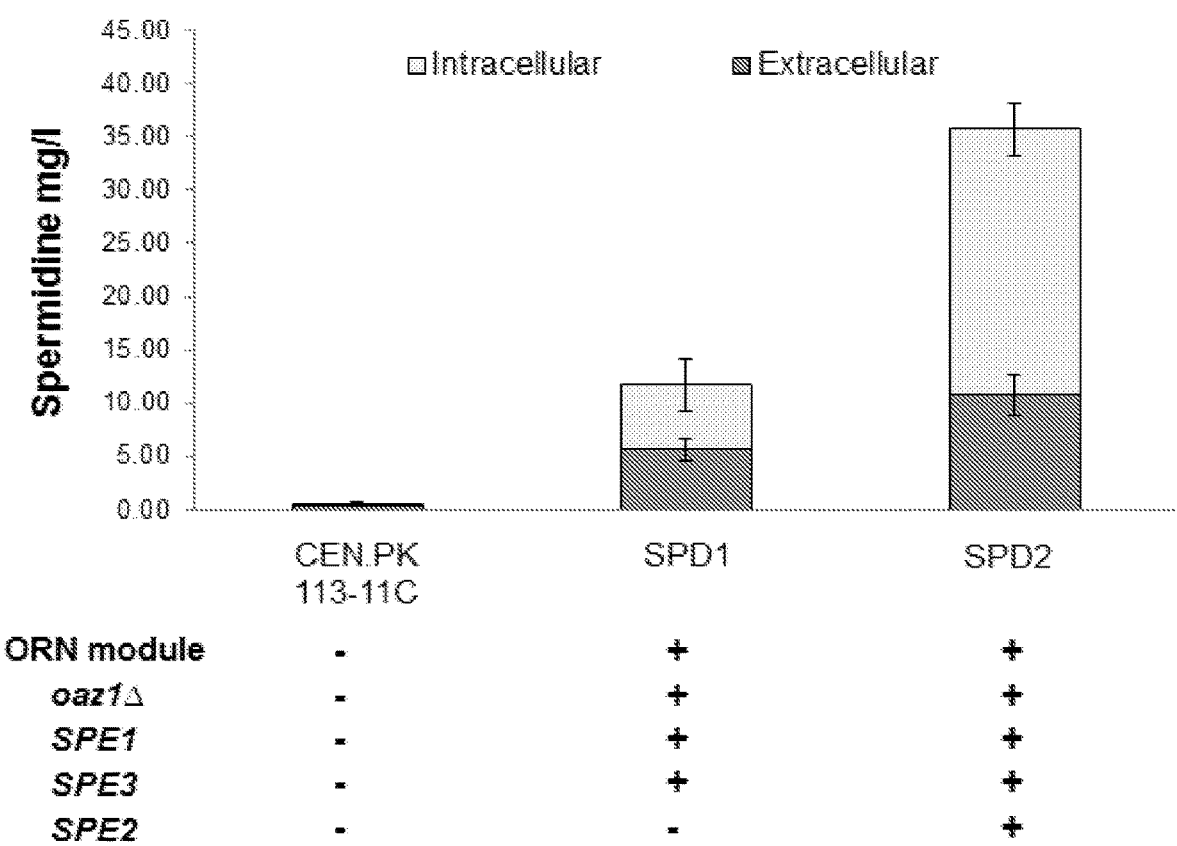
FIG. 16: Spermidine production in engineered yeast strains. Modification to the ornithine metabolism include pKEX2-ARG3, Δcar2, GDH1, ORT1, AGC1 and the cytosolic ornithine synthetic pathway in the plasmid GO4. Further engineering for spermidine production includes deletion of OAZ1 and overexpression of SPE1, SPE2 and SPE3.

The resulting strains were cultivated in minimal media and processed for spermidine quantification as described in Example 6 above. FIG. 16 shows the modified strains to produce significantly more spermidine than what is found in the control (CEN.PK113-11C) strain, with strain SPD2 producing the highest levels.

Example 8

Overexpression of an Alternative Pathway for Spermidine Production

In some bacterial species, spermidine can be produced via the condensation of L-aspartate semialdehyde and putrescine via carboxynorspermidine dehydrogenase (CANSDH) yielding carboxyspermidine, followed by decarboxylation by carboxnorspermidine decarboxylase (CANSDC). Genes encoding enzymes with these activities can be expressed to facilitate spermidine production. CANSDH and CANSDC from several organisms can be used. CjCANSDH (Cj0172c, SEQ ID NO: 46) and CjCANDC (Cj1515c, SEQ ID NO: 47) can be codon-optimized based on sequences from Campylobacter jejuni. VcCANSDH (VC1624, SEQ ID NO: 48) and VcCANDC (VC1623, SEQ ID NO: 49) can be codon-optimized based on sequences from *Vibrio cholerae*. BuCANSDH (Lys1, SEQ ID NO: 50) and BuCANDC(nspC, SEQ ID NO: 51) can be codon-optimized based on sequences from *Bacteroides uniformis*. Each pair of CANSDH and CANSDC can be cloned into the plasmid pYX212 under the promoter of TPlp and PGK1p respectively by the standard Gibson Assembly protocols with a commercial Kit from NEB. The resulting plasmids, YP1, YP2 and YP3 each encode a CANSDH and CANSDC from *C. jejuni*, *V. cholerae* and *B. uniformis*, respectively. These plasmids can be separately transformed into strain PUT-B(KanMX) together with the vector GO4 resulting in strains SPD-B1, SPD-B2 and SPD-B3, capable of producing high levels of spermidine.

Example 9

Overexpression of the Spermine Biosynthetic Pathway in *S. cerevisiae*

To increase spermine production in *S. cerevisiae*, the gene SPE1, which codes for ornithine decarboxylase (EC 4.1.1.17), can be amplified from *S. cerevisiae* (CEN.PK113-11C) genome (SEQ ID NO: 29) and cloned into vector pSP-GM1 under the control of a TEF1 promoter (Chen et al., 2012a) using standard cloning procedures. The former resulting in pSP-GM1-SPE1. The genes SPE2 (SEQ ID NO: 30) and SPE3 (SEQ ID NO: 31), encoding S-adenosylmethionine decarboxylase (EC 4.1.1.50) and spermidine synthase (EC 2.5.1.16) (respectively), can be amplified from the genome of *S. cerevisiae* (CEN.PK113-11C) using PCR. SPE2 can be cloned into pSP-GM1-SPE1 under the control of the PGK1 promoter using standard cloning procedures, resulting in plasmid pSP-GM1-SPE12. SPE3 can be cloned into pSP-GM1 (Chen et al., 2012a) under the control of a TEF1 promoter, resulting in plasmid pSP-GM1-SPE3. The TEFp-SPE3-tADH1 cassette can amplified from pSP-GM1-SPE3 and cloned into pSP-GM1-SPE12 in reverse orientation, resulting in plasmid pSP-GM1-SPD (expressing the genes SPE1, SPE2 and SPE3). Next, the gene SPE4 (SEQ ID NO: 43), encoding spermine synthase (EC 2.5.1.22) can be amplified from the genome of *S. cerevisiae* (CEN.PK113-11C) using PCR and cloned into pSP-GM1-SPE3 under the control of the PGK1 promoter, resulting in plasmid pSP-GM1-SPE34. The cassette encoding tCYC1-SPE4-PGK1p-pTEF1-SPE3-tADH1 can be then amplified from pSP-GM1-SPE34 and cloned into pSP-GM1-SPE12 in reverse orientation, resulting in plasmid pSP-GM1-SPM (expressing the genes SPE1, SPE2, SPE3 and SPE4). pSP-GM1-SPM can be transformed into strain PUT-A(KanMX) together with the vector GO4 resulting in strain AKYSPM1, capable of producing high levels of spermine.

Example 10

Increased Export of Polyamines in *S. cerevisiae*

To further increase production of putrescine, spermidine or spermine, the export of these polyamines can be increased by deleting genes associated with polyamine uptake. The AGP2, SAM3 and DUR3 genes, which are involved in polyamine uptake, can be deleted consecutively from strain PUT-B(KanMX) as described in Example 6 above, resulting in strain AKYDOAZ-Trans2. Next, AKYDOAZ-Trans2 can be co-transformed with plasmids pSP-GM1-PUT and GO4, resulting in strain AKYPUT2, capable of producing high levels of putrescine. The strain AKYDOAZ-Trans2 can also be transformed with the plasmids pSP-GM1-SPD and GO4, resulting in strain AKYSPD2, capable of producing high levels of spermidine. The strain AKYDOAZ-Trans3 can also transformed with the plasmids pSP-GM1-SPM and GO4, resulting in strain AKYSPM2, capable of producing high levels of spermine.

Example 11

Production of Agmatine in *S. cerevisiae*

To create a strain capable of producing agmatine, the gene encoding arginase (CAR1) can be deleted from strain CEN.PK113-11C using KanMX-bipartite deletion strategy as described in Example 6, resulting in strain AKYDCAR1. Next, the genes encoding for ornithine carbamoyltransferase (EC 2.1.33), argininosuccinate synthase (EC 6.3.4.5) and argininosuccinate lyase (EC 4.3.2.1), encoded by ARG3, ARG1 and ARG4 (SEQ ID NO: 34-36) can be amplified from the genome of *S. cerevisiae* (CEN.PK113-11C). ARG3 and ARG1 can be cloned into pSP-GM1 under the control of the TEF1 and PGK1 promoters, resulting in plasmid pSP-GM1-ARGA. ARG4 can be cloned into pSP-GM1, under the control of the TEF1 promoter, resulting in plasmid pSP-GM1-ARGB. The TEF1p-ARG4-tADH1 cassette can be amplified from pSP-GM1-ARGB, and cloned in reverse orientation into plasmid pSP-GM1-ARGA, resulting in plasmid pSP-GM1-ARGC (expressing ARG3, ARG1 and ARG4). The gene encoding arginine decarboxylase (EC 4.1.1.19) (speA) (SEQ ID NO: 37) can be amplified from *E. coli* (DH5α) and cloned into plasmid plYC04 (Chen et al., 2012b) under the control of the TEF1 promoter, resulting in plasmid plYC04-speA. The plasmids pSP-GM1-ARGC and plYC04-speA can be co-transformed into strain AKYD-CAR1, resulting in strain AKYAGM1, capable of producing agmatine.

To create a yeast strain capable of converting agmatine to spermidine, a bidirectional PGK1p-TEF1p promoter cassette can be amplified from plasmid pSP-GM1 via PCR. Next, the genes encoding S-adenosylmethionine decarboxylase (SPE2) (SEQ ID NO: 30) and spermidine synthase (SPE3) (SEQ ID NO: 31) can be amplified from the *S. cerevisiae* (CEN.PK113-11C) genome using overhang-containing primers that allow fusion of these genes to the PGK1p-TEF1p cassette (SPE2 under the control of TEF1p and SPE3 under the control of PGK1p). The SPE3-PGK1p-TEF1p-SPE2 cassette can then cloned into vector pXI-5 (Mikkelsen et al., 2012), resulting in vector pXI-5-SPE32, allowing the targeting of these genes into the Chr XI: 11779 . . . 118967 region of the yeast genome. This vector can be linearized and transformed into strain AKYDCAR1, followed by looping-out of the URA3 marker, resulting in strain AKYAGM2 (containing the two integrated genes).

The gene encoding agmatinase (EC 3.5.3.11) (speB) (SEQ ID NO: 38) can be amplified from *E. coli* and cloned into plYC04-speA under the control of the PGK promoter, resulting in plasmid plYC04-speAB. The plasmids plYC04-speASB and pSP-GM1-ARGC can be co-transformed into strain AKYAGM2, resulting in strain AKYAGM3, capable of converting agmatine into putrescine and spermidine.

To create a strain capable of producing spermine via the agmatine route, the PGK1p-SPE4 cassette can be amplified from plasmid pSP-GM1-SPE34 and cloned into into vector pX-4 (Mikkelsen et al., 2012), resulting in vector pX-4-SPE4, capable of targeting SPE4 to the Chr X: 236336 . . . 237310 region of the yeast genome. This vector was linearized and transformed into strain AKYAGM2, followed by looping out of the URA3 marker, resulting in strain AKYAGM4.

The plasmids pIYC04-speAB and pSP-GM1-ARGC can be co-transformed into strain AKYAGM4, resulting in strain AKYAGM5, capable of converting agmatine into putrescine, spermidine and spermine.

Example 12

Production of Spermidine/Spermine in *Escherichia coli*

Modifications in *E. coli* WL3110 (orig. K12 W3110 (CGSC, *Coli* Genetic Stock Center); (Park et al. 2007)) to increase ornithine and putrescine production respectively can be implemented as described in Quian et al. (2009). For example these comprise enhancing precursor supply (deletion of argI gene), inactivating putrescine degradation and utilization pathways (deletion of speG; puuPA, argR) and deletion of rpoS, a stress responsive polymerase sigma factor. Also genes coding for ornithine decarboxylase converting ornithine to putrescine and ornithine biosynthetic genes (argC-E) can be overexpressed either through plasmids or chromosomal integration. This platform strain can be transformed with either plasmids for overexpression of endogenous or heterologous speE (E.C.: 2.5.1.16; SEQ ID NO: 37) and speD (EC 4.1.1.50; SEQ ID NO: 39) genes. For example the expression vector pTRC-LIC (Plasmid #62343; Addgene (Massachusetts, USA)) is used to systematically co-express the mentioned genes under control of the strong $P_{trc}$ promoter. Cloning is done via amplification of target genes through 30 bp overhang primers to the expression vector ($P_{trc}$ promoter control) and carried out via the Gibson cloning approach (Gibson et al. 2009). Alternatively chromosomal replacement of promoters of these genes with a constitutive active strong hybrid-promoter like $P_{trc}$ can be performed. To facilitate increased spermidine export, genes coding for exporters e.g. the mdtJI complex genes (SEQ ID NO: 40-41) can be overexpressed through plasmid based expression or promoter exchange as described above. The gene coding for the spermidine exporter blt from *B. subtilis* (SEQ ID NO: 42) can be amplified from *B. subtilis* genomic DNA and also hetorologously expressed under *E. coli* promoter control (e.g. $P_{trc}$). For the tailored production of spermine heterologous spermine synthases (E.C. 2.5.1.22) from eukaryotic sources are expressed e.g. derived from *S. cerevisiae*, *Triticum aestivum*, *Oryza sativa*, *Glycine max*, *Citrus sinesis*, *Homo sapiens*. For example spermine synthase gene SPE4 (GI: 3201942; SE ID NO: 43) can be amplified from *S. cerevisiae* genomic DNA (CEN.PK113-11C) using PCR with 30 bp overhang primers and cloned via Gibson cloning (Gibson et al. 2009) into expression vector pTRC.

Example 13

Production of Spermidine/Spermine in *Corynebacterium glutanicum*

Modifications to increase ornithine production in *C. glutamicum* strain ATCC 13032 can be performed as described in Kim et al. (2015): deletion of proB and argF (block competing pathways); deletion of argR gene (repressor of the L-arginine operon); overexpression of argCJBD from *C. glutanicum* ATCC 21831; start codon change of pgi and zwf (enrichment of NADPH pool), replacing native promoter of tkt operon with a strong sod promoter. For increased putrescine production the strain can be further engineered as described in Schneider et al. (2010): The strain was modified with overexpression of ornithine decarboxylase speC (EC 4.1.1.19; SEQ ID NO: 44) from *E. coli* and chromosomal deletion of carbamoyl-transferase argF. For increased spermidine production endogenous spermidine synthase gene speE (SEQ ID NO: 45) can be either overexpressed through plasmid based expression or intregrating of multiple copies into the genome. For example, *E. coli*-*C. glutanicum* shuttle vector pMS2 (ATTC®67189TM) with kanamycin as selective marker is used for plasmid based overexpression of heterologous speD. For plasmid construction two fragments can be amplified: fragment containing the $P_{tac}$ promoter and lad gene derived from pTAC-MAT-Tag®-1 (Sigma) and the speD gene from *E. coli* genomic DNA (SEQ ID NO: 39). 30 bp overhanging primers can be used to amplify fragments

TABLE 1

Background strains constructed for ornithine production.

| No | Strain name | Genotype |
|---|---|---|
| 1 | ORN-A | MATa SUC2 MAL2-8c ura3-52 his3-Δ1 $P_{ARG3}$::$P_{HXT1}$ |
| 2 | ORN-B | MATa SUC2 MAL2-8c ura3-52 his3-Δ1 $P_{ARG3}$::$P_{KEX2}$ |
| 3 | ORN-E(KanMX) | MATa SUC2 MAL2-8c ura3-52 his3-Δ1 $P_{ARG3}$::$P_{KEX2}$ car2::LoxP-KanMX-LoxP |
| 4 | ORN-F(KanMX) | MATa SUC2 MAL2-8c ura3-52 his3-Δ1 $P_{ARG3}$::$P_{KEX2}$ car2::LoxP-KanMX-LoxP-$P_{TPI}$-ORT1-$T_{pYX212}$ |
| 5 | ORN-G(KanMX) | MATa SUC2 MAL2-8c ura3-52 his3-Δ1 $P_{ARG3}$::$P_{KEX2}$ car2::LoxP-KanMX-LoxP-$T_{CTC1}$-AGC1-$P_{tHXT1}$-$P_{TPI}$-ORT1-$T_{pYX212}$ |
| 6 | ORN-F | MATa SUC2 MAL2-8c ura3-52 his3-Δ1 $P_{ARG3}$::$P_{KEX2}$ car2::LoxP-$P_{TPI}$-ORT1-$T_{pYX212}$ |
| 7 | ORN-G | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ |
| 8 | ORN-H(KanMX) | MATa SUC2 MAL2-8c ura3-52 his3-Δ1 $P_{ARG3}$::$P_{KEX2}$ car2::LoxP-$P_{TPI}$-ORT1-$T_{pYX212}$ ura3:: LoxP-KanMX-LoxP-$P_{TEF1}$-GDH1-$T_{DIT1}$ |
| 9 | ORN-I(KanMX) | MATa SUC2 MAL2-8c ura3-52 his3-Δ1 $P_{ARG3}$::$P_{KEX2}$ car2::LoxP-$P_{TPI}$-ORT1-$T_{pYX212}$ ura3:: LoxP-KanMX-LoxP-$T_{TDH2}$-ODC1-$P_{PGK1}$-$P_{TEF1}$-GDH1-$T_{DIT1}$ |
| 10 | ORN-J(KanMX) | MATa SUC2 MAL2-8c ura3-52 his3-Δ1 PARG3::PKEX2 car2::LoxP-PTPI-ORT1-TpYX212 ura3:: LoxP-KanMX-LoxP-PTEF1-MLS-GDH1-TDIT1 |
| 11 | ORN-K(KanMX) | MATa SUC2 MAL2-8c ura3-52 his3-Δ1 PARG3::PKEX2 car2::LoxP-PTPI-ORT1-TpYX212 ura3:: LoxP-KanMX-LoxP-PTEF1-MLS-GDH2-TDIT1 |
| 12 | ORN-J | MATa SUC2 MAL2-8c ura3-52 his3-Δ1 PARG3::PKEX2 car2::LoxP-PTPI-ORT1-TpYX212 ura3:: LoxP-PTEF1-MLS-GDH1-TDIT1 |
| 13 | ORN-L(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ ura3:: LoxP-KanMX-LoxP-PTEF1-GDH1-TDIT1 |
| 14 | ORN-M(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-KanMX-LoxP-PTEF1-GDH3-TDIT1 |

TABLE 1-continued

Background strains constructed for ornithine production.

| No | Strain name | Genotype |
|---|---|---|
| 15 | ORN-N(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-KanMX-LoxP-TTDH2-ODC1-PPGK1-PTEF1-GDH3-TDIT1 |
| 16 | ORN-O(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-KanMX-LoxP-TTDH2-ODC1-PPGK1-PTEF1-GDH1-TDIT1 |
| 17 | ORN-P(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ YPRT3:: LoxP-KanMX-LoxP-PTEF1-AOX1-TPRM9 |
| 18 | ORN-Q(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$YPRT3:: LoxP-KanMX-LoxP-TpYX212-NDI1-PPGK1-PTEF1-AOX1-TPRM9 |
| 19 | ORN-R(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-KanMX-LoxP-PTEF1-MLS-GDH1-TDIT1 |
| 20 | ORN-L | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 |
| 21 | ORN-O | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-TTDH2-ODC1-PPGK1-PTEF1-GDH1-TDIT1 |
| 22 | ORN-S(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 kgd2:: LoxP-KanMX-LoxP |
| 23 | ORN-T(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 kgd2:: LoxP-KanMX-LoxP-TPRM9t-MTH1-PTEF1 |
| 24 | ORN-U(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 kgd2:: LoxP-KanMX-LoxP-TPRM9t-AOX1-PTEF1 |
| 25 | ORN-V(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 YPRT3:: LoxP-KanMX-LoxP-PTEF1-MTH1-TPRM9 |
| 26 | ORN-WN(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 YPRT3:: LoxP-KanMX-LoxP-PTEF1-AOX1-TPRM9 |
| 27 | ORN-W(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-PTEF1-GDH1-TDIT1 YPRT3:: LoxP-KanMX-LoxP-PTEF1-AOX1-TPRM9 |
| 28 | ORN-X(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-TTDH2-ODC1-PPGK1-PTEF1-GDH1-TDIT1 YPRT3:: LoxP-KanMX-LoxP-PTEF1-AOX1-TPRM9 |
| 29 | ORN-Y(KanMX) | MATa SUC2 MAL2-8c ura3-52 his3-Δ1 PARG3::PKEX2 car2::LoxP-TCTC1-AGC1-PtHXT1-PTPI-ORT1-TpYX212ura3:: LoxP-TTDH2-ODC1-PPGK1-PTEF1-GDH1-TDIT1 kgd2:: LoxP-KanMX-LoxP-TPRM9t-AOX1-PTEF1 |
| 30 | ORN-Z(KanMX) | MATa SUC2 MAL2-8c ura3-52 his3-Δ1 $P_{ARG3}$::$P_{KEX2}$ car2::LoxP-$T_{CTC1}$-AGC1-$P_{tHXT1}$-$P_{TPI}$-ORT1-$T_{pYX212}$ura3:: LoxP-TTDH2-ODC1-PPGK1-PTEF1-GDH1-TDIT1 kgd2:: LoxP-KanMX-LoxP |
| 31 | B0166A CEN.PK | MATa ORT1Δ |
| 32 | CEN.PK113-11C | MATa SUC2 MAL2-8$^c$ ura3-52 his3-Δ1 | and subsequently cloned via Gibson cloning (Gibson et al. 2009) into the shuttle vector pMS2 with speD under $P_{tac}$ control creating the expression vector pFDAMS2. After transformation into modified *C. glutanicum* strain ATCC 13032 strain (see above) it can be cultivated as described in Schneider et al. 2010. To facilitate increased spermidine export, genes coding for exporters e.g. mdtJl from *E. coli* (SEQ ID NO: 40-41) or bit from *B. subtilis* (SEQ ID NO: 42) can be amplified from *E. coli* genomic DNA respective *B. subtilis* genomic DNA and also heterologously expressed in *C. glutanicum* as described above. For the tailored production of spermine heterologous spermine synthases (E.C. 2.5.1.22) from eukaryotic sources can be expressed. via plasmid-based expression (see above). For example spermine synthases can be derived from *S. cerevisiae* (Spe4, GI: 3201942; SEQ ID NO: 43), *Triticum aestivum, Oryza sativa, Glycine max, Citrus sinesis, Homo sapiens*.

TABLE 2

Strains used for module and full ornithine pathway optimization

| | | Module 1 | | Module 2 | | Module 3 | | Background | Reference Plasmid 1(URA) | Plasmid 2(HIS) |
|---|---|---|---|---|---|---|---|---|---|---|
| No | Strain name | Module | Desc | Module | Desc | Module | Desc | strain | | |
| 1 | M1a | M1a | $P_{HXT1}$-ARG3 | Null | Null | Null | Null | ORN-A | pYX212 | p423GPD |
| 2 | M1b | M1b | $P_{KEX2}$-ARG3 | Null | Null | Null | Null | ORN-B | pYX212 | p423GPD |

TABLE 2-continued

Strains used for module and full ornithine pathway optimization

| No | Strain name | Module 1 Module | Module 1 Desc | Module 2 Module | Module 2 Desc | Module 3 Module | Module 3 Desc | Reference Background strain | Plasmid 1(URA) | Plasmid 2(HIS) |
|---|---|---|---|---|---|---|---|---|---|---|
| 3 | M1c | M1c | $P_{KEX2}$-ARG3; CAR2Δ | Null | Null | Null | Null | ORN-E(KanMX) | pYX212 | p423GPD |
| 4 | M1cM2a | M1c | $P_{KEX2}$-ARG3; CAR2Δ | M2a | ARG2 | Null | Null | ORN-E(KanMX) | pSPGM1-ARG2 | p423GPD |
| 5 | M1cM2b | M1c | $P_{KEX2}$-ARG3; CAR2Δ | M2b | ARG5,6 | Null | Null | ORN-E(KanMX) | pSPGM1-ARG5,6 | p423GPD |
| 6 | M1cM2c | M1c | $P_{KEX2}$-ARG3; CAR2Δ | M2c | ARG7 | Null | Null | ORN-E(KanMX) | pSPGM1-ARG7 | p423GPD |
| 7 | M1cM2d | M1c | $P_{KEX2}$-ARG3; CAR2Δ | M2d | MLS-argB$_{Cg}$ | Null | Null | ORN-E(KanMX) | pYX212-argB$_{Ec}$ | p423GPD |
| 8 | M1cM2e | M1c | $P_{KEX2}$-ARG3; CAR2Δ | M2e | MLS-argJ$_{Cg}$ | Null | Null | ORN-E(KanMX) | pYX212-argJ$_{Cg}$ | p423GPD |
| 9 | M1cM2f | M1c | $P_{KEX2}$-ARG3; CAR2Δ | M2f | ARG5,6; ARG7; ARG8 | Null | Null | ORN-E(KanMX) | pYX212 | GO1 |
| 10 | M1cM2g | M1c | $P_{KEX2}$-ARG3; CAR2Δ | M2g | ARG5,6; ARG7; ARG8; ARG2 | Null | Null | ORN-E(KanMX) | pYX212 | GO2 |
| 11 | M1cM2h | M1c | $P_{KEX2}$-ARG3; CAR2Δ | M2h | ARG5,6; ARG7; ARG8; ARG2; ORT1 | Null | Null | ORN-F | pYX212 | GO2 |
| 12 | M1cM2i | M1c | $P_{KEX2}$-ARG3; CAR2Δ | M2i | ARG5,6; ARG7; ARG8; ARG2; ORT1; MLS-GDH1 | Null | Null | ORN-J(KanMX) | pYX212 | GO2 |
| 13 | M1cM2j | M1c | $P_{KEX2}$-ARG3; CAR2Δ | M2j | ARG5,6; ARG7; ARG8; ARG2; ORT1; MLS-GDH2 | Null | Null | ORN-K(KanMX) | pYX212 | GO2 |
| 14 | M1cM2k | M1c | $P_{KEX2}$-ARG3; CAR2Δ | M2k | ARG5,6; ARG7; ARG8; ARG2; ORT1; AGC1 | Null | Null | ORN-G | pYX212 | GO2 |
| 15 | M1cM2l | M1c | $P_{KEX2}$-ARG3; CAR2Δ | M2l | ARG5,6; ARG7; ARG8; ARG2; ORT1; AGC1; GDH1 | Null | Null | ORN-L(KanMX) | pYX212 | GO2 |
| 16 | M1cM2m | M1c | $P_{KEX2}$-ARG3; CAR2Δ | M2m | ARG5,6; ARG7; ARG8; ARG2; ORT1; AGC1; GDH3 | Null | Null | ORN-M(KanMX) | pYX212 | GO2 |
| 17 | M1cM2n | M1c | $P_{KEX2}$-ARG3; CAR2Δ | M2n | ARG5,6; ARG7; ARG8; ARG2; ORT1; AGC1; GLN1; GLT1 | Null | Null | ORN-G | YO1 | GO2 |

TABLE 2-continued

Strains used for module and full ornithine pathway optimization

| No | Strain name | Module 1 Module | Module 1 Desc | Module 2 Module | Module 2 Desc | Module 3 Module | Module 3 Desc | Reference Background strain | Plasmid 1(URA) | Plasmid 2(HIS) |
|---|---|---|---|---|---|---|---|---|---|---|
| 18 | M1cM2o | M1c | $P_{KEX2}$-ARG3; CAR2Δ | M2o | ARG5,6; ARG7; ARG8; ARG2; ORT1; AGC1; GDH3; ODC1 | Null | Null | ORN-N(KanMX) | pYX212 | GO2 |
| 19 | M1cM2p | M1c | $P_{KEX2}$-ARG3; CAR2Δ | M2p | ARG5,6; ARG7; ARG8; ARG2; ORT1; AGC1; GDH1; ODC1 | Null | Null | ORN-O(KanMX) | pYX212 | GO4 |
| 20 | M1cM2q | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | Null | Null | ORN-O(KanMX) | pYX212 | GO4 |
| 21 | M1cM2r | M1c | $P_{KEX2}$-ARG3; CAR2Δ | M2r | PADH1-tGCN4 | Null | Null | ORN-E(KanMX) | pYX212 | PADH1-tGCN4 |
| 22 | M1cM2s | M1c | $P_{KEX2}$-ARG3; CAR2Δ | M2s | PTEF1-tGCN4 | Null | Null | ORN-E(KanMX) | pYX212 | PTEF1-tGCN4 |
| 23 | M1cM2t | M1c | $P_{KEX2}$-ARG3; CAR2Δ | M2t | PGPD1-tGCN4 | Null | Null | ORN-E(KanMX) | pYX212 | PGPD1-tGCN4 |
| 24 | M1cM2qM3a | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | M3a | PDA1; CIT1; ACO2; IDP1; PYC2 | ORN-L(KanMX) | YO4 | GO4 |
| 25 | M1cM2qM3b | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | M3b | mPDA1; CIT1; ACO2; IDP1; PYC2 | ORN-L(KanMX) | YO5 | GO4 |
| 26 | M1cM2qM3c | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | M3c | HcAOX1 | ORN-W(KanMX) | pYX212 | GO4 |
| 27 | M1cM2qM3d | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | M3d | HcAOX1; NDI1 | ORN-WN(KanMX) | pYX212 | GO4 |

TABLE 2-continued

Strains used for module and full ornithine pathway optimization

| No | Strain name | Module 1 Module | Module 1 Desc | Module 2 Module | Module 2 Desc | Module 3 Module | Module 3 Desc | Background strain | Reference Plasmid 1(URA) | Plasmid 2(HIS) |
|---|---|---|---|---|---|---|---|---|---|---|
| 28 | M1cM2qM3e | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | M3e | tMTH1 | ORN-V(KanMX) | pYX212 | GO4 |
| 29 | M1cM2qM3f | M1c | $P_{KEX2}$-ARG3; CAR2Δ | M2q | $argA_{Ec}$; $argB_{Ec}$; $argC_{Cg}$; $argD_{Cg}$; $argJ_{Cg}$; ORT1; AGC1; GDH1 | M3f | tMTH1; ΔKGD2 | ORN-T(KanMX) | pYX212 | GO4 |
| 30 | M1dM2q | M1d | $P_{KEX2}$-ARG3; CAR2Δ; CAR1 | M2q | $argA_{Ec}$; $argB_{Ec}$; $argC_{Cg}$; $argD_{Cg}$; $argJ_{Cg}$; ORT1; AGC1; GDH1 | Null | Null | ORN-L(KanMX) | TPIp-CAR1 | GO4 |
| 31 | M1dM2qM3c | M1d | $P_{KEX2}$-ARG3; CAR2Δ; CAR1 | M2q | $argA_{Ec}$; $argB_{Ec}$; $argC_{Cg}$; $argD_{Cg}$; $argJ_{Cg}$; ORT1; AGC1; GDH1 | M3c | HaAOX1 | | | |
| 32 | M1dM2qM3e | M1d | $P_{KEX2}$-ARG3; CAR2Δ; CAR1 | M2q | $argA_{Ec}$; $argB_{Ec}$; $argC_{Cg}$; $argD_{Cg}$; $argJ_{Cg}$; ORT1; AGC1; GDH1 | M3e | tMTH1 | ORN-V(KanMX) | TPIp-CAR1 | GO4 |
| 33 | M1dM2qM3f | M1d | $P_{KEX2}$-ARG3; CAR2Δ; CAR1 | M2q | $argA_{Ec}$; $argB_{Ec}$; $argC_{Cg}$; $argD_{Cg}$; $argJ_{Cg}$; ORT1; AGC1; GDH1 | M3f | tMTH1; ΔKGD2 | ORN-T(KanMX) | TPIp-CAR1 | GO4 |
| 34 | B0166A(ORT1) | Null | Null | Null | Null | Null | Null | B0166A CEN.PK | pYX212 | GO4 |

TABLE 3

List of strains used for polyamine production

| Strain name | Background genotype | Plasmids |
|---|---|---|
| PUT-A(KanMX) | ORN-LΔoaz1 | None |
| WT-PUT-A(KanMX) | CEN.PK113-11C Δoaz1 | None |
| PUT1 | ORN-LΔoaz1 | p426GPD, GO4 |
| WT-PUT1 | CEN.PK113-11C Δoaz1 | p426GPD, p423GPD |
| PUT-B(KanMX) | ORN-L Δoaz1 SPE1 | none |
| WT-PUT-B(KanMX) | CEN.PK113-11C Δoaz1 SPE1 | none |
| PUT2 | ORN-L Δoaz1 SPE1 | p426GPD, GO4 |
| WT-PUT2 | CEN.PK113-11C Δoaz1 SPE1 | p426GPD, p423GPD |
| PUT3 | ORN-L Δoaz1 SPE1 | P412GPD-TPO1, GO4 |

TABLE 3-continued

List of strains used for polyamine production

| Strain name | Background genotype | Plasmids |
|---|---|---|
| WT-PUT3 | CEN.PK113-11C Δoaz1 SPE1 | P412GPD-TPO1, p423GPD |
| SPD-A(KanMX) | ORN-L Δoaz1 SPE1 SPE3 | none |
| SPD1 | ORN-L Δoaz1 SPE1 SPE3 | p426GPD, GO4 |
| SPD2 | ORN-L Δoaz1 SPE1 SPE3 SPE2 | p426GPD, GO4 |
| SPD-B(KanMX) | ORN-L Δoaz1 SPE1 SPE3 SPE2 | none |
| SPD-B1 | ORN-L Δoaz1 SPE1 | YP1, GO4 |
| SPD-B2 | ORN-L Δoaz1 SPE1 | YP2, GO4 |
| SPD-B3 | ORN-L Δoaz1 SPE1 | YP3, GO4 |
| AKYSPM1 | ORN-V(KanMX) Δoaz1 | pSP-GM1-SPM1, GO4 |
| AKYDOAZ-Trans1 | AKYDOAZ TPO1 TPO5 | none |
| AKYDOAZ-Trans2 | PUT-A(KanMX) Δsam3 Δdur3 | none |
| AKYPUT2 | AKYDOAZ TPO1 TPO5 Δsam3 Δdur3 | pSP-GM1-PUT, GO4 |
| AKYSPD2 | AKYDOAZ TPO1 TPO5 Δsam3 Δdur3 | pSP-GM1-SPD, GO4 |
| AKYSPM2 | AKYDOAZ TPO1 TPO5 Δsam3 Δdur3 | pSP-GM1-SPM, GO4 |
| AKYDCAR1 | CEN.PK113-11C Δcar1 | none |
| AKYAGM1 | CEN.PK113-11C Δcar1 | pSP-GM1-ARGC, pIYC04-speA |
| AKYAGM2 | CEN.PK113-11C Δcar1 SPE2 SPE3 | |
| AKYAGM3 | CEN.PK113-11C Δcar1 SPE2 SPE3 | pSP-GM1-ARGC, pIYC04-speAB |
| AKYAGM4 | CEN.PK113-11C Δcar1 SPE2 SPE3 SPE4 | |
| AKYAGM5 | CEN.PK113-11C Δcar1 SPE2 SPE3 SPE4 | pSP-GM1-ARGC, pIYC04-speAB |
| C. glutanicum ATCC 13032 | Kalinowski et al. (2003) | Background strain for spermidine/spermine production in C. glutanicum |
| E. coli WL3110 | orig. K12 W3110 (CGSC, Coli Genetic Stock Center); (Park et al. 2007)) | Background strain for spermidine/spermine production in E. coli |

TABLE 4

Plasmids used in this study

| No | Plasmid/Alias Name | Genes Insert | Skeleton Vector | Marker | Reference |
|---|---|---|---|---|---|
| 1 | GO1 | ARG5,6; ARG7; ARG8 | p423GPD | HIS3 | This Study |
| 2 | GO2 | ARG5,6; ARG7; ARG8; ARG2 | p423GPD | HIS3 | This Study |
| 3 | GO3 | ARG5,6 ARG7; ARG8; ARG2; CAR1 | p423GPD | HIS3 | This Study |
| 4 | GO4 | argB$_{Ec}$; argA$_{E;c}$ argC$_{Cg}$; argD$_{Cg}$; argJ$_{Cg}$ | p423GPD | HIS3 | This Study |
| 5 | YO1 | GLN1; GLT1 | pYX212 | URA3 | This Study |
| 6 | YO2 | PYC2; CIT1; IDP1 | pYX212 | URA3 | This Study |
| 7 | YO3 | GLN1; GLT1; PYC2; CIT1; IDP1 | pYX212 | URA3 | This Study |
| 8 | YO4 | PDA1; ACO2; PYC2; CIT1; IDP1 | pYX212 | URA3 | This Study |
| 9 | YO5 | mPDA1; ACO2; PYC2; CIT1; IDP1 | pYX212 | URA3 | This Study |
| 10 | pSPGM1-ARG2 | ARG2 | pSPGM1 | URA3 | This Study |
| 11 | pSPGM1-ARG5,6 | ARG5,6 | pSPGM1 | URA3 | This Study |
| 12 | pSPGM1-ARG7 | ARG7 | pSPGM1 | URA3 | This Study |
| 13 | pYX212-MLSargB$_{Cg}$ | MLS-argB$_{Cg}$ | pYX212 | URA3 | This Study |
| 14 | pYX212-MLS-argJ$_{Cg}$ | MLS-argJ$_{Cg}$ | pYX212 | URA3 | This Study |
| 15 | PADH1-tGCN4 | tGCN4 | p423ADH | HIS3 | This Study |
| 16 | PTEF1-tGCN4 | tGCN4 | p423TEF | HIS3 | This Study |
| 17 | PGPD1-tGCN4 | tGCN4 | p423GPD | HIS3 | This Study |
| 18 | TPIp-CAR1 | CAR1 | pYX212 | URA3 | (Johansson et al., 2014) |
| 19 | pRS416-PDA1 [S313A] | PDA1 [S313A] | pRS416 | URA3 | (Oliviera et al., 2012) |
| 20 | pRS416-PDA1 | PDA1 | pRS416 | URA3 | (Oliviera et al., 2012) |
| 21 | pSP-GM1-SPE1 | P$_{TEF1}$-SPE1 | pSP-GM1 | URA3 | This study |
| 22 | pSP-GM1-SPE12 | P$_{TEF1}$-SPE1, P$_{PGK1}$-SPE2 | pSP-GM1 | URA3 | This study |
| 23 | pSP-GM1-SPE3 | P$_{TEF1}$-SPE3 | pSP-GM1 | URA3 | This study |
| 24 | pSP-GM1-SPD | P$_{TEF1}$-SPE1, P$_{PGK1}$-SPE2, P$_{TEF1}$-SPE3 | pSP-GM1 | URA3 | This study |
| 25 | pSP-GM1-SPE34 | P$_{TEF1}$-SPE3, P$_{PGK1}$-SPE4 | pSP-GM1 | URA3 | This study |

TABLE 4-continued

Plasmids used in this study

| No | Plasmid/Alias Name | Genes Insert | Skeleton Vector | Marker | Reference |
|---|---|---|---|---|---|
| 26 | pSP-GM1-SPM | $P_{TEF1}$-SPE1, $P_{PGK1}$-SPE2, $P_{TEF1}$-SPE3, $P_{PGK1}$-SPE4 | pSP-GM1 | URA3 | This study |
| 27 | pXI-3-TPO15 | $P_{TEF1}$-TPO1, $P_{PGK1}$-TPO5 | pXI-3 | URA3 | This study |
| 28 | pSP-GM1-ARGA | $P_{TEF1}$-ARG3, $P_{PGK1}$-ARG1 | pSP-GM1 | URA3 | This study |
| 29 | pSP-GM1-ARGB | $P_{TEF1}$-ARG10, $P_{PGK1}$-ARG4 | pSP-GM1 | URA3 | This study |
| 30 | pSP-GM1-ARGC | $P_{TEF1}$-ARG3, $P_{PGK1}$-ARG1 $P_{TEF1}$-ARG10, $P_{PGK1}$-ARG4 | pSP-GM1 | URA3 | This study |
| 31 | pIYC04-speA | $P_{TEF1}$-speA | pIYC04 | HIS3 | This study |
| 32 | pXI-5-SPE32 | $P_{TEF1}$-SPE2, $P_{PGK1}$-SPE3 | pXI-5 | URA3 | This study |
| 33 | pIYC04-speAB | $P_{TEF1}$-speA, $P_{PGK1}$-speB | pIYC04 | HIS3 | This study |
| 34 | pX-4-SPE4 | $P_{TEF1}$-SPE4 | pX-4 | URA3 | This study |
| 35 | pSP-GM1 | Episomal backbone | | URA3 | (Chen et al., 2012a) |
| 36 | pIYC04 | Episomal backbone | | HIS3 | (Chen et al., 2012b) |
| 37 | pXI-3 | Integrative backbone | | URA3 | (Mikkelsen et al., 2012) |
| 38 | pXI-5 | Integrative backbone | | URA3 | (Mikkelsen et al., 2012) |
| 39 | pX-4 | Integrative backbone | | URA3 | (Mikkelsen et al., 2012) |
| 40 | pMS2 ATTC ®67189TM | shuttle vector E. coli-C. glutanicum | | ampR, kanR | U.S. Pat. No. 4,920,054 |
| 41 | pTAC-MAT-Tag ®-1 (Sigma) | LacI, tac promoter amplification | | ampR | Rosenberg et al. (1987). |
| 42 | pFDAMS2 | Episomal expression vector for C. glutanicum (tac promoter control + target gene (e.g. speD) | pMS2 | ampR | Example 11 |
| 43 | pTRC-LIC | Episomal expression vector for E. coli; (tac promoter from pKK233-2) | pTRC99a | ampR | GenBank Accession: EF460847 |
| 44 | p426GPD | Episomal backbone | | URA3 | Mumberg et al., 1995 |
| 45 | pYX212 | Episomal backbone | | URA3 | R&D systems |
| 46 | p423GPD | Episomal backbone | | HIS3 | Mumberg et al., 1995 |
| 47 | pTPO1 | TDH3p-TPO1-CYC1t | p426GPD | URA3 | This study |
| 48 | YP1 | (TPIp-CjCASDH-FBA1t) + (PGK1p-CjCASDC-CYC1t) | pYX212 | URA3 | This study |
| 49 | YP2 | (TPIp-VcCASDH-FBA1t) + (PGK1p-VcCASDC-CYC1t) | pYX212 | URA3 | This study |
| 50 | YP3 | (TPIp-BuCASDH-FBA1t) + (PGK1p-BuCASDC-CYC1t) | pYX212 | URA3 | This study |

REFERENCES

Avalos J L, Fink G R, Stephanopoulos G (2013) Compartmentalization of metabolic pathways in yeast mitochondria improves the production of branched-chain alcohols. Nat Biotechnol 31(4):335-341 doi:10.1038/nbt.2509

Canelas, A. B., et al. (2009). "Quantitative Evaluation of Intracellular Metabolite Extraction Techniques for Yeast Metabolomics." Anal. Chem. 81(17): 7379-7389.

Chen, Y., Partow, S., Scalcinati, G., Siewers, V., Nielsen, J., 2012a. Enhancing the copy number of episomal plasmids in Saccharomyces cerevisiae for improved protein production. FEMS Yeast Res. 12, 598-607.

Chen, Y., Daviet, L., Schalk, M, Siewers, V, Nielsen, J., 2012b. Establishing a platform cell factory through engineering of yeast Acetyl-CoA metabolism. Metab Eng. 15:48-54.

Chinard, F. P. Photometric estimation of proline and ornithine. J. Biol. Chem. 199, 91-95(1952).

Choi H, Kyeong H H, Choi J M, Kim H S. 2014. Rational design of ornithine decarboxylase with high catalytic activity for the production of putrescine. Appl Microbiol Biotechnol. 98(17):7483-90

Erdeniz, N., Mortensen, U. H., Rothstein, R., 1997. Cloning-free PCR based allele replacement methods. Genome Res. 7, 1174-1183.

Flagfeldt, D B., Siewers, V., Huang, L. & Nielsen, J. Characterization of chromosomal integration sites for heterologous gene expression in Saccharomyces cerevisiae. Yeast 26, 545-551 (2009).

Gietz, R. D., Woods, R. A., 2002. Transformation of yeast by lithium acetate/single-stranded carrier DNA/polyethylene glycol method. Meth. Enzymol. 350, 87-96.

Güldener, U., Heck, S., Fiedler, T., Beinhauer, J., Hegemann, J. H., 1996. A new efficient gene disruption cassette for repeated use in budding yeast. Nucleic Acids Res. 24, 2519-2524.

Hwang G-H, Cho J-Y (2012) Implication of gluconate kinase activity in l-ornithine biosynthesis in Corynebacterium glutamicum. J Ind Microbiol Biotechnol 39(12): 1869-1874 doi:10.1007/s10295-012-1197-7

Hwang G-H, Cho J-Y (2014) Enhancement of l-ornithine production by disruption of three genes encoding putative oxidoreductases in Corynebacterium glutamicum. J Ind Microbiol Biotechnol 41(3):573-578 doi:10.1007/s10295-013-1398-8

Hwang J H, Hwang G H, Cho J Y (2008) Effect of increased glutamate availability on L-ornithine production in Corynebacterium glutamicum. J Microbiol Biotechnol 18(4):704-710

Jiang L-Y, Zhang Y-Y, Li Z, Liu J-Z (2013a) Metabolic engineering of Corynebacterium glutamicum for increasing the production of l-ornithine by increasing NADPH availability. J Ind Microbiol Biotechnol 40(10):1143-1151 doi:10.1007/s10295-013-1306-2

Jiang L Y, Chen S G, Zhang Y Y, Liu J Z (2013b) Metabolic evolution of Corynebacterium glutamicum for increased production of L-ornithine. BMC Biotechnol 13:11 doi: 10.1186/1472-6750-13-47

Johansson N1, Persson K O, Quehl P, Norbeck J, Larsson C. (2014). Ethylene production in relation to nitrogen metabolism in Saccharomyces cerevisiae. FEMS Yeast Res. 14(7):1110-8.

Kalinowski, Jam, et al. "The complete Corynebacterium glutamicum ATCC 13032 genome sequence and its impact on the production of L-aspartate-derived amino acids and vitamins." Journal of biotechnology 104.1 (2003): 5-25.

Kim S Y, Lee J, Lee S Y (2014) Metabolic engineering of Corynebacterium glutamicum for the production of L-ornithine. Biotechnol Bioeng:n/a-n/a doi:10.1002/bit.25440

Kim, S.-K., et al. (2015). "Enhanced tolerance of Saccharomyces cerevisiae to multiple lignocellulose-derived inhibitors through modulation of spermidine contents." Metabolic Engineering 29: 46-5

Mikkelsen M D, Buron L D, Salomonsen B, Olsen C E, Hansen B G, Mortensen U H, Halkier B A. 2012. Microbial production of indolylglucosinolate through engineering of a multi-gene pathway in a versatile yeast expression platform. Metab Eng. 14(2):104-11.

Mumberg D1, Müller R, Funk M. Yeast vectors for the controlled expression of heterologous proteins in different genetic backgrounds. Gene. 1995; 156(1):119-22.

Oliveira A P, Ludwig C, Picotti P, Kogadeeva M, Aebersold R, Sauer U (2012) Regulation of yeast central metabolism by enzyme phosphorylation, vol 8, Oud B, Flores C-L, Gancedo C, Zhang X, Trueheart J, Daran J-M, Pronk J, van Maris A (2012) An internal deletion in MTH1 enables growth on glucose of pyruvate-decarboxylase negative, non-fermentative Saccharomyces cerevisiae. Micro Cell Fact 11(1):131

Park J H, Lee K H, Kim T Y, Lee S Y (2007) Metabolic engineering of Escherichia coli for the production of L-valine based on transcriptome analysis and in silico gene knockout simulation. Proc Natl Acad Sci USA 104(19):7797-7802 doi:10.1073/pnas.0702609104

Patchett M L, Daniel R M, Morgan H W (1991) Characterisation of arginase from the extreme thermophile 'Bacillus caldovelox'. Biochimica et Biophysica Acta (BBA)—Protein Structure and Molecular Enzymology 1077(3):291-298

Rosenberg, Alan H., et al. "Vectors for selective expression of cloned DNAs by T7 RNA polymerase." Gene 56.1 (1987): 125-135.

Scalcinati G, Knuf C, Partow S, Chen Y, Maury J, Schalk M, Daviet L, Nielsen J, Siewers V (2012) Dynamic control of gene expression in Saccharomyces cerevisiae engineered for the production of plant sesquitepene α-santalene in a fed-batch mode. Metab Eng 14(2):91-103

Shao, Z., Zhao, H. & Zhao, H. DNA assembler, an in vivo genetic method for rapid construction of biochemical pathways. Nucleic Acids Res. 37, e16 (2009).

Schneider, Jens, and Volker F. Wendisch. "Putrescine production by engineered Corynebacterium glutamicum." Applied microbiology and biotechnology 88.4 (2010): 859-868.

Song W, Niu P, Chen X, Liu L (2014) Enzymatic production of l-ornithine from 1-arginine with recombinant thermophilic arginase. Journal of Molecular Catalysis B: Enzymatic 110(0):1-7

Subhi A L, Diegelman P, Porter C W, Tang B, Lu Z J, Markham G D, Kruger W D. Methylthioadenosine phosphorylase regulates ornithine decarboxylase by production of downstream metabolites. J Biol Chem. 2003; 278(50):49868-73

Zhan Y, Liu J, Mao P, Zhang H, Liu Q, Jiao Q (2013) Biotransformation of 1-ornithine from 1-arginine using whole-cell recombinant arginase. World J Microbiol Biotechnol 29(11):2167-2172 doi:10.1007/s11274-013-1382-5

The invention claimed is:

1. A genetically modified fungal cell modified for enhanced L-ornithine biosynthesis from α-ketoglutarate, wherein (1) the L-ornithine biosynthesis from α-ketoglutarate is cytosolic and the fungal cell is modified to comprise at least one of the genes selected from a group consisting of:

(a) a gene encoding a cytosolic glutamate N-acetyltransferase (EC 2.3.1.1);
(b) a gene encoding a cytosolic N-acetylglutamate kinase (EC 2.7.2.8);
(c) a gene encoding a cytosolic N-acetyl-gamma-glutamyl-phosphate reductase (EC.1.2.1.38);
(d) a gene encoding a cytosolic acetylornithine aminotransferase (EC 2.6.1.11); and
(e) a gene encoding a cytosolic ornithine acetyltransferase (EC 2.3.1.35); or (2) the genetically modified fungal cell is genetically modified for overexpression of L-ornithine transporter of the mitochondrial inner membrane and/or for overexpression of L-glutamate transporter; and for overexpression of:

(a) a gene encoding an N-acetylglutamate kinase (EC 2.7.2.8) and N-acetyl-gamma-glutamyl-phosphate reductase (EC.1.2.1.38);
(b) a gene encoding a mitochondrial ornithine acetyltransferase (EC 2.3.1.35);
(c) a gene encoding an acetylornithine aminotransferase (EC 2.6.1.11); and
(d) a gene encoding an acetylglumate synthase (EC 2.3.1.1).

2. The genetically modified fungal cell according to claim 1, wherein the cytosolic glutamate N-acetyltransferase is argA, the cytosolic N-acetylglutamate kinase is argB, the cytosolic N-acetyl-gamma-glutamyl-phosphate reductase is argC, the cytosolic acetylornithine aminotransferase is argD and the cytosolic ornithine acetyltransferase is argJ.

3. The genetically modified fungal cell according to claim 2, wherein the argA and agrB are obtained from *Escherichia coli* and the argC, argD and argJ are from *Corynebacterium glutamicum*.

4. The genetically modified fungal cell according to claim 1, wherein the gene encoding an N-acetylglutamate kinase and N-acetyl-gamma-glutamyl-phosphate reductase is ARG5,6; the gene encoding a mitochondrial ornithine acetyltransferase is ARG7; the gene encoding an acetylornithine aminotransferase is ARG8; and the gene encoding an acetylglumate synthase is ARG2.

5. The genetically modified fungal cell according to claim 4, wherein ARG5,6, ARG7, ARG8, and ARG2 are from *Saccharomyces cerevisiae*.

6. The genetically modified fungal cell according to claim 1, wherein said fungal cell is genetically modified for overexpression of
a gene encoding NADP+-dependent glutamate dehydrogenase, wherein the NADP+-dependent glutamate dehydrogenase is optionally GDH1 from *S. cerevisiae*.

7. The genetically modified fungal cell according to claim 1, wherein said fungal cell is genetically modified for enhanced α-ketoglutarate biosynthesis by overexpression of at least one gene selected from the group consisting of: (a) a gene encoding glutamate dehydrogenase (EC:1.4.1.4), a gene encoding a glutamine synthetase (EC:6.3.1.2), and a gene encoding a glutamate synthase (EC 1.4.1.14).

8. The genetically modified fungal cell according to claim 1, wherein said fungal cell is genetically modified for attenuated glucose uptake.

9. The genetically modified fungal cell according to claim 8, wherein said fungal cell is genetically modified for overexpression of a gene encoding a glucose transporter regulator protein.

10. The genetically modified fungal cell according to claim 1, wherein said fungal cell is genetically modified for overexpression of a gene encoding an arginase (EC3.5.3.1).

11. The genetically modified fungal cell according to claim 1, wherein said fungal cell produces a polyamine selected from the group consisting of putrescine, spermidine and spermine; and said eukaryotic cell is genetically modified for overexpression of a gene encoding ornithine decarboxylase (ODC) (EC 4.1.1.17) and/or attenuated activity of ODC antizyme.

12. The genetically modified fungal cell according to claim 11, wherein said fungal cell is genetically modified for overexpression of the gene SPE1 (ornithine decarboxylase) from *S. cerevisiae* and deletion or disruption of the endogenous gene OAZ1 (ornithine decarboxylase antizyme).

13. The genetically modified fungal cell according to claim 1, wherein said fungal cell produces a polyamine selected from the group consisting of spermidine and spermine; and said fungal cell is genetically modified for overexpression of:
(a) a gene encoding an S-adenosylmethionine decarboxylase (EC 4.1.1.50); and/or
(b) a gene encoding a spermidine synthase (EC 2.5.1.16).

14. The genetically modified fungal cell according to claim 11, wherein said fungal cell produces a polyamine selected from the group consisting of spermidine and spermine; and said fungal cell is genetically modified for expression of a gene encoding a carboxynorspermidine dehydrogenase and/or a gene encoding a carboxynorspermidine decarboxylase.

15. The genetically modified fungal cell according to claim 11, wherein said fungal cell produces spermine; and said eukaryotic cell is genetically modified for overexpression of a gene encoding a spermine synthase (EC 2.5.1.22).

16. The genetically modified fungal cell according to claim 11, wherein said fungal cell is genetically modified for overexpression of a gene encoding a polyamine transporter.

17. The genetically modified fungal cell according to claim 1, wherein said fungal cell is a yeast cell selected from a genus consisting of the group consisting of *Saccharomyces, Cryptococcus, Trichosporon, Zygosaccharomyces, Debaromyces, Pichia, Schizosaccharomyces, Trigonopsis, Brettanomyces, Aureobasidium, Nadsonia, Lipomyces, Torulopsis, Kloeckera, Phaffia, Rhodotorula, Candida, Hansenula, Kluyveromyces, Yarrowia*, and *Schwanniomyces*.

18. A process for production of L-ornithine or derived products, said process comprising cultivating the genetically modified fungal cell according to claim 1 in the presence of a carbon source.

19. The process according to claim 18, wherein said carbon source is selected from a group consisting of hemicelluloses, celluloses, pectines, rhamnose, fucose, maltose, galactose, maltodextrines, ribose, ribulose, starch, sucrose, glycerol, lactose, glucose, xylose, arabinose, fructose, galactose, glycerol, raffinose and lactose.

20. The genetically modified fungal cell according to claim 1, wherein the L-ornithine transporter is ORT1 from *S. cerevisiae* and/or the L-glutamate transporter is AGC1 from *S. cerevisiae*.

21. The genetically modified fungal cell according to claim 7, wherein the gene encoding glutamate dehydrogenase (EC:1.4.1.4) is GDH1 or GDH3 from *S. cerevisiae* (SEQ ID NO:6 or SEQ ID NO:7, respectively); the gene encoding a glutamine synthetase (EC:6.3.1.2) is GLN1 from *S. cerevisiae* (SEQ ID NO:8), and the gene encoding a glutamate synthase (EC 1.4.1.14) is GLT1 from *S. cerevisiae* (SEQ ID NO:9).

22. The genetically modified fungal cell according to claim 9, wherein the gene encoding a glucose transporter regulator protein is MTH1 from *S. cerevisiae*.

23. The genetically modified fungal cell according to claim 10, wherein the gene encoding an arginase (EC3.5.3.1) is CAR1 (SEQ ID NO: 1).

24. The genetically modified fungal cell according to claim 14, wherein the carboxynorspermidine dehydrogenase is Cj0172c from *Campylobacter jejuni* (SEQ ID NO:46), VC1624 from *Vibrio cholera* (SEQ ID NO:48) or Lys1 from *Bacteroides uniformis* (SEQ ID NO:50) and the carboxynorspermidine decarboxylase is Cj1515c from *Campylobacter jejuni* (SEQ ID NO:47), VC1623 from *Vibrio cholera* (SEQ ID NO:49) or nspC from *Bacteroides uniformis* (SEQ ID NO:51).

* * * * *

UNITED STATES PATENT AND TRADEMARK OFFICE
CERTIFICATE OF CORRECTION

PATENT NO. : 10,544,435 B2
APPLICATION NO. : 15/556737
DATED : January 28, 2020
INVENTOR(S) : Qin et al.

It is certified that error appears in the above-identified patent and that said Letters Patent is hereby corrected as shown below:

In the Specification

Column 23, Line 39: Please correct "Mia" to read -- M1a --

Column 24, Line 43: Please correct "80 mg" to read -- 80 $l^{-1}$ mg --

Column 25, Line 32: Please correct "Odd p" to read -- Odc1p --

Column 26, Line 59: Please correct "DTI" to read -- CIT1 --

Column 28, Line 42: Please correct "Guldener" to read -- Güldener --

Column 28, Line 50: Please correct "Giildener" to read -- Güldener --

Column 29, Line 53: Please correct "10p 1" to read -- 10μl --

Column 47, Line 26: Please correct "Jam" to read -- Jörn --

Signed and Sealed this
Seventh Day of July, 2020

Andrei Iancu
*Director of the United States Patent and Trademark Office*